(12) United States Patent
Hyde et al.

(10) Patent No.: US 7,879,973 B2
(45) Date of Patent: *Feb. 1, 2011

(54) METHODS FOR ARBITRARY PEPTIDE SYNTHESIS

(75) Inventors: Roderick A. Hyde, Livermore, CA (US); Edward K. Y. Jung, Bellevue, WA (US); Lowell L. Wood, Jr., Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 767 days.

This patent is subject to a terminal disclaimer.

(21) Appl. No.: 11/478,539

(22) Filed: Jun. 29, 2006

(65) Prior Publication Data

US 2008/0003580 A1 Jan. 3, 2008

(51) Int. Cl.
*C12P 1/00* (2006.01)
(52) U.S. Cl. .................. 530/333; 435/41; 536/23.1; 702/19; 506/43
(58) Field of Classification Search ............ None
See application file for complete search history.

(56) References Cited

U.S. PATENT DOCUMENTS

| | | | |
|---|---|---|---|
| 3,647,390 | A | 3/1972 | Kubodera et al. |
| 5,081,584 | A | 1/1992 | Omichinski et al. |
| 5,218,101 | A | 6/1993 | Hansen |
| 5,358,862 | A | 10/1994 | Hardesty et al. |
| 5,562,622 | A | 10/1996 | Tihon |
| 5,635,400 | A | 6/1997 | Brenner |
| 6,457,361 | B1 | 10/2002 | Takeuchi et al. |
| 6,562,622 | B1 | 5/2003 | Hudson et al. |
| 6,620,587 | B1 | 9/2003 | Taussig et al. |
| 6,722,200 | B2 * | 4/2004 | Roukes et al. ............ 73/580 |
| 6,846,638 | B2 | 1/2005 | Shipwash |
| 7,247,448 | B2 | 7/2007 | Erdmann et al. |
| 7,799,542 | B2 | 9/2010 | Hyde et al. |
| 2002/0127623 | A1 | 9/2002 | Minshull et al. |
| 2003/0100000 | A1 | 5/2003 | Martin |
| 2005/0260653 | A1 | 11/2005 | Labaer et al. |
| 2006/0078888 | A1 | 4/2006 | Griffiths et al. |
| 2006/0223178 | A1 | 10/2006 | Barber et al. |
| 2007/0119510 | A1 * | 5/2007 | Kartalov et al. ........... 137/825 |
| 2009/0081643 | A1 | 3/2009 | Preminger et al. |

FOREIGN PATENT DOCUMENTS

| WO | WO 2004/050825 | * | 6/2004 |
|---|---|---|---|
| WO | WO 2004/050825 A2 | | 6/2004 |

OTHER PUBLICATIONS

Forster, Anthony C.; Weissbach, Herbert; Blacklow, Stephen C.; "A Simplified Reconstitution of mRNA-Directed Peptide Synthesis: Activity of the Epsilon Enhancer and an Unnatural Amino Acid"; Analytical Biochemistry; bearing a date of 2001; pp. 60-70; vol. 297; Academic Press.

Josephson, Kristopher; Hartman, Matthew C. T.; Szostak, Jack W.; "Ribosomal Synthesis of Unnatural Peptides"; Journal of the American Chemical Society; Jul. 28, 2005; pp. 11727-11735; vol. 127 (33); American Chemical Society; Washington DC.

Beaulande, Melanie; Tarbouriech, Nicolas; Hartlein, Michael; "Human Cytosolic Asparaginyl-tRNA Synthetase: cDNA Sequence, Functional Expression in *Escherichia Coli* and Characterization as Human Autoantigen"; Nucleic Acids Research; bearing a date of 1998; pp. 521-524; vol. 26, No. 2; Oxford University Press.

Beringer, Malte; Bruell, Christian; Xiong, Liqun; Pfister, Peter; Bieling, Peter; Katunin, Vladimir I.; Mankin, Alexander S.; Bottger, Erik C.; Rodnina, Marina V.; "Essential Mechanisms in the Catalysis of Peptide Bond Formation on the Ribosome"; The Journal of Biological Chemistry; bearing a date of Oct. 28, 2005; pp. 36065-36072; vol. 280, No. 43; The American Society for Biochemistry and Molecular Biology, Inc.

Blanchard, Scott C.; Gonzalez, Ruben L., Jr.; Kim, Harold D.; Chu, Steven; Puglisi, Joseph D.; "Articles: tRNA Selection and Kinetic Proofreading in Translation"; Nature Structural & Molecular Biology; bearing a date of Oct. 2004; pp. 1008-1014; vol. 11, No. 10; Nature Publishing Group; located at: http://www.nature.com/natstructmolbiol.

Blanchard, Scott C.; Kim, Harold D.; Gonzalez, Ruben L., Jr.; Puglisi, Joseph D.; Chu, Steven; "Biophysics: tRNA Dynamics on the Ribosome During Translation"; PNAS; bearing a date of Aug. 31, 2004; pp. 12893-12898; vol. 101, No. 35; The National Academy of Sciences of the USA; located at: www.pnas.org/chi/doi/10.1073/pnas.0403884101.

Bocchetta, Maurizio; Xiong, Liqun; Mankin, Alexander S.; "23S rRNA Positions Essential for tRNA Binding in Ribosomal Functional Sites"; Proceedings of the National Academy of Sciences; bearing a date of Mar. 1998; pp. 3525-3530; vol. 95; The National Academy of Sciences; located at: http://www.pnas.org.

Brandt, Ole; Hoheisel, Jorg D.; "Opinion: Peptide Nucleic Acids on Microarrays and Other Biosensors"; Trends in Biotechnology; bearing a date of Dec. 2004; pp. 617-622; vol. 22, No. 12; Elsevier Ltd; located at: www.sciencedirect.com.

Brune, Martin; Hunter, Jackie L.; Howell, Steven A.; Martin, Stephen R.; Hazlett, Theodore L.; Corrie, John E.T.; Webb, Martin R.; "Mechanism of Inorganic Phosphate Interaction with Phosphate Binding Protein from *Escherichia Coli*"; Biochemistry; bearing a date of 1998; pp. 10370-10380; vol. 37; American Chemical Society.

Capone, John P.; Sharp, Phillip A.; Rajbhandary, Uttam L.; "Amber, Ochre and Opal Suppressor tRNA Genes Derived From a Human Serine tRNA Gene"; The EMBO Journal; bearing a date of 1985; pp. 213-221; vol. 4, No. 1; IRL Press Limited, Oxford, England.

Dale, Taraka; Uhlenbeck, Olke C.; "Letter to the Editor: Binding of Misacylated tRNAs to the Ribosomal A Site"; RNA; bearing a date of 2005; pp. 1610-1615; vol. 11; Cold Spring Harbor Laboratory Press—RNA Society.

(Continued)

*Primary Examiner*—Christopher Low
*Assistant Examiner*—Christopher M Gross
(74) *Attorney, Agent, or Firm*—Workman Nydegger

(57) ABSTRACT

Methods, apparatus, systems, computer programs and computing devices related to biologically assembling and/or synthesizing peptides and/or proteins are disclosed.

50 Claims, 23 Drawing Sheets

OTHER PUBLICATIONS

Dale, Taraka; Uhlenbeck, Olke C.; "Opinion: Amino Acid Specificity in Translation"; Trends in Biochemical Sciences; bearing a date of Dec. 2005; pp. 659-665; vol. 30, No. 12; Elsevier Ltd; located at: www.sciencedirect.com.

Deisingh, Anil K.; "I-Section: MEMS Technology in Analytical Chemistry"; The Analyst; bearing a date of 2003; pp. 9-11; vol. 128; The Royal Society of Chemistry.

Dittmar, Kimberly A.; Goodenbour, Jeffrey M.; Pan, Tao; "Tissue-Specific Differences in Human Transfer RNA Expression"; PLOS Genetics; bearing a date of Dec. 2006; pp. 2107-2115; vol. 2, No. 12 e221; located at: www.plosgenetics.org.

Dorywalska, Magdalena; Blanchard, Scott C.; Gonzalez, Ruben L., Jr.; Kim, Harold D.; Chu, Steven; Puglisi, Joseph D.; "Site-Specific Labeling of the Ribosome for Single-Molecule Spectroscopy"; Nucleic Acids Research; bearing a date of 2005; pp. 182-189; vol. 33, No. 1; Oxford University Press.

Englisch, Sabine; Englisch, Uwe; Von Der Haar, Friedrich; Cramer, Friedrich; "The Proofreading of Hydroxy Analogues of Leucine and Isoleucine by Leucyl-tRNA Synthetases from *E. Coli* and Yeast"; Nucleic Acids Research; bearing a date of 1986; pp. 7529-7539; vol. 14, No. 19; IRL Press Limited, Oxford, England.

Flick, Jeffrey S.; Thorner, Jeremy; "Genetic and Biochemical Characterization of a Phosphatidylinositol-Specific Phospholipase C in Saccharomyces Cerevisiae"; Molecular and Cellular Biology; bearing a date of Sep. 1993; pp. 5861-5876; vol. 13, No. 9; American Society for Microbiology.

Gabriel, Kaigham J.; "Machines, Materials and Manufacturing: Engineering Microscopic Machines"; Scientific American; bearing a date of Sep. 1995; pp. 150-153; Scientific American, Inc.

Gau, Jen-Jr; Lan, Esther H.; Dunn, Bruce; Ho, Chih-Ming; Woo, Jason C.S.; "A MEMS Based Amperometric Detector for *E. Coli* Bacteria Using Self-Assembled Monolayers"; Biosensors & Bioelectronics; bearing a date of 2001; pp. 745-755; vol. 16; Elsevier Science B.V.

Hartman, Matthew C.T.; Josephson, Kristopher; Szostak, Jack W.; "Enzymatic Aminoacylation of tRNA with Unnatural Amino Acids"; PNAS; bearing a date of Mar. 21, 2006; pp. 4356-4361; vol. 103, No. 12; The National Academy of Sciences of the USA; located at: www.pnas.org/cgi/doi/10.1073/pnas.0509219103.

Henderson, Matthew P.A.; Billen, Lieven P.; Kim, Peter K.; Andrews, David W.; "Cell-Free Analysis of Tail-Anchor Protein Targeting to Membranes"; Methods; bearing a date of 2007; pp. 427-438; vol. 41; Elsevier, Inc.; located at: www.sciencedirect.com or www.elsevier.com/locate/ymeth.

Hoffmann, A.; Roeder, R.G.; "Purification of His-Tagged Proteins in Non-Denaturing Conditions Suggests a Convenient Method for Protein Interaction Studies"; Nucleic Acids Research; bearing a date of Aug. 23, 1991; pp. 6337-6338; vol. 19, No. 22; Laboratory of Biochemistry and Molecular Biology, The Rockefeller University, New York, NY, USA.

Hohsaka, Takahiro; Ashizuka, Yuki; Murakami, Hiroshi; Sisido, Masahiko; "Five-Base Codons for Incorporation of Nonnatural Amino Acids into Proteins"; Nucleic Acids Research; bearing a date of 2001; pp. 3646-3651; vol. 29, No. 17; Oxford University Press.

Hohsaka, Takahiro; Ashizuka, Yuki; Taira, Hikaru; Murakami, Hiroshi; Sisido, Masahiko; "Incorporation of Nonnatural Amino Acids into Proteins by Using Various Four-Base Codons in an *Escherichia Coli* in Vitro Translation System"; Biochemistry; bearing a date of 2001; pp. 11060-11064; vol. 40; American Chemical Society.

Huang, Yanyi; Castrataro, Piero; Lee, Cheng-Chung; Quake, Stephen R.; "Communication: Solvent Resistant Microfluidic DNA Synthesizer"; Lab on a Chip; bearing a date of 2007; pp. 24-26; vol. 7; The Royal Society of Chemistry; located at: www.rsc.org/loc.

Huh, Dongeun; Mills, K.L.; Zhu, Xiaoyue; Burns, Mark A.; Thouless, M.D.; Takayama, Shuichi; "Letters: Tuneable Elastomeric Nanochannels for Nanofluidic Manipulation"; Nature Materials; bearing a date of Jun. 2007; pp. 424-428; vol. 6; Nature Publishing Group; located at: www.nature.com/naturematerials.

Hyun, Soonsil; Hyun Lee, Kyung; Yu, Jaehoon; "A Strategy for the Design of Selective RNA Binding Agents. Preparation and RRE RNA Binding Affinities of a Nemycin-Peptide Nucleic Acid Heteroconjungate Library"; Bioorganic & Medicinal Chemistry Letters; bearing a date of 2006; pp. 4757-4759; vol. 16; Elsevier Ltd.; located at: www.sciencedirect.com.

Ibrahim, Nader G.; Burke, James P.; Beattie, Diana S.; "The Sensitivity of Rat Liver and Yeast Mitochondrial Ribosomes to Inhibitors of Protein Synthesis"; The Journal of Biological Chemistry; bearing a date of Nov. 10, 1974; pp. 6806-6811; vol. 249, No. 21; located at: www.jbc.org.

Jackson, R.J.; Napthine, S.; Brierley, I.; Development of a tRNA-Dependent in Vitro Translation System; RNA; bearing a date of 2001; pp. 765-773; vol. 7; RNA Society; located at: www.majournal.org.

Jankowsky, Eckhard; Strunk, Gunther; Schwenzer, Bernd; "Peptide Nucleic Acid (PNA) is Capable of Enhancing Hammerhead Ribozyme Activity with Long But Not With Short RNA Substrates"; Nucleic Acids Research; bearing a date of 1997; pp. 2690-2693; vol. 25, No. 14; Oxford University Press.

Joseph, Simpson; Noller, Harry F.; "Mapping the rRNA Neighborhood of the Acceptor End of tRNA in the Ribosome"; the EMBO Journal; bearing a date of 1996; pp. 910-916; vol. 15, No. 4; Oxford University Press.

Korencic, Dragana; Soll, Dieter; Ambrogelly, Alexandre; "A One-Step Method for In Vitro Production of tRNA Transcripts"; Nucleic Acids Research; bearing a date of 2002; pp. 1-4; vol. 30, No. 20 e105; Oxford University Press.

Lee, Byeong J.; De La Pena, Pilar; Tobian, Janet A.; Zasloff, Michael; Hatfield, Dolph; "Unique Pathway of Expression of an Opal Suppressor Phosphoserine tRNA"; Biochemistry—Proceedings of the National Academy of Sciences; bearing a date of Sep. 1987; pp. 6384-6388; vol. 84.

Magota, Koji; Otsuji, Nozomu; Miki, Takeyoshi; Horiuchi, Tadao; Tsunasawa, Susumu; Kondo, Jun; Sakiyama, Fumio; Amemura, Mitsuko; Morita, Takashi; Shinagawa, Hideo; Nakata, Atsuo; "Nucleotide Sequence of the phoS Gene, the Structural Gene for the Phosphate-Binding Protein of *Escherichia Coli*"; Journal of Bacteriology; bearing a date of Mar. 1984; pp. 909-917; vol. 157, No. 3; American Society for Microbiology.

Mhlanga, Musa M.; Vargas, Diana Y.; Fung, Cindy W.; Kramer, Fred Russell; Tyagi, Sanjay; "tRNA-Linked Molecular Beacons for Imaging mRNAs in the Cytoplasm of Living Cells"; Nucleic Acids Research; bearing a date of 2005; pp. 1902-1912; vol. 33, No. 6; The Author—Oxford University Press.

Moraes, Christopher; Simmons, Craig A.; Sun, Yu; "Cell Mechanics Meets MEMS"; CSME Bulletin SCGM; bearing a date of Fall 2006; pp. 15-18; Mechanical and Industrial Engineering, Institute of Biomaterials and Biomedical Engineering, University of Toronto.

Moriyama, Kei; Kimoto, Michiko; Mitsui, Tsuneo; Yokoyama, Shigeyuki; Hirao, Ichiro; "Site-Specific Biotinylation of RNA Molecules by Transcription Using Unnatural Base Pairs"; Nucleic Acids Research; bearing a date of Aug. 19, 2005; pp. 1-8; vol. 33, No. 15 e129; The Author—Oxford University Press.

Nagata, Hideya; Hirano, Ken; Tabuchi, Mari; Baba, Yoshinobu; "Application of the Thermal Lens Microscope as a Detector of the Biopolymer in Microchip Electrophoresis"; 7th International Conference on Miniaturized Chemical and Biochemical Analysis Systems; bearing a date of Oct. 5-9, 2003; pp. 367-370.

Noren, Christopher J.; Anthony-Cahill, Spencer J.; Suich, Daniel J.; Noren, Karen A.; Griffith, Michael C.; Schultz, Peter G.; "In Vitro Suppression of an Amber Mutation by a Chemically Aminoacylated Transfer RNA Prepared by Runoff Transcription"; Nucleic Acids Research; bearing a date of Jan. 11, 1990; pp. 83-88; vol. 18, No. 1; Department of Chemistry, University of California, Berkeley, CA; located at: http://www.pubmedcentral.nih.gov/articlerender.fcgi?artid=330206.

Okoh, Michael P.; Hunter, Jackie L.; Corrie, John E.T.; Webb, Martin R.; "A Biosensor for Inorganic Phosphate Using a Rhodamine-Labeled Phosphate Binding Protein"; Biochemistry; bearing a date of 2006; pp. 14764-14771; vol. 45; American Chemical Society.

Pavlov, Michael Yu; Ehrenberg, Mans; "Rate of Translation of Natural mRNAs in an Optimized in Vitro System"; Archives of Biochemistry and Biophysics; bearing a date of Apr. 1, 1996; pp. 9-16; vol. 328, No. 1; Academic Press, Inc.

Pfisterer, J.; Buetow, D.E.; "In Vitro Reconstruction of the Mitochondrial Translation System of Yeast"; Biochemistry—Proceedings of the National Academy of Sciences; bearing a date of Aug. 1981; pp. 4917-4921; vol. 78, No. 8; Department of Physiology and Biophysics, University of Illinois, Urbana, Illinois.

Polla, Dennis L.; Erdman, Arthur G.; Robbins, William P.; Markus, David T.; Diaz-Diaz, Jorge; Rizq, Raed; Nam, Yunwoo; Brickner, Hui Tao; "Microdevices in Medicine"; Annual Review of Biomedical Engineering; bearing a date of 2000; pp. 551-576; vol. 2; located at: arjournals.annualreviews.org.

Robertson, Stephanie A.; Noren, Christopher J.; Anthony-Cahill, Spencer J.; Griffith, Michael C.; Schultz, Peter G.; "The Use of 5'-phospho-2 Deoxyribocytidylylriboadenosine as a Facile Route to Chemical Aminoacylation of tRNA"; Nucleic Acids Research; bearing a date of 1989; pp. 9649-9660; vol. 17, No. 23; Department of Chemistry, University of California, Berkeley, CA.

Saito, Hirohide; Kourouklis, Dimitrios; Suga, Hiroaki; "An in Vitro Evolved Precursor tRNA with Aminoacylation Activity"; The EMBO Journal; bearing a date of 2001; pp. 1797-1806; vol. 20, No. 7; European Molecular Biology Organization.

Sampson, Jeffrey R.; Uhlenbeck, Olke C.; "Biochemical and Physical Characterization of an Unmodified Yeast Phenylalanine Transfer RNA Transcribed in Vitro"; Biochemistry—Proceedings of the National Academy of Sciences; bearing a date of Feb. 1988; pp. 1033-1037; vol. 85; Department of Chemistry and Biochemistry—University of Colorado.

Sato, Kiichi; Yamanaka, Maho; Hagino, Tomokazu; Tokeshi, Manabu; Kimura, Hiroko; Kitamori, Takehiko; "Paper: Microchip-Based Enzyme-Linked Immunosorbent Assay (microELISA) System with Thermal Lens Detection"; Miniaturisation for Chemistry, Biology & Bioengineering—Lab on a Chip; bearing a date of 2004; pp. 570-575; vol. 4; The Royal Society of Chemistry.

Shipwash, Edward; "Microarrays for Amino Acid Analysis and Protein Sequencing"; bearing a date of Aug. 10, 1999; pp. 1-21; located at: http://arxiv.org/abs/physics/9908021.

Shutes, Adam; Der, Channing J.; "Real-Time in Vitro Measurement of GTP Hydrolysis"; Methods; bearing a date of 2005; pp. 183-189; vol. 37; Elsevier, Inc.; located at: www.sciencedirect.com and www.elsevier.com/locate/ymeth.

Steege, Deborah A.; "A Nucleotide Change in the Anticodon of an *Escherichia Coli* Serine Transfer RNA Results in supD-Amber Suppression"; Nucleic Acids Research; bearing a date of 1983; pp. 3823-3832; vol. 11, No. 11; IRL Press Limited, Oxford, England.

Taira, Hikaru; Hohsaka, Takahiro; Sisido, Masahiko; "In Vitro Selection of tRNAs for Efficient Four-Base Decoding to Incorporate Non-Natural Amino Acids into Proteins in an *Escherichia Coli* Cell-Free Translation System"; Nucleic Acids Research; bearing a date of 2006; pp. 1653-1662; vol. 34, No. 5; Oxford University Press.

Takahashi, Shuntaro; Akita, Ryoko; Furusawa, Hiroyuki; Shimizu, Yoshihiro; Ueda, Takuya; Okahata, Yoshio; "Kinetic Analysis of Ribosome Binding Process onto mRNA Using a Quartz-Crystal Microbalance"; Nucleic Acids Symposium Series; bearing a date of 2006; pp. 49-50; vol. 50; Oxford University Press.

Takeishi, Keiichi; Ukita, Tyunosin; "Characterization of Two Species of Methionine Transfer Ribonucleic Acid from Bakers' Yeast"; The Journal of Biological Chemistry; bearing a date of Nov. 10, 1968; pp. 5761-5769; vol. 243, No. 21; located at: www.jbc.org.

Taki, Masumi; Hohsaka, Takahiro; Murakami, Hiroshi; Taira, Kazunari; Sisido, Masahiko; "Position-Specific Incorporation of a Fluorophore—Quencher Pair into a Single Streptavidin Through Orthogonal Four-Base Codon/Anticodon Pairs"; Journal of the American Chemical Society; bearing a date of 2002; pp. 14586-14590; vol. 124; American Chemical Society.

Taki, Masumi; Kuno, Atsushi; Matoba, Shinsuke; Kobayashi, Yuki; Futami, Junichiro; Murakami, Hiroshi; Suga, Hiroaki; Taira, Kazunari; Hasegawa, Tsunemi; Sisido, Masahiko; "Leucyl/Phenylalanyl-tRNA-Protein Transferase-Mediated Chemoenzymatic Coupling of N-Terminal Arg/Lys Units in Post-Translationally Processed Proteins with Non-Natural Amino Acids"; ChemBioChem; bearing a date of 2006; pp. 1676-1679; vol. 7; Wiley-VCH Verlag GmbH & Co. KGaA, Weinheim.

"Tech Tip #5: Attach an Antibody onto Glass, Silica or Quartz Surface"; Pierce; bearing a date of 2006; pp. 1-4; Pierce Biotechnology, Inc.

Ulbrich, Beate; Czempiel, Winfried; Bass, Rolf; "Mammalian Mitochondrial Ribosomes"; European Journal of Biochemistry; bearing a date of 1980; pp. 337-343; vol. 108; FEBS.

Vanzi, Francesco; Takagi, Yasuharu; Shuman, Henry; Cooperman, Barry S.; Goldman, Yale E.; "Mechanical Studies of Single Ribosome/mRNA Complexes"; Biophysical Journal; bearing a date of Sep. 2005; pp. 1909-1919; vol. 89; Biophysical Society.

Vanzi, Francesco; Vladimirov, Serguei; Knudsen, Charlotte R.; Goldman, Yale E.; Cooperman, Barry S.; "Report: Protein Synthesis by Single Ribosomes"; RNA; bearing a date of 2003; pp. 1174-1179; vol. 9; Cold Spring Harbor Laboratory Press–RNA Society.

Zhang, Wenhua; Baskaran, Rajashree; Turner, Kimberly L.; "Non-linear Behavior of a Parametric Resonance-Based Mass Sensor"; Proceedings of IMECE2002-33261 ASME International Mechanical Engineering Congress & Exposition; bearing a date of Nov. 17-22, 2002; pp. 1-5; New Orleans, Louisiana; ASME.

Adelman, M.R.; Blobel, Gunter; Sabatini, David D.; "An Improved Cell Fractionation Procedure for the Preparation of Rat Liver Membrane-Bound Ribosomes"; The Journal of Cell Biology; Bearing a date of 1973; pp. 191-205; vol. 56; located at: www.jcb.org.

Asahara, Haruichi; Uhlenbeck, Olke C.; "Predicting the Binding Affinities of Misacylated tRNAs for *Thermus Thermophilus* EF-Tu•GTP"; Biochemistry; Bearing dates of 2005 and Jul. 29, 2005; pp. 11254-11261; vol. 44, No. 33; American Chemical Society.

Beebe, David J.; Mensing, Glennys A.; Walker, Glenn M.; "Physics and Applications of Microfluidics in Biology"; Annual Review of Biomedical Engineering; bearing a date of 2002; pp. 261-286; vol. 4; Annual Reviews; located at: arjournals.annualreviews.org.

Bessho, Yoshitaka; Hodgson, David R.W.; Suga, Hiroaki; "Research Article: A tRNA Aminoacylation System for Non-Natural Amino Acids Based on a Programmable Ribozyme"; Nature Biotechnology; bearing dates of Jul. 2002; pp. 723-728; vol. 20; Nature Publishing Group; located at: http://biotech.nature.com.

Burns, Mark A.; Johnson, Brian N.; Brahmasandra, Sundaresh N.; Handique, Kalyan; Webster, James R.; Krishnan, Madhavi; Sammarco, Timothy S.; Man, Piu M.; Jones, Darren; Heldsinger, Dylan; Mastrangelo, Carlos H.; Burke, David T.; "Reports: An Integrated Nanoliter DNA Analysis Device"; Science Magazine; bearing a date of Oct. 16, 1998; pp. 484-487; vol. 282; located at: www.sciencemag.com.

Cheng, Siew Bang; Skinner, Cameron D.; Taylor, Justine; Attiya, Said; Lee, William E.; Piceill, Gilles; Harrison, D. Jed; "Development of a Multichannel Microfluidic Analysis System Employing Affinity Capillary Electrophoresis for Immunoassay"; Analytical Chemistry; bearing a date of Apr. 1, 2001; pp. 1472-1479; vol. 73, No. 7; American Chemical Society.

Chin, Jason W.; Cropp, T. Ashton; Anderson, J. Christopher; Mukherji, Mridul; Zhang, Zhiwen; Schultz, Peter G.; "Reports: An Expanded Eukaryotic Genetic Code"; Science; bearing a date of Aug. 15, 2003; pp. 964-967; vol. 301; located at: www.sciencemag.org.

Curran, James F.; Yarus, Michael; "Rates of Aminoacyl-tRNA Selection at 29 Sense Codons in Vivo"; Journal of Molecular Biology; bearing a date of 1989; pp. 65-77; vol. 209; Academic Press Limited.

Forster, Anthony C.; Tan, Zhongping; Nalam, Madhavi N.L.; Lin, Hening; Qu, Hui; Cornish, Virginia W.; "Programming Peptidomimetic Syntheses by Translating Genetic Codes Designed de novo"; Biochemistry; bearing a date of May 27, 2003; pp. 6353-6357; vol. 100, No. 11; PNAS.

Gilchrist, Michael A.; Wagner, Andreas; "A Model of Protein Translation including Codon Bias, Nonsense Errors, and Ribosome Recycling"; Journal of Theoretical Biology; bearing a date of Apr. 21, 2006; pp. 417-434; vol. 239, No. 4; Elsevier Ltd; located at: www.elsevier.com/locate/yjtbi and www.sciencedirect.com.

Giordano, B.C.; Ferrance, J.; Swedberg, S.; Huhmer, A.F.R.; Landers, J.P.; "Polymerase Chain Reaction in Polymeric Microchips: DNA Amplification in Less Than 240 Seconds"; Analytical Biochemistry; bearing a date of 2001; pp. 124-132; vol. 291; Academic Press; located at: http://www.idealibrary.com.

Hendrickson, Tamara L.; Crécy-Lagard, Valérie De; Schimmel, Paul; "Incorporation of NonNatural Amino Acids Into Proteins"; Annual Reviews of Biochemistry; Bearing a date of 2004; pp. 147-176; vol. 73; Annual Reviews.

Hodgson, David R.W.; Sanderson, John M.; "Tutorial Review: The Synthesis of Peptides and Proteins Containing Non-Natural Amino Acids"; Chemistry Society Review; bearing a date of 2004; pp. 422-430; vol. 33; The Royal Society of Chemistry; located at: www.rsc.org/csr.

Ibba, Michael; "Science's Compass: Persectives: Protein Synthesis: Discriminating Right From Wrong"; Science; bearing a date of Oct. 5, 2001; pp. 70-71; vol. 294; located at: www.sciencemag.org.

Kapp, Lee D.; Lorsch, Jon R.; "The Molecular Mechanics of Eukaryotic Translation"; Annual Review of Biochemistry; bearing a date of 2004; pp. 657-704; vol. 73; Annual Reviews.

Köhrer, Caroline; Sullivan, Eric L.; Rajbhandary, Uttam L.; "Complete Set of Orthogonal 21$^{st}$ Aminoacyl-tRNA Synthetase-Amber, Ochre and Opal Suppressor tRNA Pairs: Concomitant Suppression of Three Different Termination Codons in an mRNA in Mammalian Cells"; Nucleic Acids Research; bearing a date of 2004; pp. 6200-6211; vol. 32, No. 21; Oxford University Press.

Kopp, Martin U.; De Mello, Andrew J.; Manz, Andreas; "Reports: Chemical Amplification: Continuous-Flow PCR on a Chip"; Science Magazine; bearing a date of May 15, 1998; pp. 1046-1048; vol. 280; located at: www.sciencemag.org.

Kourouklis, Dimitrios; Murakami, Hiroshi; Suga, Hiroaki; "Programmable ribozymes for mischarging tRNA with nonnatural amino acids and their applications to translation"; Methods; bearing a date of 2005; pp. 239-244; vol. 36; Elsevier Inc.; located at: www.sciencedirect.com.

Lariviere, Frederick J.; Wolfson, Alexey D.; Uhlenbeck, Olke C.; "Reports: Uniform Binding of Aminoacyl-tRNAs to Elongation Factor Tu by Thermodynamic Compensation"; Science; bearing a date of Oct. 5, 2001; pp. 165-168; vol. 294; located at: www.sciencemag.org.

Link, A. James; Tirrell, David A.; "Reassignment of Sense Condons in Vivo" Methods; bearing a date of 2005; pp. 291-298; vol. 36; Elsevier Inc.; located at: www.sciencedirect.com.

Lodder, Michiel; Wang, Bixun; Hecht, Sidney M.; "The N-pentenoyl Protecting Group for Aminoacyl-tRNAs" Methods; bearing a date of 2005; pp. 245-251; vol. 36; Elsevier Inc.; located at: www.sciencedirect.com.

Margulies, Marcel; Egholm, Michael; Altman, William E.; Attiya, Said; Bader, Joel S.; Bemben, Lisa A.; Berka, Jan; Braverman, Michael S.; Chen, Yi-Ju; Chen, Zhoutao; Dewell, Scott B.; Du, Lei; Fierro, Joseph M.; Gomes, Xavier V.; Godwin, Brian C.; He, Wen; Helgesen, Scott; Ho, Chun He; Irzyk, Gerard P.; Jando, Szilveszter C.; Alenquer, Maria L.I.; Jarvie, Thomas P.; Jirage, Kshama B.; Kim, Jong-Bum; Knight, James R.; Lanza, Janna R.; Leamon, John H.; Lefkowitz, Steven M.; Lei, Ming; Li, Jing; Lohman, Kenton L.; Lu, Hong; Makhijani, Vinod B.; McDade, Keith E.; McKenna, Michael P.; Myers, Eugene W.; Nickerson, Elizabeth; Nobile, John R.; Plant, Ramona; Puc, Bernard P.; Ronan, Michael T.; Roth, George T.; Sarkis, Gary J.; Simons, Jan Fredrik; Simpson, John W.; Srinivasan, Maithreyan; Tartaro, Karrie R.; Tomasz, Alexander; Vogt, Kari A.; Volkmer, Greg A.; Wang, Shally H.; Wang, Yong; Weiner, Michael P.; Yu, Pengguang; Begley, Richard F.; Rothberg, Jonathan M.; "Genome sequencing in microfabricated high-density picolitre reactors"; Nature; bearing a date of Sep. 15, 2005; pp. 376-380; vol. 437; Nature Publishing Group.

Mothes, Walther; Heinrich, Sven U.; Graf, Roland; Nilsson, Ingmarie; Von Heijne, Gunnar; Brunner, Josef; Rapoport, Tom A.; "Molecular Mechanism of Membrane Protein Integration into the Endoplasmic Reticulum"; Cell; bearing a date of May 16, 1997; pp. 523-533; vol. 89; Cell Press.

Ramakrishnan, V.; "Ribosome Structure and the Mechanism of Translation"; Cell; bearing a date of Feb. 22, 2002; pp. 557-572; vol. 108; Cell Press.

Rothschild, Kenneth J.; Gite, Sadanand; "tRNA-mediated Protein Engineering"; Biotechnology; bearing a date of 1999; pp. 64-70; vol. 10; Elsevier Science Ltd.; located at: http://biomednet.com/elecref/0958166901000064.

Sato, Kiichi; Tokeshi, Manabu; Odake, Tamao; Kimura, Hiroko; Ooi, Takeshi; Nakao, Masayuki; Kitamori, Takehiko; "Integration of an Immunosorbent Assay System: Analysis of Secretory Human Immunoglobulin A on Polystyrene Beads in a Microchip"; Analytical Chemistry; bearing a date of Mar. 15, 2000; pp. 1144-1147; vol. 72, No. 6; American Chemical Society.

Schmeing, T. Martin, Huang, Kevin S.; Strobel, Scott A.; Steitz, Thomas A.; "Letters: An Inducted-fit Mechanism to Promote Peptide Bond Formation and Exclude Hydrolysis of Peptidyl-tRNA"; Nature; bearing a date of Nov. 24, 2005; pp. 520-524; vol. 438; Nature Publishing Group.

Seiser, Robert M.; Nicchitta, Christopher V.; "The Fate of Membrane-bound Ribosomes Following the Termination of Protein Synthesis"; The Journal of Biological Chemistry; bearing a date of Oct. 27, 2000; pp. 33820-33827; vol. 275, No. 43; The American Society for Biochemistry and Molecular Biology, Inc.; located at: http://www.jbc.org.

Shimizu, Yoshihiro; Inoue, Akio; Tomari, Yukihide; Suzuki, Tsutomu; Yokogawa, Takashi; Nishikawa, Kazuya; Ueda, Takuya; "Research Article: Cell-free Translation Reconstituted With Purified Components"; Nature Biotechnology; bearing a date of Aug. 2001; pp. 751-755; vol. 19; Nature Publishing Group; located at: http://biotech.nature.com.

Shimizu, Yoshihiro; Kanamori, Takashi; Ueda, Takuya; "Protein synthesis by Pure Translation Systems"; Methods; bearing a date of 2005; pp. 299-304; vol. 36; Elsevier Inc.; located at: www.sciencedirect.com.

Sievers, Annette; Beringer, Malte; Rodnina, Marina V.; Wolfenden, Richard; "Biochemistry: The Ribosome as an Entropy Trap"; PNAS; bearing a date of May 25, 2004; pp. 7897-7901; vol. 101, No. 21; The National Academy of Sciences of the USA; located at: www.pnas.org/cgi/doi/10.1073/pnas.0402488101.

Sisido, Masahiko; Ninomiya, Keiko; Ohtsuki, Takashi; Hohsaka, Takahiro; "Four-base Condon/Anticondon Strategy and Non-Enzymatic Aminoacylation for Protein Engineering With Non-natural Amino Acids"; Methods; bearing a date of 2005; pp. 270-278; vol. 36; Elsevier Inc.; located at: www.sciencedirect.com.

Spirin, Alexander S.; Baranov, Vladimir I.; Ryabova, Lubov A.; Ovodov, Sergey Yu.; Alakhov, Yuly B.; "a Continuous Cell-Free Translation System Capable of Producing Polypeptides in High Yield"; Science; bearing a date of Nov. 25, 1998; pp. 1162-1164; vol. 242, No. 4882; Institute of Protein Research, Academy of Sciences of the USSR.

Squires, Todd M.; Quake, Stephen R.; "Microfluidics: Fluid Physics at the Nanoliter Scale"; Reviews of Modern Physics; bearing dates of Oct. 6, 2005 and Jul. 2005; pp. 977-1026; vol. 77; The American Physical Society.

Stone, H.A.; Stroock, A.D.; Ajdari, A.; "Engineering Flows in Small Devices: Microfluidics Toward a Lab-on-a-Chip"; Annual review of Fluid Mechanics; bearing a date of 2004; pp. 381-411, C1-C4; vol. 36; Annual Reviews; located at: arjournals.annualreviews.org.

Sundberg, Steven A.; "High-throughput and ultra-high-throughput screening: solution- and cell-based approaches"; Analytical Biotechnology; bearing a date of 2000; pp. 47-53; vol. 11; Elsevier Science Ltd.

Tan, Zhongping; Blacklow, Stephen C.; Cornish, Virginia W.; Forster, Anthony C.; "De Novo Genetic Codes and Pure Translation Display"; Methods; bearing a date of 2005; pp. 279-290; vol. 36; Elsevier Inc.; located at: www.sciencedirect.com.

Varenne, Stanislas; Buc, Jean; Lloubes, Roland; Lazdunski, Claude; "Translation is a Non-Uniform Process: Effect of tRNA Availability on the Rate of Elongation of Nascent Polypeptide Chains"; Journal of Molecular Biology; bearing a date of 1984; pp. 549-576; vol. 180; Academic Press Inc.

Wilding, Peter; Kricka, Larry J.; Cheng, Jing; Hvichia, Gia; Shoffner, Mann A.; Fortina, Paolo; "Integrated Cell Isolation and Polymerase Chain Reaction Analysis Using Silicon Microfilter Chambers"; Analytical Biochemistry; bearing a date of 1998; pp. 95-100; vol. 257; Academic Press.

Woese, Carl R.; "Perspective: Translation: in Retrospect and Prospect"; RNA; bearing a date of 2001; pp. 1055-1067; vol. 7, No. 8; Cambridge University Press.

Woese, Carl R.; Olsen, Gary J.; Ibba, Michael; Soll, Dieter; "Aminoacyl-tRNA Synthetases, the Genetic Code, and the Evolutionary Process" Microbiology and Molecular Biology Reviews; bearing a date of Mar. 2000; pp. 202-236; vol. 64, No. 1; American Society for Microbiology.

Xia, Xuhua; "How Optimized is the Translational Machinery in *Escherichia Coli*, *Salmonella Typhimurium* and *Saccharomyces Cerevisiae*?"; Genetics; bearing a date of May 1998; pp. 37-44; vol. 149; Genetics Society of America.

Xie, Jianming; Schultz, Peter G.; "An Expanding Genetic Code"; Methods; bearing a date of 2005; pp. 227-238; vol. 36; Elsevier Inc.; located at: www.sciencedirect.com.

Champe, et al.; Biochemistry $2^{nd}$ Edition, Lippincott's Illustrated Reviews; 1994; pp. 389-400; J. B. Lippincott Company, Philadelphia, PA.

Kelly M.; "Mainframe Graphics on a Microcomputer: Display Tektronix-type Plots on Your Microcomputer"; BYTE; Oct. 1983; vol. 8; pp. 439-442.

Menninger Jr.; "Computer Simulation of Ribosome Editing"; Journal of Molecular Biology; 1983; vol. 171; pp. 383-399.

Schilling-Bartetzko, Susanne,; Bartetzko, Andreas; Nierhaus, Knud H.; "Kinetic and Thermodynamic Parameters for tRNA Binding to the Ribosome and for the Translocation Reaction", The Journal of Biological Chemistry, Mar. 5, 1992, 4703-4712, vol. 267, No. 7, The American Society for Biochemistry and Molecular Biology, Inc., USA.

Wilderer, Peter A., et al.; "Modern scientific methods and their potential in wastewater science and technology"; Water Research; bearing a date of 2002; pp. 370-393; vol. 36; Elsevier Science Ltd.

Zhang, Li et al.; "Antibiotic susceptibility of mammalian mitochondrial translation"; FEBS Letters; bearing a date of 2005; pp. 6423-6427; vol. 579; Elsevier B.V.

Struthers, Mary D. et al.; "Design of a Monomeric 23-Residue Polypeptide with Defined Tertiary Structure"; Science; bearing a date of Jan. 19, 1996; pp. 342-345; vol. 271, No. 5247; American Association for the Advancement of Science; located at http://www.jstor.org/stable/2890465.

Jungbauer et al.; "Experimental and Computational Analysis of Translation Products in Apomyoglobin Expression"; J. Mol. Biol.; 2006; pp. 1121-1143; vol. 357; Elsevier Ltd.

Takahashi et al.; "Ribosome Display for Selection of Active Dihydrofolate Reductase Mutants Using Immobilized Methotrexate on Agarose Beads"; FEBS Letters; 2002; pp. 106-110; vol. 514; Elsevier Science B.V.

Excerpt from Webster's New World Medical Dictionary; "ELISA"; bearing a date of 2003; printed on Mar. 26, 2010; one page; (as provided by examinter); located at: http://www.credoreference.com/entry/webstermed/elisa.

Glaser, Ralf W.; "CBEIA: programs for simulation of ELISA experiments and affinity determination"; Journal of Immunological Methods; bearing a date of 1993; pp. 141-142; vol. 160; Elsevier Science Publishers B.V.

Marahiel et al.; "Modular Peptide Synthetases Involved in Nonribosomal Peptide Synthesis"; Chemical Reviews; bearing a date of 1997; pp. 2651-2673; vol. 97, No. 7; American Chemical Society.

Pavlov, et al.; "Synthesis of region-labelled proteins for NMR studies by in vitro translation of column-coupled mRNAs"; Biochimie; bearing a date of 1997; pp. 415-422; vol. 79; Societe francaise de biochimie et biologie moleculair; Elsevier, Paris.

U.S. Appl. No. 11/478,551, Hyde et al.

U.S. Appl. No. 11/478,550, Hyde et al.

U.S. Appl. No. 11/478,549, Hyde et al.

U.S. Appl. No. 11/478,548, Hyde et al.

U.S. Appl. No. 11/478,546, Hyde et al.

U.S. Appl. No. 11/478,540, Hyde et al.

U.S. Appl. No. 11/478,382, Hyde et al.

U.S. Appl. No. 11/478,326, Hyde et al.

U.S. Appl. No. 11/478,308, Hyde et al.

Menninger, John R.; "Computer Simulation of Ribosome Editing"; J. Mol. Biol.; 1983; pp. 383-399; vol. 171; Academic Press In. (London) Ltd.

Kelly, Mahlon; "Mainframe Graphics on a Microcomputer"; Technical Forum; Oct. 1983; pp. 439-442; BYTE Publications Inc.

* cited by examiner

Accessing the first possible dataset in response to the first input

2100 Accessing the first possible dataset in response to the first input, the first input including one or more of a target or one or more target components 2101 Accessing the first possible dataset from within a first database associated with a plurality of targets and target components 2102 Accessing the first possible dataset by associating one or more of a target and one or more target components with one or more elements of the first possible dataset 2103 Accessing the first possible dataset using a database management system engine that is configured to query a first database to retrieve the first possible dataset therefrom 2104 Accessing the first possible dataset by corresponding one or more of a target and one or more target components with one or more elements of the first possible dataset 2105 Receiving a first request associated with the first possible dataset 2106 Receiving a first request associated with the first possible dataset, the first request selecting one or more of a target or one or more target components 2107 Receiving a first request from a graphical user interface 2108 Receiving a first request from at least one submission element of a graphical user interface 2109 Receiving a first request from at least one submission element of a graphical user interface, the first request at least partially identifying one or more elements of the first possible dataset 2110 Receiving a first request from at least one submission element of a graphical user interface, the first request selecting one or more elements of the first possible dataset 2111 Receiving a first request from at least one submission element of a graphical user interface, the first request providing instructions identifying one or more of a target or one or more target components 2112 Accessing the first possible dataset in response to a first request, the first request specifying one or more of a target or one or more target components and at least one other instruction

Receiving a first input associated with a first possible dataset, the first possible dataset including data representative of one or more aspects of target synthesis

| 6100 Receiving the first input associated with the first possible dataset, the first input including data representative of one or more of amino acid incorporation into one or more peptides, biological assembler activity, nucleic acid translocation, or tRNA release | 6101 Receiving the first input associated with the first possible dataset, the first input including data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA |

| 6102 Receiving a first data entry associated with the first possible dataset | 6103 Receiving a first data entry associated with the first possible dataset, the first data entry including data representative of one or more of amino acid incorporation into one or more peptides, biological assembler activity, nucleic acid translocation, or tRNA release | 6104 Receiving a first data entry associated with the first possible dataset, the first data entry including data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA |

| 6105 Receiving a first data entry from one or more peptide synthesis units | 6106 Receiving a first data entry from one or more of one or more monitoring units, or one or more computing units | 6107 Receiving a first data entry from a graphical user interface | 6108 Receiving a first data entry from at least one submission element of a graphical user interface | 6109 Receiving a first data entry at least partially identifying one or more elements of the first possible dataset |

| 6110 Receiving a first input associated with monitoring one or more of amino acid incorporation, biological assembly activity, nucleic acid translocation, or tRNA release | 6111 Receiving the first input associated with monitoring one or more of presence or absence, concentration, or composition of one or more of one or more charge tRNA or one or more tRNA |

Accessing the first possible dataset in response to the first input

7100 Accessing the first possible dataset in response to the first input, the first input including data representative of one or more of amino acid incorporation into one or more peptides, biological assembler activity, nucleic acid translocation, or tRNA release 7101 Accessing the first possible dataset in response to the first input, the first input including data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA 7102 Accessing the first possible dataset by associating data representative of one or more of amino acid incorporation into one or more peptides, biological assembler activity, nucleic acid translocation, or tRNA release with one or more elements of the first possible dataset 7103 Accessing the first possible dataset by associating data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA with one or more elements of the first possible dataset 7104 Accessing the first possible dataset by corresponding data representative of one or more of amino acid incorporation into one or more peptides, biological assembler activity, nucleic acid translocation, or tRNA release with one or more elements of the first possible dataset 7105 Accessing the first possible dataset by corresponding data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA with one or more elements of the first possible dataset 7106 Receiving a first request associated with the first possible dataset 7107 Receiving a first request associated with the first possible dataset, the first request selecting one or more target 7108 Receiving a first request from a graphical user interface 7109 Receiving a first request from at least one submission element of a graphical user interface 7110 Receiving a first request from at least one submission element of a graphical user interface, the first request providing instructions identifying one or more target components 7111 Receiving a first request from at least one submission element of a graphical user interface, the first request specifying one or more target components and at least one other instruction

Generating the first possible dataset in response to the first input

| 8100 Generating the first possible dataset in response to the first input, the first input including data representative of one or more of amino acid incorporation into one or more peptides, biological assembler activity, nucleic acid translocation, or tRNA release | 8101 Generating the first possible dataset in response to the first input, the first input including data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA | 8102 Generating the first possible dataset by associating data representative of one or more of amino acid incorporation into one or more peptides, biological assembler activity, nucleic acid translocation, or tRNA release with one or more elements of the first possible dataset |
|---|---|---|
| 8103 Generating the first possible dataset by associating data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA with one or more elements of the first possible dataset | 8104 Generating the first possible dataset by corresponding data representative of one or more of amino acid incorporation into one or more peptides, biological assembler activity, nucleic acid translocation, or tRNA release with one or more elements of the first possible dataset | 8105 Generating the first possible dataset by corresponding data representative of one or more of availability of one or more nucleic acid codons, concentrations of one or more charged tRNA or one or more tRNA, presence or absence of one or more charged tRNA or one or more tRNA, or presence or absence of one or more anti-codons on one or more charged tRNA or one or more tRNA with one or more elements of the first possible dataset |

METHODS FOR ARBITRARY PEPTIDE SYNTHESIS

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

U.S. patent application Ser. No. 11/478,308, entitled METHODS FOR ARBITRARY PEPTIDE SYNTHESIS, naming Roderick A. Hyde; Edward K. Y. Jung and Lowell L. Wood, Jr. as inventors, filed 29, Jun., 2006.

U.S. patent application Ser. No. 11/478,549, entitled METHODS FOR ARBITRARY PEPTIDE SYNTHESIS, naming Roderick A. Hyde; Edward K. Y. Jung and Lowell L. Wood, Jr. as inventors, filed 29, Jun., 2006.

U.S. patent application Ser. No. 11/478,540, (now U.S. Pat. No. 7,754,854) entitled METHODS FOR ARBITRARY PEPTIDE SYNTHESIS, naming Roderick A. Hyde; Edward K. Y. Jung and Lowell L. Wood, Jr. as inventors, filed 29, Jun., 2006.

U.S. patent application Ser. No. 11/478,548, entitled APPARATUS FOR ARBITRARY PEPTIDE SYNTHESIS, naming Roderick A. Hyde; Edward K. Y. Jung and Lowell L. Wood, Jr. as inventors, filed 29, Jun., 2006.

U.S. patent application Ser. No. 11/478,326, entitled APPARATUS FOR ARBITRARY PEPTIDE SYNTHESIS, naming Roderick A. Hyde; Edward K. Y. Jung and Lowell L. Wood, Jr. as inventors, filed 29, Jun., 2006.

U.S. patent application Ser. No. 11/478,382, entitled APPARATUS FOR ARBITRARY PEPTIDE SYNTHESIS, naming Roderick A. Hyde; Edward K. Y. Jung and Lowell L. Wood, Jr. as inventors, filed 29, Jun., 2006.

U.S. patent application Ser. No. 11/478,550, entitled APPARATUS FOR ARBITRARY PEPTIDE SYNTHESIS, naming Roderick A. Hyde; Edward K. Y. Jung and Lowell L. Wood, Jr. as inventors, filed 29, Jun., 2006.

U.S. patent application Ser. No. 11/478,546, entitled SYSTEMS FOR ARBITRARY PEPTIDE SYNTHESIS, naming Roderick A. Hyde; Edward K. Y. Jung and Lowell L. Wood, Jr. as inventors, filed 29, Jun., 2006.

U.S. patent application Ser. No. 11/478,551, entitled SYSTEMS FOR ARBITRARY PEPTIDE SYNTHESIS, naming Roderick A. Hyde; Edward K. Y. Jung and Lowell L. Wood, Jr. as inventors, filed 29, Jun., 2006.

BRIEF DESCRIPTION OF THE FIGURES

FIG. 9 shows optional embodiments of the operational flow of FIG. 7.

FIG. 16 shows optional embodiments of the operational flow of FIG. 15.

FIG. 17 shows optional embodiments of the operational flow of FIG. 15.

FIG. 18 shows optional embodiments of the operational flow of FIG. 15.

DETAILED DESCRIPTION

Figure 1:
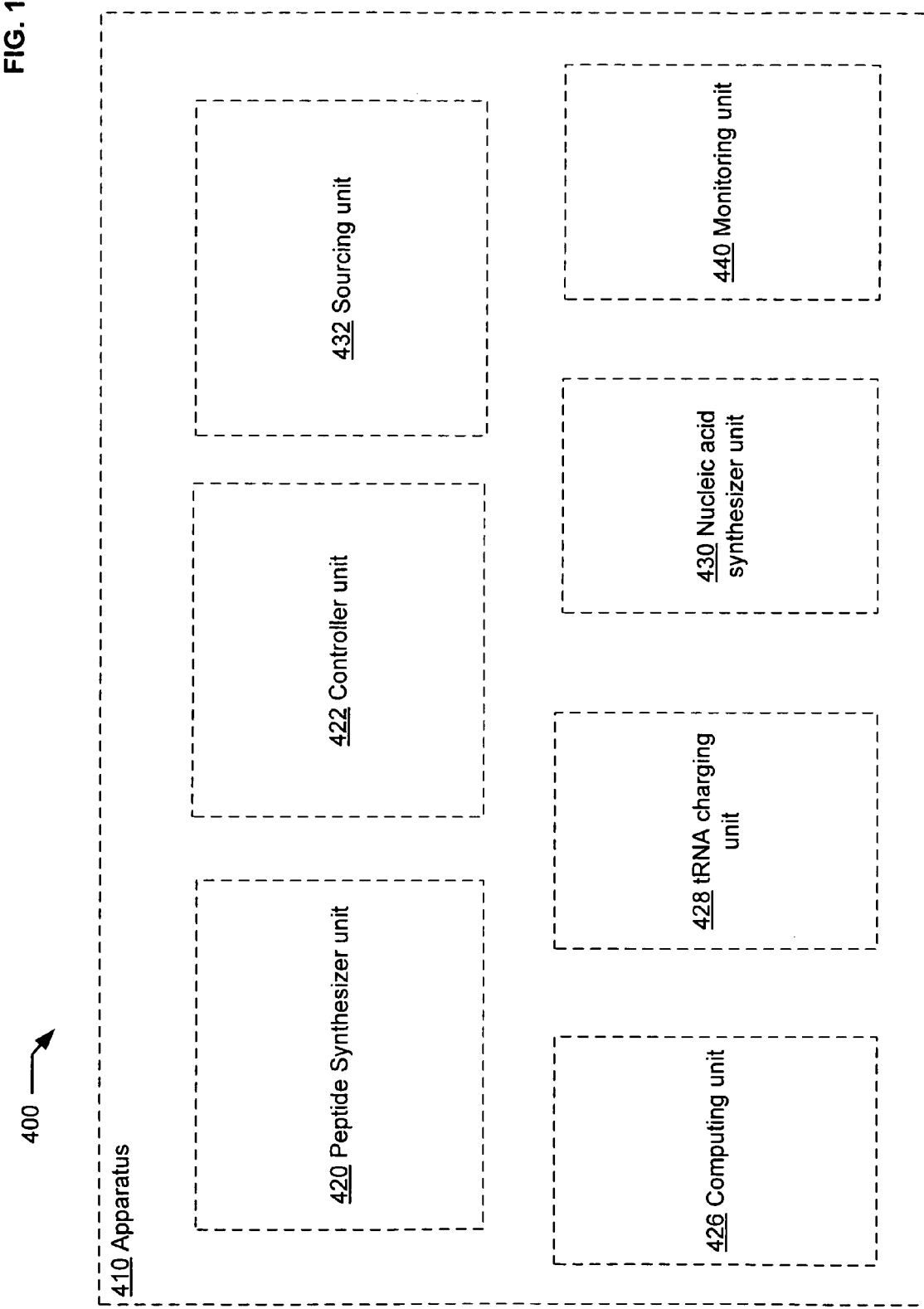
FIG. 1 shows a schematic of an illustrative apparatus in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

This disclosure is drawn, inter alia, to methods, apparatus, computer programs and computing devices related to biologically assembling and/or synthesizing peptides and/or proteins.

As used herein, the term "peptide, peptides, protein, proteins" means polypeptide molecules formed from linking various amino acids in a defined order. The link between one amino acid residue and the next forms a bond, including but not limited to an amide or peptide bond, or any other bond that can be used to join amino acids. The peptides/proteins may include any polypeptides of two or more amino acid residues. The peptides/proteins may include any polypeptides including, but not limited to, ribosomal peptides and non-ribosomal peptides. The peptides/proteins may include natural and unnatural amino acid residues. The number of amino acid residues optionally includes, but is not limited to, at least 5, 10, 25, 50, 100, 200, 500, 1,000, 2,000 or 5,000 amino acid residues. The number of amino acid residues optionally includes, but is not limited to, 2 to 5,000, 2 to 2,000, 2 to 1,000, 2 to 500, 2 to 250, 2 to 100, 2 to 50, 2 to 25, 2 to 10, 5 to 5,000, 5 to 2,000, 5 to 1,000, 5 to 500, 5 to 250, 5 to 100, 5 to 50, 10 to 5,000, 10 to 2,000, 10 to 1,000, 10 to 500, 10 to 250, to 100, or 10 to 50.

As used herein, the term "amino acid or amino acids" means any molecule that contains both amino and carboxylic acid functional groups, including, but not limited to, alpha amino acids in which the amino and carboxylate functionalities are attached to the same carbon, the so-called α-carbon. Amino acids may include natural amino acids, unnatural amino acids, and arbitrary amino acids.

As used herein, the term "natural amino acid" includes, but is not limited to, one or more of the amino acids encoded by the genetic code. The genetic codes of all known organisms encode the same 20 amino acid building blocks with the rare exception of selenocysteine and pyrolysine (Methods (2005) 36:227-238). In some embodiments, natural amino acids may also include, but not be limited to, any one or more of the amino acids found in nature. In some embodiments, these natural amino acids may include, but not be limited to, amino acids from one or more of plants, microorganisms, prokaryotes, eukaryotes, protozoa or bacteria. In some embodiments, natural amino acids may include, but are not limited to, amino acids from one or more of mammals, yeast, *Escherichia coli*, or humans.

As used herein, the term "unnatural amino acid" may include any amino acid other than the amino acids encoded by the genetic code. In some embodiments, unnatural amino acids may include, but not be limited to, modified or derivatized amino acids encoded by the genetic code. In some embodiments, unnatural amino acids may include, but not be limited to, modified or derivatized amino acids of any one or more of the amino acids found in nature. In some embodiments, unnatural amino acids may include, but not be limited to, modified or derivatized amino acids from one or more of plants, microorganisms, prokaryotes, eukaryotes, protozoa, bacteria, mammals, yeast, *E. coli*, or humans.

Unnatural amino acids are known in the art including, but not limited to, those containing spectroscopic probes, post-translational modification, metal chelators, photoaffinity labels, D-enantiomers, as well as other functional groups and modified structures (e.g. Methods 36 (2005) 227-238; Annu. Rev. Biochem. (2004) 73:147-176; Science (2003) 301:964-967; Royal Society of Chemistry (2004) 33:422-430).

As used herein, the term "arbitrary amino acid or arbitrary amino acids" means any amino acid that is not the amino acid coded for by the tRNA codon recognition site as determined by the genetic code. In some embodiments, arbitrary amino acids are natural or unnatural amino acids.

As used herein, the term "amino acid residue or amino acid residues" means the remainder of an amino acid incorporated into a peptide/protein.

As used herein, the term "tRNA, tRNAs, transfer RNA or transfer RNAs" means an RNA chain that transfers an amino acid to a growing polypeptide chain. The tRNA has sites for amino acid attachment and codon recognition. In some embodiments, tRNA includes natural, unnatural, and arbitrary tRNA.

As used herein, the term "natural tRNA" means one or more tRNA known in nature that transfer an amino acid to a growing polypeptide chain. In some embodiments, natural tRNA includes, but is not limited to, tRNA that transfer one or more of the natural amino acids that are encoded by the genetic code. In some embodiments, natural tRNA include, but are not limited to, natural tRNA from one or more of plants, microorganisms, prokaryotes, eukaryotes, protozoa, bacteria, mammals, yeast, *E. coli*, humans, or archae.

As used herein, the term "unnatural tRNA" means any tRNA, other than tRNA known in nature, which transfers an amino acid to a growing polypeptide chain. In some embodiments, unnatural tRNA may include, but are not limited to, modified or derivatized natural tRNA. In some embodiments, unnatural tRNA may include, but are not limited to, modified or derivatized natural tRNA from one or more of plants, microorganisms, prokaryotes, eukaryotes, protozoa, bacteria, mammals, yeast, *E. coli*, humans, or archae. In some embodiments, unnatural tRNA may include, but are not limited to, tRNA with altered sites for amino acid attachment, and/or tRNA with altered acceptor stems, and/or tRNA with altered sites for codon recognition (the anticodon). In some embodiments, unnatural tRNA is recombinant tRNA.

As used herein, the term "arbitrary tRNA" means a tRNA that has been modified or derivatized such that the amino acid attachment site may bind one or more amino acids other than the amino acid specified by the codon recognition site based on the genetic code. The amino acid may be natural or unnatural. Arbitrary tRNA may also include tRNA that have been modified or derivatized such that the amino acid attachment site may bind one or more different amino acids (natural or unnatural), while the codon recognition site may recognize one or more of one or more stop codons, one or more singlet codons, one or more doublet codons, one or more triplet codons, one or more quadruplet codons, one or more quintuplet codons, one or more sextuplet codons or others. Stop codons include ochre (TAA), amber (TAG and opal (TGA).

Methods for modifying tRNA including, but not limited to, the anti-codon, the amino acid attachment site, and/or the accepter stem to allow incorporation of unnatural and/or arbitrary amino acids are known in the art (Methods (2005) 36:227-238 Methods (2005) 36:270-278; Annu. Rev. Biochem. (2004) 73:147-176; Nucleic Acids Research (2004) 32:6200-6211 PNAS (2003) 100:6353-6357; Royal Society of Chemistry (2004) 33:422-430).

As used herein, the term "anti-stop codon tRNA" means a tRNA having a stop codon recognition site. In some embodiments, the anti-stop codon tRNA may be charged with one or more natural, one or more unnatural, or one or more arbitrary amino acids. In some embodiments, the anti-stop codon tRNA may be a natural, an unnatural, or an arbitrary tRNA.

As used herein, the term "charged tRNA or charged tRNAs" means tRNA that has an amino acid bound at the amino acid attachment site. During peptide synthesis, the aminoacyl group is transferred to the nascent peptide, releasing the tRNA. As used herein, the term "released tRNA"

means the tRNA remaining after the charged tRNA has donated the attached amino acid to the nascent polypeptide. In some embodiments, the charged tRNA may be natural, unnatural and/or arbitrary.

As used herein, the term "natural charged tRNA" means a natural tRNA that has an amino acid bound at the amino acid attachment site. In some embodiments, the natural tRNA has one or more of a natural or an unnatural amino acid bound at the amino acid attachment site.

As used herein, the term "unnatural charged tRNA" means an unnatural tRNA that has an amino acid bound at the amino acid attachment site. In some embodiments, the unnatural tRNA has one or more of a natural or an unnatural amino acid bound at the amino acid attachment site.

As used herein, the term "arbitrary charged tRNA or tRNA charged with arbitrary amino acids" means a tRNA that has an amino acid bound at the amino acid attachment site, and that amino acid is different from the amino acid specified by the codon recognition site of the tRNA based on the genetic code. In some embodiments, the bound amino acid is a natural or an unnatural amino acid. In some embodiments, the codon recognition site includes, but is not limited to, a stop codon recognition site, a singlet codon recognition site, a doublet codon recognition site, a triplet codon recognition site, a quadruplet codon recognition site, a quintuplet codon recognition site, or a sextuplet codon recognition site.

As used herein, the term "charging or aminoacylation" is a process of adding an aminoacyl group to a compound. Methods for charging natural, unnatural and/or arbitrary tRNA with natural, unnatural and/or arbitrary amino acids are known in the art, and include, but are not limited to, chemical aminoacylation, biological misacylation, acylation by modified aminoacyl tRNA synthetases, ribozyme-based, and protein nucleic acid-mediated methods (Methods (2005) 36:227-238; Methods (2005) 36:39-244; Methods (2005) 36:245-251; Methods (2005) 36:270-278; Methods (2005) 36:291-298; Annu. Rev. Biochem. (2004) 73:147-176; Nucleic Acids Research (2004) 32:6200-6211; Royal Society of Chemistry (2004) 33:422-430); Nature (2002) 20:723-728.

As used herein, the term "aminoacyl tRNA synthetase or aaRs" means an enzyme that catalyzes the binding of one or more amino acids to a tRNA to form an aminoacyl-tRNA (or charged tRNA). In some embodiments, the synthetase binds the appropriate amino acid to one or more tRNA molecules. In some embodiments, the synthetase mediates a proofreading reaction to ensure high fidelity of tRNA charging. In some embodiments, the synthetase does not mediate a proofreading reaction to ensure high fidelity of tRNA charging.

As used herein, the term "natural aminoacyl tRNA synthetases" means aminoacyl tRNA synthetases known in nature that add an aminoacyl group to a tRNA. In some embodiments, natural aminoacyl tRNA synthetases include, but are not limited to, aminoacyl tRNA synthetases that add one or more of the natural aminoacyl groups that are encoded by the genetic code. In some embodiments, natural aminoacyl tRNA synthetases include, but are not limited to, natural aminoacyl tRNA synthetases from one or more of plants, microorganisms, prokaryotes, eukaryotes, protozoa, bacteria, mammals, yeast, *Escherichia coli*, or humans.

The term "unnatural aminoacyl tRNA synthetase" means any aminoacyl tRNA synthetase, other than aminoacyl tRNA synthetases known in nature that add an aminoacyl group to a tRNA. In some embodiments, unnatural aminoacyl tRNA synthetases may include, but are not limited to, modified or derivatized natural aminoacyl tRNA synthetases. In some embodiments, unnatural aminoacyl tRNA synthetases may include, but are not limited to, modified or derivatized natural aminoacyl tRNA synthetases from one or more of plants, animals, microorganisms, prokaryotes, eukaryotes, protozoa, bacteria, mammals, yeast, *E. coli*, or humans. In some embodiments, unnatural aminoacyl tRNA synthetases may include, but are not limited to, aminoacyl tRNA synthetases with altered aminoacyl specificity and/or altered tRNA specificity, and/or altered editing ability As used herein, the term "altered specificity" means that the specificity typically observed in nature has been changed. In some embodiments, altered specificity includes, but is not limited to, broadening the specificity to include, for example, recognition of additional amino acids, and/or additional tRNA. In some embodiments, altered specificity includes, but is not limited to, changing the identity of the aminoacyl group and/or tRNA from the aminoacyl group and/or tRNA recognized in nature.

Modified aminoacyl tRNA synthetases are known in the art, and include but are not limited to, aminoacyl tRNA synthetases with relaxed substrate specificity through active site mutations as well as aminoacyl tRNA synthetases with attenuated proofreading activity (e.g. Methods (2005) 36:227-238; Methods (2005) 36:291-298; Annu. Rev. Biochem. (2004) 73:147-176; Science (2003) 301:964-967; Microbiology and Molecular Biology Reviews (2000) 64:202-236).

As used herein, the term "biological assembler or biological assemblers" means any mechanism that utilizes one or more biological components to synthesize one or more peptides/proteins. In some embodiments, biological assemblers are peptide/protein assemblers. In some embodiments, biological assemblers are partially or completely isolated, purified, or separated from cells, other cellular material, and/or tissues. In some embodiments, biological assemblers are encompassed by a semi-permeable membrane and/or membrane-bound. In some embodiments, biological assemblers are modified, non-natural or recombinant. In some embodiments, biological assemblers include, but are not limited to, one or more of ribosome-based assemblers and nonribosome-based assemblers.

As used herein, the term "ribosome-based assemblers" means biological assemblers that include, but are not limited to, one or more ribosomes. The ribosomes may be one or more of eukaryotic ribosomes and/or prokaryotic ribosomes. In some embodiments, the ribosome-based assemblers are partially or completely isolated, purified, or separated from cells, other cellular material, and/or tissues. In some embodiments, the ribosomes are from mitochondria and/or chloroplasts. The ribosomes may be from one or more of plants, animals, microorganisms, prokaryotes, eukaryotes, protozoa, bacteria, mammals, yeast, *E. coli*, and/or humans.

As used herein, the term "nonribosome-based assemblers" means biological assemblers that do not include ribosomes. In some embodiments, the nonribosome-based assemblers use one or more elements of a modular enzyme complex in which there is a common core structure, and optionally include one or more different modules to perform additional manipulations on the evolving product. In some embodiments, the nonribosome-based assemblers are partially or completely isolated, purified, or separated from one or more of one or more unicellular organisms, one or more plants, or one or more fungi.

As used herein, the term "biological assembler components or components of the biological assemblers" means one or more biological elements, and/or one or more non-biological elements, that make up the biological assemblers. In some embodiments, the components of one or more biological assemblers include, but are not limited to, one or more of one or more ribosomes, one or more ribosome subunits, one or more ribosomal RNA (rRNA) molecules, one or more protein molecules, one or more translation factors, one or more enzymes, one or more energy sources or one or more molecular chaperones. In some embodiments, biological assembler components include, but are not limited to, one or more of one or more elements of a modular enzyme complex or one or more additional enzyme modules. In some embodiments, the components include, but are not limited to, one or more of one or more prokaryotic components, one or more eukaryotic components, one or more mitochondrial components, and/or one or more chloroplastic components.

Methods of partially and/or completely purifying or isolating natural, non-natural, and/or recombinant components of biological assemblers, including both ribosomal and non-ribosomal components, and re-assembling functional peptide/protein synthetic machinery are known in the art (e.g. Methods (2005) 36:279-290; Methods (2005) 36:299-304; PNAS (2003) 100:6353-6357; Nature (2001) 19:751-755; Royal Society of Chemistry (2004) 33:422-430). Methods for partially or completely encapsulating isolated and/or purified biological assemblers and/or biological assembler components within natural or artificial semi-permeable membranes, or partially or completely integrating isolated and/or purified biological assemblers and/or biological assembler components within natural or artificial semi-permeable membranes are known in the art (e.g. Cell (1997) 89:523-533; J. Cell Biology (1973) 56:191-205; J. Biol. Chem. (2000) 43:33820-33827).

As used herein, the term "components of peptide and/or target synthesis" or "peptide and/or target synthesis components" or the equivalent means one or more biological components that may be optionally included in one or more of the aspects described herein. As an example, peptide synthesis components may include, but are not limited to, one or more biological assemblers, one or more biological assembler components, one or more charged tRNA, and/or one or more nucleic acids. Peptide synthesis components may also include, but are not limited to, one or more tRNA, one or more amino acids, one or more tRNA charging components, one or more nucleic acids, and one or more nucleic acid charging components.

In one aspect, the disclosure is drawn to methods for peptide synthesis. Some methods comprise sequentially providing two or more charged tRNA to one or more identifiable locations. Some methods comprise co-localizing sequentially two or more charged tRNA with one or more biological assemblers. Some methods comprise co-localizing sequentially one or more biological assemblers with two or more charged tRNA, wherein at least two of the two or more tRNA are located at one or more different locations. Some methods comprise assembling a target peptide by co-localizing sequentially one or more biological assemblers and two or more charged tRNA.

In some embodiments, one or more methods include synthesizing a target peptide by providing two or more charged tRNA to one or more identifiable locations. In some embodiments, one or more methods include synthesizing a target peptide by co-localizing sequentially two or more charged tRNA with one or more biological assemblers. In some embodiments, one or more methods include synthesizing a target peptide by co-localizing sequentially one or more biological assemblers with two or more charged tRNA, wherein at least two of the two or more charged tRNA are at one or more different locations.

Some embodiments include one or more methods of extra-cellular peptide synthesis comprising co-localizing sequentially two or more charged tRNA with one or more biological assemblers in vitro. Some embodiments include one or more methods of extra-cellular peptide synthesis comprising sequentially providing two or more charged tRNA to one or more identifiable locations at one or more first identifiable time intervals in vitro. Some embodiments include one or more methods of extra-cellular peptide synthesis comprising co-localizing sequentially one or more biological assemblers with two or more charged tRNA, wherein at least two of the two or more charged tRNA are located at one or more different locations in vitro. Some embodiments include one or more methods of extra-cellular peptide synthesis comprising assembling a target peptide in vitro by co-localizing sequentially one or more biological assemblers, and two or more charged tRNA. In some embodiments, the one or more methods are cell-free.

In some embodiments, one or more methods include determining and/or selecting an assembly order; and co-localizing two or more charged tRNA with one or more biological assemblers based on the assembly order. In some embodiments, one or more methods include determining and/or selecting an assembly order; and providing two or more charged tRNA to one or more identifiable locations at one or more first identifiable time intervals based on the assembly order. In some embodiments, one or more methods include determining and/or selecting an assembly order; and co-localizing one or more biological assemblers with two or more charged tRNA based on the assembly order, wherein at least two of the two or more charged tRNA are located at one or more different locations. In some embodiments, one or more methods include determining and/or selecting an assembly order; and assembling a target peptide by co-localizing one or more biological assemblers, and two or more charged tRNA.

As used herein, the term "assembly order" means the process (or sequence) by which the one or more components of target peptide synthesis are provided and/or co-localized and then optionally removed and/or separated.

In some embodiments, one or more methods further comprise eliminating and/or removing and/or separating, optionally sequentially, one or more components of peptide synthesis, optionally including, but not limited to, one or more biological assemblers, one or more nucleic acids, one or more biological assembler components, one or more charged tRNA, and/or one or more tRNA. In some embodiments, one or more methods further comprise consuming, optionally sequentially, two or more charged tRNA. In some embodiments, one or more methods further comprise eliminating and/or removing and/or separating, optionally sequentially, two or more charged tRNA and/or one or more released tRNA. In some embodiments, one or more methods further include separating, optionally sequentially, one or more biological assemblers from two or more charged tRNA and/or one or more released tRNA, wherein at least two of the two or more charged tRNA and/or released tRNA are located at one or more different locations. In some embodiments, one or more methods further include separating, optionally sequentially, one or more biological assemblers and two or more charged tRNA and/or one or more released tRNA.

As used herein, the term "co-localizing or providing or assembling" means any process resulting in one or more components being in the same place at the same time. By "in the same place at the same time" is meant physical proximity such that the one or more components are capable of interaction on a molecular level. Co-localizing may include, commingling, combining, mixing, assembling, aggregating, injecting, or other similar processes.

As used herein, the term "synthesizing" means any process resulting in one or more components being combined and/or added to a prior component. For example, a process that results in combining two or more amino acids to form a peptide, or a process that results in combining two or more nucleotides to form a nucleic acid.

As used herein, the term "removing or eliminating or separating" means one or more processes that result in one or more peptide synthesis components being no longer located in the same place. In some embodiments, one or more peptide synthesis components are at least partially removed and/or eliminated and/or consumed and/or separated. In some embodiments, one or more components are moved to another location.

In illustrative embodiments, charged tRNA are at least partially consumed when the attached amino acid is donated to the nascent polypeptide. In some embodiments, charged tRNA not incorporated into the nascent polypeptide may be partially or completely removed (and/or separated and/or eliminated) from one or more locations. In some embodiments, tRNA remaining after the previously attached amino acid is donated to the nascent polypeptide are partially or completely removed and/or eliminated from one or more locations. In illustrative embodiments, one or more charged tRNA and/or one or more tRNA are separated from one or more biological assemblers. In illustrative embodiments, one or more biological assemblers are separated from one or more charged tRNA and/or one or more tRNA. In illustrative embodiments, one or more biological assemblers are removed from one or more locations.

As used herein, the term "sequentially" when modifying processes, such as, the processes including, for example, co-localizing, providing, removing, and/or eliminating, means any process that includes a temporal aspect such that the process acts upon one or more components at subsequent times. Sequentially may include, but is not limited to, any process that acts upon one or more components in a defined order. Sequentially may include, but is not limited to, any process that acts on one or more components one after another.

Generic processes useful for co-localizing, providing, eliminating, removing, separating and/or assembling, and including sequential processes, are known in the art and include, but are not limited to, one or more of automated methods, mechanical methods, computer and/or software-controlled methods, and fluid flow. Fluid flow includes, but is not limited to, nanofluidics and microfluidics. Nanofluidics and microfluidics include, but are not limited to, continuous flow microfluidics and digital microfluidics, and have been developed for use in biological systems (Annu. Rev. Fluid Mech. (2004) 36:381-411; Annu. Rev. Biomed. Eng. (2002) 4:261-86; Science (1988) 242:1162-1164, Rev. Mod. Phys. (2005) 77:977-1026).

In illustrative embodiments, fluid flow is used to "flow" charged tRNA into association (co-localization) with biological assemblers and to "flow" excess charged tRNA and/or released tRNA out of association (co-localization) with biological assemblers. In illustrative embodiments, fluid flow is used to sequentially "flow" one type of charged tRNA after another into association with biological assemblers and to sequentially "flow" one type of excess charged tRNA and/or released tRNA after another out of association with biological assemblers. In illustrative embodiments, fluid flow is used to "flow" biological assemblers into association (co-localization) with charged tRNA and to "flow" biological assemblers away from excess charged tRNA and/or released tRNA. In illustrative embodiments, fluid flow is used to sequentially "flow" one or more biological assemblers to locations containing one type of charged tRNA after another and to sequentially "flow" biological assemblers away from one type of excess charged tRNA and/or released tRNA after another.

In illustrative embodiments, one or more charged tRNA are provided in the order of a target peptide sequence with each subsequent charged tRNA being provided after the aminoacyl residue from the prior charged tRNA is incorporated into a nascent polypeptide. In illustrative embodiments, excess charged tRNA and/or released tRNA are removed/eliminated/separated before subsequent charged tRNA are provided.

In illustrative embodiments, one or more biological assemblers are co-localized with one or more charged tRNA in the order of a target peptide sequence with each subsequent co-localization occurring after the aminoacyl residue from the prior charged tRNA is incorporated into a nascent polypeptide. In illustrative embodiments, biological assemblers are removed/separated from excess charged tRNA and/or released tRNA prior to co-localization with subsequent charged tRNA.

In some embodiments, one or more methods includes co-localizing and/or providing and/or assembling, optionally sequentially, one or more peptide synthesis components at one or more identifiable time intervals. In some embodiments, one or more methods include providing, optionally sequentially, two or more charged tRNA to one or more identifiable locations at one or more first identifiable time intervals. In some embodiments, one or more methods include co-localizing, optionally sequentially, two or more charged tRNA with one or more biological assemblers at one or more first identifiable time intervals. In some embodiments, one or more methods include co-localizing sequentially one or more biological assemblers with two or more charged tRNA at one or more first identifiable time intervals, wherein at least two of the two or more charged tRNA are located at one or more different locations. In some embodiments, one or more methods include assembling a target peptide by co-localizing sequentially one or more biological assemblers and two or more charged tRNA at one or more first identifiable time intervals.

In some embodiments, one or more methods further include separating and/or removing and/or eliminating and/or consuming, optionally sequentially, one or more peptide synthesis components at one or more identifiable time intervals. In some embodiments, one or more methods further include removing and/or separating, optionally sequentially, two or more charged tRNA and/or one or more released tRNA from one or more biological assemblers at one or more second identifiable time intervals. In some embodiments, one or more methods further include separating, optionally sequentially, one or more biological assemblers from two or more charged tRNA and/or one or more released tRNA at one or more second identifiable time intervals, wherein at least two of the two or more charged tRNA and/or released tRNA are located at one or more different locations. In some embodiments, one or more methods further include assembling a target peptide by separating, optionally sequentially, one or more biological assemblers and two or more charged tRNA and/or the released tRNA at one or more second identifiable time intervals.

As used herein, the term "identifiable time interval" means a discrete amount of time that is optionally knowable, determinable, and/or calculable. The term "one or more identifiable time intervals", is used herein to indicate time intervals for one or more processes. The one or more identifiable time intervals may be the same or different for different processes and/or elements of processes. The one or more identifiable time intervals may be the same or different for synthesis of different target peptides. One of skill in the art is able to determine appropriate one or more identifiable time intervals based on the teachings herein and in the art. The one or more identifiable time intervals may be designated "first", "second", "third", "fourth", "fifth", "sixth", "seventh", "eighth", "ninth", "tenth", and so on for clarity to indicate that the time interval may, or may not, be the same as other time intervals. Labeling one or more time intervals with the same numeral may indicate the same or similar time intervals unless context indicates otherwise.

In some embodiments, one or more identifiable time intervals are at least partially based on a predicted rate of incorporation of two or more amino acids into one or more peptides. In some embodiments, one or more identifiable time intervals are at least partially based on a predicted rate of activity of one or more biological assemblers. In some embodiments, one or more identifiable time intervals are at least partially based on a predicted rate of translocation of one or more nucleic acids. In some embodiments, one or more identifiable time intervals are at least partially based on a predicted rate of release of tRNA.

In some embodiments, one or more first identifiable time intervals and/or one or more second identifiable time intervals are from approximately 0.001 seconds to approximately 0.1 seconds. In some embodiments, one or more first identifiable time intervals and/or one or more second identifiable time intervals are approximately 0.01 seconds.

Many aspects of biological peptide synthesis, both in cells and in cell-free systems, have been studied using a variety of natural and unnatural components (Cell (2002) 108:557-572, Ann. Rev. Biochem. (2004) 73:657-704, Methods (2005) 36:279-290, Methods (2005) 36:299-304), and provide a basis for predicting appropriate time intervals for addition and removal of target components for peptide synthesis. Rates of incorporation of a variety of natural, unnatural, and arbitrary amino acids into nascent peptides are known in the art for a variety of biological systems, including but not limited to, eukaryotic and prokaryotic systems. The corresponding rate of release of the tRNA following incorporation of the amino acyl residue has also been studied. The rate of activity of a variety of eukaryotic and prokaryotic cells and cell-free systems for peptide synthesis is known in the art (Molecular Biology of the Cell (2002) 343-344, J. Mol. Biol. (1984):549-576, J. Mol. Biol. (1989) 209:65-77, Methods (2005) 36:279-290). The rate of translocation of nucleic acids in these systems has also been studied. The rate of in vivo ribosomal incorporation of amino acids into a protein is primarily limited by elongation (dominated by acquisition rate of the cognate charged tRNA) and (for polyribosomal translation) by ribosomal initiation (Genetics (1998) 149:37-44; Journal of Theoretical Biology (2006) 239:417-434).

In some embodiments, one or more identifiable time intervals may include from approximately 0.001 seconds to approximately 0.1 seconds. In one or more embodiments, one or more identifiable time intervals may include, but are not limited to, from 0.001 to 0.1, from 0.005 to 0.1, from 0.01 to 0.1, from 0.05 to 0.1, from 0.001 to 0.05, from 0.001 to 0.01, and from 0.001 to 0.005 seconds. In some embodiments, one or more identifiable time intervals may include approximately 0.01 seconds. In some embodiments, one or more identifiable time intervals may include, but are not limited to, approximately 0.001, 0.005, 0.01, 0.05, and 0.1 seconds.

In some illustrative embodiments, charged tRNA may be "flowed" at predetermined time intervals. One or more of the time intervals may be of the same length, of different lengths, of arbitrary lengths, of random lengths, of variable lengths, of fixed lengths, and/or of sequential lengths. In some embodiments, the time interval is determined, partially or completely, by the length of time needed and/or useful to incorporate each additional amino acid residue into the nascent polypeptide, and/or by the length of time needed and/or useful to remove excess charged tRNA and/or released tRNA from association (co-localization) with the ribosomal assemblers. In some embodiments, the time interval is determined, partially or completely, by internal and/or external feedback. In some embodiments, the internal and/or external feedback is partially or completely, related to the length of time needed to incorporate each additional amino acid residue into the nascent polypeptide and/or by the length of time needed and/or useful to remove excess charged tRNA and/or released tRNA from association (co-localization) with the ribosomal assemblers.

In some embodiments, one or more methods may further include, monitoring amino acid incorporation into one or more peptides, biological assembler activity, nucleic acid translocation, and/or tRNA release. In some embodiments, one or more methods further include, monitoring presence or absence, concentration, and/or composition of charged tRNA and/or tRNA.

Methods for measuring and/or monitoring amino acid incorporation into one or more peptides, biological assembler activity, nucleic acid translocation, or tRNA release are known in the art and include, but are not limited to spectroscopy, fluorescence spectroscopy, surface plasmon resonance imaging, nuclear magnetic resonance imaging, and/or immunoassays. Methods for measuring presence or absence, concentration, and/or compositions of charged tRNA or tRNA are known in the art, and include, but are not limited to, spectroscopy, fluorescence spectroscopy, surface plasmon resonance imaging, nuclear magnetic resonance imaging, and/or immunoassays.

In some embodiments, one or more methods may include co-localizing and/or providing and/or assembling, optionally sequentially, one or more peptide synthesis components at one or more identifiable time intervals, wherein the one or more identifiable time intervals are at least partially based on measurements of amino acid incorporation into one or more peptides, biological assembler activity, nucleic acid translocation, and/or tRNA release. In some embodiments, the one or more identifiable time intervals are at least partially based on measurements of availability of one or more nucleic acid codons.

In some embodiments, one or more methods include providing, optionally sequentially, two or more charged tRNA to one or more identifiable locations at one or more first identifiable time intervals, wherein the one or more first identifiable time intervals are at least partially based on, but are not limited to, amino acid incorporation into one or more peptides, biological assembler activity, nucleic acid translocation, and/or tRNA release. In some embodiments, one or more methods include co-localizing sequentially two or more charged tRNA with one or more biological assemblers at one or more first identifiable time intervals, wherein the one or more first identifiable time intervals are at least partially based on, but are not limited to, amino acid incorporation into one or more peptides, biological assembler activity, nucleic acid translocation, and/or tRNA release. In some embodiments, one or more methods include co-localizing sequentially one or more biological assemblers with two or more charged tRNA at one or more first identifiable time intervals, wherein at least two of the two or more charged tRNA are located at one or more different locations, and wherein the one or more first identifiable time intervals are at least partially based on, but are not limited to, amino acid incorporation into one or more peptides, biological assembler activity, nucleic acid translocation, and/or tRNA release. In some embodiments, one or more methods include assembling a target peptide by co-localizing sequentially one or more biological assemblers with two or more charged tRNA at one or more first identifiable time intervals, and wherein the one or more first identifiable time intervals are at least partially based on, but are not limited to, amino acid incorporation into one or more peptides, biological assembler activity, nucleic acid translocation, and/or tRNA release. In some embodiments, the one or more first identifiable time intervals are at least partially based on measurements of availability of one or more nucleic acid codons.

In some embodiments, one or more methods may include removing and/or separating and/or consuming and/or eliminating, optionally sequentially, one or more peptide synthesis components at one or more identifiable time intervals, wherein the one or more identifiable time intervals are at least partially based on measurements and/or monitoring of amino acid incorporation into one or more peptides, biological assembler activity, nucleic acid translocation, and/or tRNA release. In some embodiments, the one or more identifiable time intervals are at least partially based on measurements and/or monitoring of availability of one or more nucleic acid codons.

In some embodiments, one or more methods further include removing and/or separating, optionally sequentially, two or more charged tRNA and/or one or more tRNA from one or more biological assemblers at one or more second identifiable time intervals, wherein the one or more second identifiable time intervals are at least partially based on, but are not limited to, amino acid incorporation into one or more peptides, biological assembler activity, nucleic acid translocation, and/or tRNA release. In some embodiments, one or more methods further include removing and/or separating one or more biological assemblers from two or more charged tRNA and/or one or more tRNA at one or more second identifiable time intervals, wherein the two or more charged tRNA are located at one or more different locations, and wherein the one or more second identifiable time intervals are at least partially based on, but are not limited to, amino acid incorporation into one or more peptides, biological assembler activity, nucleic acid translocation, and/or tRNA release. In some embodiments, one or more methods further include removing and/or separating one or more biological assemblers and two or more charged tRNA and/or one or more tRNA at one or more second identifiable time intervals, and wherein the one or more second identifiable time intervals are at least partially based on, but are not limited to, amino acid incorporation into one or more peptides, biological assembler activity, nucleic acid translocation, and/or tRNA release. In some embodiments, the one or more second identifiable time intervals are at least partially based on measurements of availability of one or more nucleic acid codons.

In some embodiments, one or more methods may include co-localizing and/or providing and/or assembling, optionally sequentially, one or more peptide synthesis components at one or more identifiable time intervals, wherein the one or more identifiable time intervals are at least partially based on measurements of concentrations of charged tRNA and/or released tRNA. In some embodiments, the one or more identifiable time intervals are at least partially based on measurements of presence or absence of one or more charged tRNA and/or one or more tRNA. In some embodiments, the one or more identifiable time intervals are at least partially based on measurements of presence or absence of one or more anti-codons on one or more charged tRNA and/or one or more tRNA.

In some embodiments, one or more methods include providing, optionally sequentially, two or more charged tRNA at one or more identifiable locations at one or more first identifiable time intervals, wherein the one or more first identifiable time intervals are at least partially based on measurements of concentrations of, presence or absence of, and/or composition of one or more charged tRNA and/or one or more released tRNA. In some embodiments, one or more methods include co-localizing sequentially two or more charged tRNA with one or more biological assemblers at one or more first identifiable time intervals, wherein the one or more first identifiable time intervals are at least partially based on measurements of concentrations of, presence or absence of, and/or composition of one or more charged tRNA and/or one or more released tRNA. In some embodiments, one or more methods include co-localizing sequentially one or more biological assemblers with two or more charged tRNA at one or more first identifiable time intervals, wherein at least two of the two or more charged tRNA are located at one or more different locations, and wherein the one or more first identifiable time intervals are at least partially based on measurements of concentrations of, presence or absence of, and/or composition of one or more charged tRNA and/or one or more released tRNA. In some embodiments, one or more methods include assembling a target peptide by co-localizing sequentially one or more biological assemblers with two or more charged tRNA at one or more first identifiable time intervals, and wherein the one or more first identifiable time intervals are at least partially based on measurements of concentrations of, presence or absence of, and/or composition of one or more charged tRNA and/or one or more released tRNA. In some embodiments, the one or more first identifiable time intervals are at least partially based on the presence or absence of one or more anti-codons on one or more charged tRNA and/or released tRNA.

In some embodiments, one or more methods may further include removing and/or separating and/or consuming and/or eliminating, optionally sequentially, one or more peptide synthesis components at one or more identifiable time intervals, wherein the one or more identifiable time intervals are at least partially based on measurements of concentrations of charged tRNA or released tRNA. In some embodiments, the one or more identifiable time intervals are at least partially based on measurements of presence or absence of one or more of the two or more charged tRNA or of the one or more tRNA. In some embodiments, the one or more identifiable time intervals are at least partially based on measurements of presence or absence of one or more anti-codons on one or more of the two or more charged tRNA or the one or more tRNA.

In some embodiments, one or more methods further include removing and/or separating, optionally sequentially, one or more charged tRNA and/or one or more tRNA from one or more biological assemblers at one or more second identifiable time intervals, wherein the one or more second identifiable time intervals are at least partially based on measurements of concentrations of, presence or absence of, and/or composition of one or more charged tRNA and/or released tRNA. In some embodiments, one or more methods further include removing and/or separating, optionally sequentially, one or more biological assemblers from two or more charged tRNA at one or more second identifiable time intervals, wherein at least two of the two or more charged tRNA are located at one or more different locations, and wherein the one or more second identifiable time intervals are at least partially based on measurements of concentrations of, presence or absence of, and/or composition of one or more charged tRNA and/or released tRNA. In some embodiments, one or more methods further include separating, optionally sequentially, one or more biological assemblers and two or more charged tRNA at one or more second identifiable time intervals, and wherein the one or more second identifiable time intervals are at least partially based on measurements of concentrations of, presence or absence of, and/or composition of one or more charged tRNA and/or released tRNA. In some embodiments, the one or more second identifiable time intervals are at least partially based on the presence or absence of one or more anti-codons on one or more charged tRNA and/or released tRNA.

In some embodiments, one or more methods may include one or more identifiable time intervals. Such identifiable time intervals may include for example, but are not limited to, one or more of one or more first identifiable time intervals, one or more second identifiable time intervals, one or more third identifiable time intervals, one or more fourth identifiable time intervals, one or more fifth identifiable time intervals, and/or one or more sixth identifiable time intervals. In some embodiments, one or more identifiable time intervals may be the same as one or more other identifiable time intervals. In some embodiments, one or more of identifiable time intervals may be different from one or more other identifiable time intervals. In some embodiments, each identifiable time interval is determined separately.

In illustrative embodiments, one or more methods may include a first identifiable time interval for the (optionally sequential) co-localization of biological assemblers and charged tRNA. The one or more methods may also include a second identifiable time interval for the removal and/or separation (optionally sequential) of the biological assemblers from charged tRNA. These time intervals may be the same or different.

In illustrative embodiments, one or more methods may include a first identifiable time interval for the (optionally sequential) co-localization of charged tRNA with biological assemblers. The one or more methods may also include a second identifiable time interval for the removal and/or separation (optionally sequential) of the charged tRNA from the biological assemblers. These time intervals may be the same or different. The one or more methods may also include a third/fourth/fifth identifiable time interval for the co-localization of the biological assemblers and/or biological assembler components and/or nucleic acids, for example, at an identifiable location. These time intervals may all be the same as each other, or one or more may be different. In some embodiments, one or more of these time intervals will be different from the first and/or second identifiable time intervals.

In some embodiments, one or more methods include providing and/or co-localizing two or more charged tRNA, wherein two or more of the two or more charged tRNA have the same anti-codon and are optionally charged with different amino acids. In some embodiments, one or more methods include providing and/or co-localizing two or more charged tRNA, wherein two or more of the two or more charged tRNA are optionally charged with the same amino acids and have different anti-codons. In some embodiments, one or more methods include co-localizing one or more biological assemblers with two or more charged tRNA, wherein at least two of the two or more charged tRNA are at one or more different locations, and wherein two or more of the two or more charged tRNA have the same anti-codon and are optionally charged with different amino acids. In some embodiments, one or more methods include co-localizing one or more biological assemblers with two or more charged tRNA, wherein at least two of the two or more charged tRNA are at one or more different locations, and wherein two or more of the two or more charged tRNA are optionally charged with the same amino acids and have different anti-codons. In some embodiments, one or more methods include co-localizing one or more biological assemblers and two or more charged tRNA, wherein two or more of the two or more charged tRNA have the same anti-codon and are optionally charged with different amino acids. In some embodiments, one or more methods include co-localizing one or more biological assemblers and two or more charged tRNA, wherein two or more of the two or more charged tRNA are optionally charged with the same amino acids and have different anti-codons.

In illustrative embodiments, two of the charged tRNA may have traditional stop anti-codons, for example AUU, but one may be charged with glycine and the other with methionine, for example. In illustrative embodiments, two of the charged tRNA may have traditional stop anti-codons, for example one may have AUU and the other AUC, but both tRNA may be charged with glycine, for example. In illustrative embodiments, two of the charged tRNA may have traditional cysteine anti-codons, for example ACA, but one may be charged with glycine and the other with methionine, for example. In illustrative embodiments, one of the two charged tRNA may have a traditional cysteine anti-codon, for example ACA, while the other may have a traditional histidine anti-codon, for example GUA, but both tRNA may be charged with glycine, for example.

In some embodiments, one or more methods comprises sequentially co-localizing and/or providing two or more charged anti-stop codon tRNA to one or more identifiable locations. In some embodiments, one or more methods comprises sequentially providing two or more charged anti-stop codon tRNA to one or more biological assemblers. In some embodiments, one or more methods comprises sequentially co-localizing one or more biological assemblers with two or more charged anti-stop codon tRNA, wherein at least two charged tRNA are located at one or more different locations. In some embodiments, one or more methods comprises sequentially co-localizing one or more biological assemblers and two or more charged anti-stop codon tRNA.

In some embodiments, one or more methods include 3 or more, 4 or more, 5 or more, 6 or more, 8 or more, 10 or more, 15 or more, 20 or more, or 50 or more charged anti-stop codon tRNA. In some embodiments, one or more methods include from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 charged anti-stop codon tRNA.

In some embodiments, the two or more charged anti-stop codon tRNA have two different anti-stop codon recognition sites. In some embodiments, the two or more charged anti-stop codon tRNA with two different anti-stop codon recognition sites are sequentially co-localized and/or provided in an alternating anti-stop codon recognition site sequence. In some embodiments, biological assemblers are sequentially co-localized with the two or more charged anti-stop codon tRNA in an alternating anti-stop codon recognition site sequence. In some embodiments, the charged anti-stop codon tRNA with two different anti-stop codon recognition sites optionally have aminoacyl groups that change irrespective and/or unrelated to of the identity of the tRNA anti-stop codon. In some embodiments, the method includes at least 2, at least 3, at least 4, at least 5, at least 6, at least 8, at least 10, at least 15, at least 20, or at least 25 charged anti-stop codon tRNA having two different anti-stop codon recognition sites.

In some embodiments, the method includes from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 1, 10 to 500, 10 to 250, 10 to 100, 10 to 50, 10 to 25, 20 to 500, 20 to 250, 20 to 100, or 20 to 50 charged anti-stop codon tRNA having two different anti-stop codon recognition sites.

In some embodiments, one or more methods include sequentially co-localizing and/or providing three or more charged anti-stop codon tRNA having three different anti-stop codon recognition sites in a repeating anti-stop codon recognition site sequence. In some embodiments, one or more methods include sequentially co-localizing one or more biological assemblers with three or more charged anti-stop codon tRNA having three different anti-stop codon recognition sites in a repeating anti-stop codon recognition site sequence, wherein at least two charged tRNA are located at one or more different locations. In some embodiments, one or more methods include sequentially co-localizing one or more biological assemblers and three or more charged anti-stop codon tRNA having three different anti-stop codon recognition sites in a repeating anti-stop codon recognition site sequence.

In some embodiments, the three or more charged anti-stop codon tRNA with three different anti-stop codon recognition sites, optionally have aminoacyl groups that change irrespective and/or unrelated to of the identity of the tRNA anti-stop codon. In some embodiments, one or more methods include at least 3, at least 4, at least 5, at least 6, at least 8, at least 10, at least 15, at least 20, or at least 25 charged anti-stop codon tRNA having three different anti-stop codon recognition sites in a repeating anti-stop codon recognition site sequence. In some embodiments, one or more methods include 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 250, 10 to 250, 10 to 100, 10 to 50, 10 to 25, 20 to 500, 20 to 250, 20 to 100, or 20 to 50 charged anti-stop codon tRNA having three different anti-stop codon recognition sites in a repeating anti-stop codon recognition site sequence.

In some embodiments, one or more methods include sequentially providing two or more charged tRNA in a target sequence to one or more identifiable locations. In some embodiments, one or more methods include sequentially co-localizing two or more charged tRNA with one or more biological assemblers in a target sequence. In some embodiments, one or more methods include co-localizing sequentially one or more biological assemblers with two or more charged tRNA in a target sequence, wherein at least two of the two or more charged tRNA are at one or more different locations. In some embodiments, one or more methods include co-localizing sequentially one or more biological assemblers and two or more charged tRNA in a target sequence.

In some embodiments, one or more methods further include determining the target sequence for sequentially providing two or more charged tRNA to one or more identifiable locations. In some embodiments, one or more methods further include determining the target sequence for sequentially co-localizing two or more charged tRNA with one or more biological assemblers. In some embodiments, one or more methods further include determining the target sequence for co-localizing sequentially the one or more biological assemblers with the two or more charged tRNA, wherein at least two of the two or more charged tRNA are at one or more different locations. In some embodiments, one or more methods further include determining the target sequence for co-localizing sequentially the one or more biological assemblers and the two or more charged tRNA.

In some embodiments, the target sequence is determined based on criteria including, but not limited to, a target peptide sequence, a nucleic acid protein coding sequence, a biological assembler, and/or one or more biological assembler components. In some embodiments, the target sequence is determined based on criteria including, but not limited to, user designations, target output, computer predictions, availability, predicted synthetic time, and/or cost.

In some embodiments, one or more methods include providing and/or co-localizing two or more charged tRNA sequentially at one or more identifiable locations at one or more identifiable time intervals, wherein the one or more identifiable locations contain one or more biological assemblers and/or one or more nucleic acids. In some embodiments, the one or more nucleic acids have a defined and/or target and/or selected protein coding sequence.

In some embodiments, one or more methods include co-localizing sequentially two or more charged tRNA with one or more peptide assemblers, one or more ribosome-based assemblers, one or more nonribosome-based assemblers, one or more prokaryotic ribosome-based assemblers, one or more eukaryotic ribosome-based assemblers, one or more *E. coli* ribosome-based assemblers, and/or one or more mitochondrial ribosome-based assemblers. In some embodiments, one or more methods include co-localizing sequentially one or more biological assemblers, one or more ribosome-based assemblers, one or more nonribosome-based assemblers, one or more prokaryotic ribosome-based assemblers, one or more eukaryotic ribosome-based assemblers, one or more *E. coli* ribosome-based assemblers, and/or one or more mitochondrial ribosome-based assemblers with two or more charged tRNA, wherein at least two of the two or more charged tRNA are at one or more different locations. In some embodiments, one or more methods include co-localizing sequentially one or more biological assemblers, one or more ribosome-based assemblers, one or more nonribosome-based assemblers, one or more prokaryotic ribosome-based assemblers, one or more eukaryotic ribosome-based assemblers, one or more *E. coli* ribosome-based assemblers, and/or one or more mitochondrial ribosome-based assemblers and two or more charged tRNA.

In some embodiments, one or more methods include providing one or more first charged tRNA to one or more identifiable locations; providing one or more second charged tRNA to the one or more identifiable locations; and optionally repeating. In some embodiments, one or more methods further comprise providing one or more third charged tRNA to one or more identifiable locations. In some embodiments, one or more methods comprises co-localizing one or more first charged tRNA with one or more biological assemblers; co-localizing one or more second charged tRNA with one or more biological assemblers; and optionally repeating. In some embodiments, one or more methods further comprise co-localizing one or more third charged tRNA with one or more biological assemblers. In some embodiments, one or more methods include co-localizing one or more biological assemblers with one or more first charged tRNA at one or more first locations; co-localizing the one or more biological assemblers with one or more second charged tRNA at one or more second locations; and optionally repeating. In some embodiments, one or more methods further include co-localizing one or more biological assemblers with one or more third charged tRNA at one or more third locations. In some embodiments, one or more methods include co-localizing one or more biological assemblers and one or more first charged tRNA at one or more first locations; co-localizing the one or more biological assemblers and one or more second charged tRNA at one or more second locations; and optionally repeating. In some embodiments, one or more methods further include co-localizing one or more biological assemblers and one or more third charged tRNA at one or more third locations.

In some embodiments, one or more methods further comprise providing one or more additional charged tRNA to one or more identifiable locations. In some embodiments, one or more methods further comprise co-localizing one or more additional charged tRNA with one or more biological assemblers. In some embodiments, one or more methods further comprise co-localizing one or more biological assemblers with one or more additional charged tRNA, wherein the one or more additional charged tRNA are optionally at one or more different locations. In some embodiments, one or more methods further comprise co-localizing one or more biological assemblers and one or more additional charged tRNA.

In some embodiments, the one or more first charged tRNA is optionally the same as and/or optionally different from the one or more second charged tRNA. In some embodiments, the one or more first charged tRNA includes a stop codon recognition site, and the one or more second charged tRNA includes a stop codon recognition site. In some embodiments, the one or more first charged tRNA stop codon recognition site is different from the one or more second charged tRNA stop codon recognition site. In some embodiments, the one or more third charged tRNA includes a stop codon recognition site that is optionally the same as the one or more first charged tRNA stop codon recognition site and/or the one or more second charged tRNA stop codon recognition site, or optionally different from the one or more first charged tRNA stop codon recognition site and/or the one or more second charged tRNA stop codon recognition site. In some embodiments, the one or more additional charged tRNA have stop codon recognition sites. In some embodiments, the one or more additional charged tRNA having stop codon recognition sites are co-localized such that the stop codon recognition sites of the charged tRNA alternate. In some embodiments, the one or more biological assemblers are co-localized with the one or more additional charged tRNA having stop codon recognition sites such that the stop codon recognition sites of the charged tRNA alternate.

In some embodiments, the one or more first charged tRNA, the one or more second charged tRNA, the one or more third charged tRNA, and/or the one or more additional charged tRNA are optionally the same as, or optionally different from, each other. In some embodiments, the tRNA portion of one or more of the one or more first charged tRNA, the one or more second charged tRNA, the one or more third charged tRNA, or the one or more additional charged tRNA are optionally the same as, or optionally different from, each other. In some embodiments, one or more of the anticodon portions of one or more of the one or more first charged tRNA, the one or more second charged tRNA, the one or more third charged tRNA, or the one or more additional charged tRNA are one or more stop codon recognition sites. In some embodiments, the amino acid portion of one or more of the one or more first charged tRNA, the one or more second charged tRNA, the one or more third charged tRNA, or the one or more additional charged tRNA are optionally the same as, or optionally different from, each other.

In some embodiments, one or more methods comprises co-localizing one or more first charged tRNA with one or more biological assemblers, the one or more first charged tRNA charged with one or more first arbitrary amino acid; removing one or more first tRNA, the one or more first tRNA released during peptide synthesis; co-localizing one or more second charged tRNA with one or more biological assemblers, the one or more second charged tRNA charged with one or more second arbitrary amino acid; removing one or more second tRNA, the one or more second tRNA released during peptide synthesis; and optionally repeating. In some embodiments, the method includes co-localizing one or more biological assemblers with one or more first charged tRNA in one or more first locations, the one or more first charged tRNA charged with one or more first arbitrary amino acid; removing one or more first tRNA, the one or more first tRNA released during peptide synthesis; co-localizing one or more biological assemblers with one or more second charged tRNA at one or more second locations, the one or more second charged tRNA charged with one or more second arbitrary amino acid; removing one or more second tRNA, the one or more second tRNA released during peptide synthesis; and optionally repeating.

In some embodiments, one or more methods include co-localizing one or more biological assemblers with one or more first charged tRNA at one or more first locations, the one or more first charged tRNA charged with one or more arbitrary amino acids; removing the one or more biological assemblers from the one or more first locations; co-localizing the one or more biological assemblers with one or more second charged tRNA at one or more second locations, the second one or more charged tRNA charged with one or more arbitrary amino acids; removing the one or more biological assemblers from the one or more second locations; and optionally repeating. In some embodiments, one or more methods include co-localizing one or more biological assemblers and one or more first charged tRNA at one or more first locations, the first one or more charged tRNA charged with one or more arbitrary amino acids; separating the one or more first charged tRNA and/or one or more released tRNA and the one or more biological assemblers; co-localizing the one or more biological assemblers and one or more second charged tRNA at one or more second locations, the second one or more charged tRNA charged with one or more arbitrary amino acids; separating the one or more second charged tRNA and/or one or more released tRNA and the one or more biological assemblers; and optionally repeating.

In some embodiments, the first arbitrary amino acid is optionally the same as, or optionally different from, the second arbitrary amino acid. In some embodiments, the first tRNA is optionally the same as, or optionally different from, the second tRNA. In some embodiments, the first charged tRNA is optionally the same as, or optionally different from, the second charged tRNA. In some embodiments, the one or more first arbitrary amino acid is the same as the one or more second arbitrary amino acid, and the one or more first tRNA is different from the one or more second tRNA. In some embodiments, the first and the second tRNA have different anti-codons. In some embodiments, the one or more first tRNA is the same as the one or more second tRNA, and the one or more first arbitrary amino acids are different from the one or more second arbitrary amino acids. In some embodiments, the first and the second tRNA have the same anti-codon.

In illustrative embodiments, one or more methods include: providing the first charged tRNA having an anti-codon that recognizes the first codon of the translatable reading frame and having an amino acid attached that is the first amino acid of the target polypeptide; allowing sufficient time for docking of the charged tRNA; providing the second charged tRNA having an anti-codon that recognizes the second codon of the translatable reading frame and having an amino acid attached that is the second amino acid of the target polypeptide; allowing sufficient time for docking of the charged tRNA, peptide bond formation between the first two amino acids, and release of the first tRNA; removal of the first released tRNA; providing the third charged tRNA having an anti-codon that recognizes the third codon of the translatable reading frame and having an amino acid attached that is the third amino acid of the target polypeptide; allowing sufficient time for docking of the charged tRNA, peptide bond formation between the second and the third amino acids, and release of the second tRNA; removal of the second released tRNA; and repeating the process for the target peptide sequence.

In some embodiments, one or more of the methods described herein includes charging one or more tRNA with one or more arbitrary amino acids, one or more natural amino acids or one or more unnatural amino acids. In some embodiments, one or more of the methods described herein includes charging one or more anti-stop codon tRNA with one or more natural amino acids or one or more unnatural amino acids. In some embodiments, aminoacylation is mediated by aminoacyl tRNA synthetases including one or more natural and/or one or more unnatural aminoacyl tRNA synthetases.

In some embodiments, one or more of the methods described herein includes selecting two or more charged tRNA. In some embodiments, two or more charged tRNA are selected at least partially, or completely, based on criteria including, but not limited to, target peptide sequence, a nucleic acid protein coding sequence, a biological assembler, and/or one or more biological assembler components. In some embodiments, the protein coding region of the nucleic acid sequence includes one or more codons selected from the group consisting of two or more stop codons, at least three stop codons, two or more alternating stop codons, one or more singlet codons, one or more doublet codons, one or more triplet codons, one or more quadruplet codons, one or more quintuplet codons, and one or more sextuplet codons. In some embodiments, two or more charged tRNA are selected based on criteria including, but not limited to, user designations, target output, computer predictions, availability, predicted synthetic time, and/or cost.

In some embodiments, one or more of the methods described herein includes selecting one or more biological assemblers. In some embodiments, one or more biological assemblers are selected at least partially based on criteria including, but not limited to, one or more of a target peptide sequence, one or more charged tRNA, or a nucleic acid protein coding sequence. In some embodiments, one or more biological assemblers are selected at least partially based on criteria including, but not limited to, user designations, target output, computer predictions, availability, predicted synthetic time, and cost.

In some embodiments, one or more of the methods described herein includes selecting one or more components of one or more biological assemblers. In some embodiments, one or more biological assembler components are selected at least partially based on criteria including, but not limited to, one or more of a target peptide sequence, one or more charged tRNA, or a nucleic acid protein coding sequence. In some embodiments, one or more biological assembler components are selected at least partially based on criteria including, but not limited to, user designations, target output, computer predictions, availability, predicted synthetic time, and cost.

As used herein, the term "selecting" means any process used to identify for use one or more target components. Processes include, but are not limited to, user selected, user identified, software method analysis, algorithm-based, computer mediated, operations research, optimization, simulation, queuing theory, and/or game theory.

In some embodiments, one or more methods include assembling and/or co-localizing and/or providing one or more components of one or more biological assemblers. In some embodiments, one or more methods include assembling one or more components of the one or more biological assemblers at one or more third identifiable time intervals. In some embodiments, the one or more third identifiable time intervals are at least partially based on a predicted rate of incorporation of two or more amino acids into one or more peptides, a predicted rate of activity of the one or more biological assemblers, a predicted rate of translocation of one of more nucleic acids, and/or a predicted rate of release of tRNA. In illustrative embodiments, one or more methods include assembling one or more first biological assembler components, assembling a target peptide, removing the one or more first biological assembler components, and co-localizing one or more second biological assembler components. In illustrative embodiments, one or more methods include assembling one or more first biological assembler components, commencing synthesis of a target peptide, co-localizing one or more second biological assembler components, and assembling a target peptide.

In some embodiments, one or more methods include assembling one or more components of one or more biological assemblers at one or more third identifiable time intervals, and further comprises monitoring amino acid incorporation into one or more peptides, biological assembler activity, nucleic acid translocation, and/or tRNA release. In some embodiments, one or more methods include assembling one or more components of one or more biological assemblers at one or more third identifiable time intervals, and further include monitoring the presence or absence, concentration, and/or compositions of one or more charged tRNA and/or one or more tRNA. In some embodiments, the one or more identifiable time intervals are at least partially based on availability of one or more nucleic acid codons. In some embodiments, the one or more identifiable time intervals are at least partially based on the concentrations of one or more charged tRNA and/or one or more tRNA. In some embodiments the one or more identifiable time intervals are based on the presence or absence of one or more charged tRNA and/or one or more tRNA. In some embodiments, the one or more identifiable time intervals are based on the presence or absence of one or more anti-codons on one or more charged tRNA and/or one or more tRNA.

In some embodiments, one or more methods of co-localizing sequentially two or more tRNA with one or more biological assemblers, further include co-localizing the one or more biological assemblers at one or more identifiable locations. In some embodiments, one or more methods include co-localizing one or more biological assemblers at one or more identifiable locations at one or more fourth identifiable time intervals. In some embodiments, the one or more fourth identifiable time intervals are at least partially based on a predicted rate of incorporation of one or more amino acids into one or more peptides, a predicted rate of activity of one or more biological assemblers, a predicted rate of translocation of one or more nucleic acids, and/or a predicted rate of release of tRNA. In illustrative embodiments, one or more methods include co-localizing one or more first biological assemblers, assembling a target peptide, removing the one or more first biological assemblers, and co-localizing one or more second biological assemblers.

In some embodiments, one or more methods includes co-localizing one or more biological assemblers at one or more identifiable locations at one or more fourth identifiable time intervals, and further comprises monitoring amino acid incorporation into one or more peptides, biological assembler activity, nucleic acid translocation, and/or tRNA release. In some embodiments, the one or more identifiable time intervals are based on the results of the monitoring. For example, in some embodiments the one or more identifiable time intervals are at least partially based on measurements of amino acid incorporation into one or more peptides, biological assembler activity, nucleic acid translocation, and/or tRNA release. In some embodiments, one or identifiable time intervals are at least partially based on availability of one or more nucleic acid codons.

In some embodiments, one or more methods includes co-localizing one or more biological assemblers at one or more identifiable locations at one or more fourth identifiable time intervals, and further comprises monitoring the presence or absence, concentration, and/or compositions of one or more charged tRNA and/or one or more tRNA released during peptide synthesis. In some embodiments, the one or more identifiable time intervals are based on the results of monitoring. For example, the one or more identifiable time intervals may be at least partially based on the concentrations of one or more charged tRNA and/or one or more tRNA, the presence or absence of one or more charged tRNA and/or one or more tRNA, and/or the presence or absence of one or more anti-codons on one or more charged tRNA and/or one or more tRNA.

In some embodiments, co-localizing, optionally sequentially, two or more charged tRNA with one or more biological assemblers occurs at least partially, and optionally completely, following co-localizing the one or more biological assemblers at one or more identifiable locations. In some embodiments, co-localizing, optionally sequentially, one or more biological assemblers with two or more charged tRNA, wherein at least two of the two or more charged tRNA are at different locations, occurs at least partially, and optionally completely, following co-localizing the two or more charged tRNA at one or more different locations.

As used herein, the term "assembling" means any process resulting in one or more components being in the same place. In some embodiments, the components may be assembled by one or more methods including, but not limited to, one or more of co-localized, provided, injected, aggregated, commingled, combined, mixed or any other similar method.

In illustrative embodiments, fluid flow is used to "flow" one or more components into association (or assemblage). In some embodiments, the components may be all of one type, or of one or more types. In some embodiments, the components may be an admixture of ribosomal and non-ribosomal components, or biological and non-biological components.

As used herein, the term "type" means a difference in kind. For example, "type" as used with biological assemblers and/or biological assembler components may refer to chloroplast versus mitochondrial ribosomal assemblers, or prokaryotic versus eukaryotic ribosomal assemblers, or ribosomal versus nonribosome assemblers. Type may also refer to differences in kind for nucleic acids, for example, DNA versus RNA, or eukaryotic versus prokaryotic, or plasmid versus linear. Type may also refer to differences in kind for charged tRNA and/or tRNA, for example, based on differences in the anti-codon, or eukaryotic versus prokaryotic, or natural versus unnatural. Type may also refer to differences in kind for amino acids, for example, based on differences of natural versus unnatural.

In some embodiments, one or more methods include one or more biological assemblers that are affixed at one or more identifiable locations. In some embodiments, one or more of the methods further comprise affixing one or more biological assemblers at one or more identifiable locations and/or to one or more devices. In some embodiments, one or more of the methods include co-localizing sequentially two or more charged tRNA with one or more biological assemblers, wherein the one or more biological assemblers are affixed at one or more identifiable locations. In some embodiments, one or more methods include affixing one or more nucleic acids at one or more identifiable locations and/or to one or more devices.

In some embodiments, one or more methods include two or more charged tRNA affixed at one or more different locations. In some embodiments, one or more methods include affixing two or more charged tRNA at two or more different locations and/or the two or more different devices. In some embodiments, one or more methods include co-localizing sequentially one or more biological assemblers with two or more charged tRNA, wherein at least two of the two or more charged tRNA are located at one or more different locations, and wherein the at least two of the two or more charged tRNA are affixed at the two or more different locations. In some embodiments, one or more devices include, but are not limited t, one or more microelectromechanical systems (MEMS) devices, beads, and/or immunoassay arrays.

In illustrative embodiments, two or more charged tRNA are affixed in two or more liquid beads. In illustrative embodiments, fluid flow is used to co-localize one or more biological assemblers sequentially with each of the two or more charged tRNA in two or more liquid beads. In illustrative embodiments, excess charged tRNA and/or released tRNA are removed using fluid flow and differential filtration.

In some embodiments, one or more methods include co-localizing sequentially one or more biological assemblers with two or more charged tRNA, wherein at least two of the two or more charged tRNA are located at one or more different locations, and further includes co-localizing the at least two of the two or more charged tRNA at the one or more different locations. In some embodiments, the co-localizing sequentially one or more biological assemblers with the at least two of the two or more charged tRNA occurs at least partially following the co-localizing the at least two of the two or more charged tRNA at the one or more different locations. In some embodiments, one or more methods include co-localizing sequentially one or more biological assemblers with two or more charged tRNA, wherein at least two of the two or more charged tRNA are located at one or more different locations, and further includes removing one or more of the at least two of the two or more charged tRNA or one or more released tRNA from the one or more different locations.

In illustrative embodiments, one or more methods comprise: co-localizing, optionally sequentially, one or more first charged tRNA at one or more first identifiable locations, one or more second charged tRNA at one or more second identifiable locations, and one or more third charged tRNA at one or more third identifiable locations; co-localizing and subsequently removing one or more biological assemblers with the one or more first charged tRNA at the one or more first locations, with the one or more second charged tRNA at the one or more second locations, and/or with the one or more third charged tRNA at the one or more third locations in a target sequence; removing one or more first charged tRNA and/or one or more released tRNA from the one or more first locations, one or more second charged tRNA and/or one or more released tRNA from the one or more second locations, and/or one or more third charged tRNA and/or one or more released tRNA from at the one or more third locations depending on the target sequence; and optionally repeating until a target peptide is synthesized.

In some embodiments, one or more methods include co-localizing sequentially one or more biological assemblers with two or more charged tRNA, wherein at least two of the two or more charged tRNA are located at one or more different locations, and further includes co-localizing the at least two of the two or more charged tRNA at the one or more different locations at one or more identifiable time intervals. In some embodiments, one or more methods include co-localizing sequentially one or more biological assemblers with two or more charged tRNA, wherein at least two of the two or more charged tRNA are located at one or more different locations, and further includes removing one or more of the at least two of the two or more charged tRNA or one or more released tRNA from the one or more different locations at one or more identifiable time intervals. The time intervals for providing the charged tRNA and the time intervals for removing the charged tRNA and/or released tRNA may be the same or different. The one or more identifiable time intervals for providing the charged tRNA and the time intervals for removing the charged tRNA and/or released tRNA are at least partially based on one or more of a predicted rate of incorporation of two or more amino acids into one or more peptides, a predicted rate of activity of the one or more biological assemblers, a predicted rate of translocation of one or more nucleic acids, or a predicted rate of release of tRNA.

In some embodiments, one or more methods include co-localizing sequentially one or more biological assemblers with two or more charged tRNA, wherein at least two of the two or more charged tRNA are located at one or more different locations; co-localizing the at least two of the two or more charged tRNA at the one or more different locations at one or more identifiable time intervals; and further includes monitoring amino acid incorporation into one or more peptides, biological assembler activity, nucleic acid translocation, and/or tRNA release. In some embodiments, one or more methods include co-localizing sequentially one or more biological assemblers with two or more charged tRNA, wherein at least two of the two or more charged tRNA are located at one or more different locations; removing one or more of the at least two of the two or more charged tRNA or one or more released tRNA from the one or more different locations at one or more identifiable time intervals; and further includes monitoring amino acid incorporation into one or more peptides, biological assembler activity, nucleic acid translocation, and/or tRNA release. In some embodiments, the one or more first identifiable time intervals are at least partially based on the results of the monitoring, including but not limited to measurements of the amino acid incorporation into the one or more peptides, the biological assembler activity, the nucleic acid translocation, and/or the tRNA release. In some embodiments, the one or more first identifiable time intervals are at least partially based on availability of one or more nucleic acid codons.

In some embodiments, one or more methods include co-localizing sequentially one or more biological assemblers with two or more charged tRNA, wherein at least two of the two or more charged tRNA are located at one or more different locations; co-localizing the at least two of the two or more charged tRNA at the one or more different locations at one or more identifiable time intervals; and further includes monitoring the presence or absence, concentration, and/or composition of one or more charged tRNA and/or one or more tRNA. In some embodiments, one or more methods include co-localizing sequentially one or more biological assemblers with two or more charged tRNA, wherein at least two of the two or more charged tRNA are located at one or more different locations; removing one or more of the at least two of the two or more charged tRNA or one or more released tRNA from the one or more different locations at one or more identifiable time intervals; and further includes monitoring the presence or absence, concentration, and/or composition of one or more charged tRNA and/or one or more tRNA. In some embodiments, the one or more first identifiable time intervals are at least partially based on the results of the monitoring, including but not limited to the concentration, presence or absence of one or more charged tRNA and/or one or more tRNA, and/or the presence or absence of one or more anti-codons on one or more charged tRNA and/or one or more tRNA.

As used herein, the term "identifiable location" means a position in space and time that can be determined. In some embodiments, one or more identifiable locations are internal to a device or apparatus and/or external to a device or apparatus. In some embodiments, the one or more identifiable locations are moving in time and/or moving in space. In some embodiments, the movement in time and/or space may be one or more of steady, fluctuating, predictable or other type of movement so long as the location can be identified at a particular place and time.

In some embodiments, one or more of the processes and/or elements of processes occur at one or more identifiable locations that may be the same or may be different. In some embodiments the terms, "first", "second", "third", "fourth", "fifth", "sixth", etc. may be used to indicate that the identifiable locations are optionally different identifiable locations. Generally, identifiable locations indicated by the same numeral are the same locations unless context indicates otherwise.

As used herein, the term "different location" means an identifiable location that is in a different position in space and/or time from another identifiable location.

As used herein, the term "devices" means any configuration capable of localizing and/or containing one or more components at least temporarily. Devices may include, but are not limited to, containers, receptacles, semi-permeable membranes, beads of liquid, MEMS, microfluidics devices, arrays, liposomes, and/or surface-tension attached liquids.

As used herein, the term "affixing" means any process that at least temporarily restricts the movement of one or more components in relation to an identifiable location and/or one or more devices. Processes include, but are not limited to, attachment, filtration, ultrafiltration, resins, changes in aperture diameter, optical traps, and/or electric fields. Affixing may be through direct and/or indirect means including, for example, affixing one or more biological assemblers by affixing the one or more nucleic acids that the one or more biological assemblers are translating. Attachment includes, but is not limited to, methods known in the art for attaching membranes to a variety of support structures, for attaching nucleic acids to a variety of support structures, and for attaching proteins to a variety of support structures. Support structures include, but are not limited to, beads, microfluidic devices, MEMS devices, carbon nanotubes, arrays, and/or microstructured surfaces.

In some embodiments, one or more methods include providing and/or co-localizing two or more charged tRNA sequentially into one or more receptacles at one or more identifiable locations. In some embodiments, one or more methods include providing and/or co-localizing two or more charged tRNA sequentially into one or more receptacles at one or more identifiable locations at one or more identifiable time intervals. In some embodiments, one or more methods include injecting sequentially two or more charged tRNA into one or more receptacles containing one or more biological receptors. In some embodiments, the one or more receptacles contain one or more biological assemblers and/or one or more nucleic acids.

In some embodiments, one or more methods include co-localizing sequentially two or more charged tRNA with one or more biological assemblers that are co-localized with one or more nucleic acids. In some embodiments, one or more methods include co-localizing sequentially one or more biological assemblers and two or more charged tRNA, wherein the one or more biological assemblers are co-localized with one or more nucleic acids. In some embodiments, multiple biological assemblers are co-localized with one or more nucleic acids. In some embodiments, multiple biological assemblers are optionally translating one or more nucleic acids at the same time.

In some embodiments, the one or more nucleic acids include, but are not limited to, one or more DNA, one or more cDNA, one or more RNA, and/or one or more mRNA. In some embodiments, one or more nucleic acids may be recombinant, circular, linear, plasmid, double stranded, single stranded, poly-adenylated, or any other form known in the art suitable for protein synthesis. In some embodiments, one more nucleic acids have a defined and/or selected and/or target protein coding sequence.

As used herein, the term "nucleic acid or nucleic acids" means one or more complex, high-molecular-weight biochemical macromolecules composed of nucleotide chains. Nucleic acids include, but are not limited to, one or more forms of deoxyribonucleic acid (DNA), ribonucleic acid (RNA; includes messenger RNA (mRNA)), and complementary DNA (cDNA; DNA synthesized from an mRNA template).

As used herein, the term "target protein coding sequence" means a translatable reading frame in one or more nucleic acids. In some embodiments, the translatable reading frames are open reading frames that translate into a target peptide using the standard genetic code. In some embodiments, the translatable reading frames do not translate into a target peptide using the standard genetic code.

In some embodiments, the translatable reading frames contain at least one stop codon. In some embodiments, the translatable reading frames have a protein coding sequence having at least 2, at least 3, at least 4, at least 5, at least 6, at least 8, at least 10, at least 15, at least 20, or at least 25 stop codons. In some embodiments, the translatable reading frames have a protein coding sequence having from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 stop codons.

In some embodiments, the stop codons are two different stop codons in an alternating sequence. In some embodiments, the alternating stop codon sequence includes, but is not limited to, at least 2, at least 3, at least 4, at least 5, at least 6, at least 8, at least 10, at least 15, at least 20, or at least 25 alternating stop codons. In some embodiments, the alternating stop codon sequence has from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 alternating stop codons.

In some embodiments, the stop codons are three different stop codons in a repeating sequence. In some embodiments, the repeating stop codon sequence includes, but is not limited to, at least 3, at least 4, at least 5, at least 6, at least 8, at least 10, at least 15, at least 20, or at least 25 repeating stop codons. In some embodiments, the repeating stop codon sequence has from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 repeating stop codons.

In some embodiments, the translatable reading frames contain one or more of at least one singlet codon, at least one doublet codon, at least one triplet codon, at least one quadruplet codon, at least one quintuplet codon, or at least one sextuplet codon. In some embodiments, the translatable reading frames have a protein coding sequence having at least 2, at least 3, at least 4, at least 5, at least 6, at least 8, at least 10, at least 15, at least 20, or at least 25 singlet, doublet, triplet, quadruplet, quintuplet, and/or sextuplet codons. In some embodiments, the translatable reading frames have a protein coding sequence having from 2 to 500, 2 to 200, 2 to 100, 2 to 50, 2 to 25, 2 to 10, 2 to 5, 4 to 500, 4 to 250, 4 to 100, 4 to 50, 4 to 25, 4 to 10, 10 to 500, 10 to 250, 10 to 100, 10 to 50, 10 to 25, 20 to 500, 20 to 250, 20 to 100, or 20 to 50 singlet, doublet, triplet, quadruplet, quintuplet, and/or sextuplet codons.

Methods of synthesizing nucleic acids are known in the art including, but not limited to, chemical and enzymatic synthesis. Proteins/peptides translated from nucleic acids with modified translatable reading frames, including sense codon reassignment are known in the art (e.g. Methods (2005) 36:227-238; Methods (2005) 36:270-278; Methods (2005) 36:279-290; Methods (2005) 36:291-298; Annu. Rev. Biochem. (2004) 73:147-176; Nucleic Acids Research (2004) 32:6200-6211; PNAS (2003) 100:6353-6357)

As used herein, the term "target protein or target protein sequence" means one or more identified and/or selected polypeptide sequences. In some embodiments, the target peptide sequence is directly translatable from the target protein coding sequence of one or more nucleic acids using the genetic code. In some embodiments, the target peptide sequence is not directly translatable from the target protein coding sequence of one or more nucleic acids using the genetic code.

In other embodiments, one or more methods include co-localizing one or more nucleic acids with one or more biological assemblers. Some embodiments include any process that results in one or more components being in the same place. One or more nucleic acids and one or more biological assemblers may be assembled, aggregated, commingled, combined or mixed, or other similar methods. Processes, including sequential processes, are known in the art and include, but are not limited to, one or more of automated methods, mechanical methods, computer and/or software-controlled methods, and fluid flow. Fluid flow includes, but is not limited to, nanofluidics and microfluidics. Nanofluidics and microfluidics include, but are not limited to, continuous flow microfluidics and digital microfluidics, and have been developed for use in biological systems (Annu. Rev. Fluid Mech. (2004) 36:381-411; Annu. Rev. Biomed. Eng. (2002) 4:261-86; Science (1988) 242:1162-1164, Rev. Mod. Phys. (2005) 77:977-1026).

In some embodiments, one or more methods include co-localizing one or more nucleic acids with one or more biological assemblers at one or more fifth identifiable time intervals. In some embodiments, the one or more fifth identifiable time intervals are at least partially based on a predicted rate of incorporation of amino acids into peptides, a predicted rate of activity of biological assemblers, a predicted rate of translocation of nucleic acids and/or a predicted rate of release of tRNA.

In some embodiments, one or more methods that include co-localizing one or more nucleic acids with one or more biological assemblers at one or more fifth identifiable time intervals, further include monitoring amino acid incorporation into peptides, biological assembler activity, nucleic acid translocation, and/or tRNA release. In some embodiments, the results of monitoring one or more of amino acid incorporation into peptides, biological assembler activity, nucleic acid translocation, or tRNA release are at least partially used to identify time intervals for co-localization of nucleic acids. In some embodiments, the one or more fifth identifiable time intervals are at least partially based on availability of one or more nucleic acid codons.

In some embodiments, one or more methods that include co-localizing one or more nucleic acids with one or more biological assemblers at one or more fifth identifiable time intervals, further include monitoring the presence or absence, concentration, and/or compositions of one or more charged tRNA and/or one or more tRNA. In some embodiments, the results of monitoring the presence or absence, concentration, and/or compositions of one or more charged tRNA and/or one or more tRNA are at least partially used to identify time intervals for co-localization of nucleic acids. In some embodiments, the one or more fifth identifiable time intervals are at least partially based on the presence or absence of one or more charged tRNA and/or one or more tRNA, and/or the presence or absence of one or more anti-codons on one or more charged tRNA and/or one or more tRNA.

In some embodiments, one or more methods include co-localizing, optionally sequentially, two or more charged tRNA with one or more biological assemblers at least partially, or optionally completely, following co-localizing one or more nucleic acids with one or more biological assemblers. In some embodiments, one or more methods include co-localizing, optionally sequentially, one or more biological assemblers with two or more charged tRNA, at least partially, or optionally completely, following co-localizing one or more nucleic acids with the one or more biological assemblers. In some embodiments, one or more methods include co-localizing, optionally sequentially, one or more biological assemblers and two or more charged tRNA, at least partially, or optionally completely, following co-localizing one or more nucleic acids with the one or more biological assemblers.

In some embodiments, one or more methods include selecting one or more nucleic acids, including but not limited to, RNA, DNA, cDNA, and mRNA. In some embodiments, the method includes selecting one or more nucleic acids having a selected and/or target protein coding sequence. In some embodiments, one or more nucleic acids are selected based on criteria including, but not limited to, one or more of a target peptide sequence, a target nucleic acid protein coding sequence, one or more charged tRNA, one or more biological assemblers, or one or more biological assembler components. For example, the one or more nucleic acid sequences may be selected at least partially based on the selected target peptide sequence and the selected biological assemblers and/or biological assembler components (e.g. Ef-Tu; Biochemistry (2006) 44:11254-11261). In some embodiments, one or more nucleic acids are selected based on criteria including, but not limited to, user designations, target output, computer predictions, availability, predicted synthetic time, and/or cost.

Some embodiments include any process used to identify for use one or more target components. Processes include, but are not limited to, user selected, user identified, software method analysis, algorithm-based, computer mediated, operations research, optimization, simulation, queuing theory, and/or game theory.

In some embodiments, one or more of the methods described herein includes synthesizing one or more nucleic acids. In some embodiments, one or more nucleic acids are synthesized to have a selected/target protein coding sequence. In yet other embodiments, the method includes synthesizing the one or more nucleic acids using two or more singlet codons, two or more doublet codons, two or more triplet codons, two or more quadruplet codons, two or more quintuplet codons, and/or two or more sextuplet codons. In other embodiments, the method includes synthesizing one or more nucleic acids using two or more stop codons. In some embodiments, the method includes synthesizing one or more nucleic acids using two or more different stop codons or three or more different stop codons. In some embodiments, the nucleic acids are synthesized having alternating stop codons and/or repeating stop codons. In some embodiments, the nucleic acids are synthesized having any one of the translatable reading frames described herein.

As used herein, the term "synthesizing" means any process resulting in two or more nucleotides being joined to form a nucleic acid. Processes to synthesize DNA and RNA are well known to those of skill in the art and include, but are not limited to, one or more of enzymatic or chemical methods such as polymerase chain reaction and phosphoramidite chemistry followed by deprotection, for example.

In some embodiments, one or more methods include synchronizing sequentially providing two or more charged tRNA at one or more identifiable locations, with a selected or target protein coding sequence of one or more nucleic acids. In some embodiments, one or more methods include synchronizing sequentially co-localizing two or more charged tRNA with the one or more biological assemblers, with a selected or target protein coding sequence of one or more nucleic acids. In some embodiments, one or more methods include synchronizing sequentially co-localizing one or more biological assemblers with two or more charged tRNA, with a selected or target protein coding sequence of one or more nucleic acids. In some embodiments, one or more methods include synchronizing sequentially co-localizing one or more biological assemblers and two or more charged tRNA, with a selected or target protein coding sequence of one or more nucleic acids.

In some embodiments, the nucleic acid protein coding sequence and the target protein sequence both follow the standard genetic code, therefore sequential co-localization of charged tRNA also follows the standard genetic code, and synchronization is based on the standard genetic code. In some embodiments, the target protein coding sequence includes one or more modified or unnatural amino acids, and synchronization between the target peptide sequence and the nucleic acid protein coding sequence allows the co-localization of a charged tRNA with standard anti-codon recognition sequence and attached modified/unnatural aminoacyl group. In other embodiments, the nucleic acid protein coding sequence and target protein coding sequence do not follow the standard genetic code, therefore synchronization between the target peptide sequence and the nucleic acid protein coding sequences allows co-localization of charged tRNA with the anti-codon recognition sequences to pair with the nucleic acid codons and attached aminoacyl groups that follow the target protein coding sequence.

In other embodiments, one or more of the methods described herein includes synchronizing synthesizing one or more nucleic acids, with co-localizing two or more charged tRNA with one or more biological assemblers. In other embodiments, one or more of the methods described herein includes synchronizing synthesizing one or more nucleic acids, with co-localizing one or more biological assemblers with two or more charged tRNA, wherein at least two of the two or more charged tRNA are at one or more different locations. In other embodiments, one or more of the methods described herein includes synchronizing synthesizing one or more nucleic acids, with sequentially co-localizing one or more biological assemblers and two or more charged tRNA.

In some embodiments, the nucleic acid protein coding sequence and the target protein sequence both follow the standard genetic code, therefore synchronization of nucleic acid protein coding region synthesis with co-localizing charged tRNA is based on the standard genetic code. In some embodiments, the target protein coding sequence includes one or more modified or unnatural amino acids, therefore synchronization allows a nucleic acid protein coding region to be synthesized with a target sequence to that coordinates with co-localization (and incorporation) of a charged tRNA with an attached modified/unnatural aminoacyl group. In other embodiments, the nucleic acid protein coding sequence and target protein coding sequence do not follow the standard genetic code, therefore synchronization of nucleic acid protein coding region synthesis with co-localizing charged tRNA allows the synthesis of a nucleic acid protein coding sequence with codons that will pair with the charged tRNA anti-codon recognition sequences having attached aminoacyl groups that follow the target protein coding sequence.

In other embodiments, one or more of the methods described herein includes synchronizing synthesizing one or more nucleic acids, and charging one or more tRNA with one or more natural amino acids, one or more arbitrary amino acids, and/or one or more unnatural amino acids. In some embodiments, the nucleic acid protein coding sequence and the target protein sequence both follow the standard genetic code, therefore synchronization of nucleic acid protein coding region synthesis with charging tRNA with amino acids is based on the standard genetic code. In some embodiments, the target protein coding sequence includes one or more modified or unnatural amino acids, therefore synchronization of nucleic acid protein coding region synthesis and tRNA charging allows the coordination of the nucleic acid codon and tRNA anti-codon pairing for the charged tRNA with an attached modified/unnatural aminoacyl group. In other embodiments, the nucleic acid protein coding sequence and target protein coding sequence do not follow the standard genetic code, therefore synchronization of nucleic acid protein coding region synthesis with tRNA charging allows the synthesis of a nucleic acid protein coding sequence with codons that will pair with the charged tRNA anti-codon recognition sequences having attached aminoacyl groups that follow the target protein coding sequence.

As used herein, the term "synchronizing" means any one or more processes coordinating one or more elements of one or more methods. The one or more elements of one or more methods may include, but are not limited to one or more of two or more processes, or one or more processes and one or more target sequences. The one or more processes may include, but are not limited to, user defined, software-based, algorithm-based, computer mediated, operations research, optimization, simulation, queuing theory, and/or game theory.

In some embodiments, one or more methods further comprise partially or completely isolating the one or more target peptide following synthesis. Methods for isolating proteins are well-known in the art.

In one aspect, the disclosure is drawn to one or more apparatus for peptide synthesis. In some embodiments, any one of the methods described herein may be performed on one or more apparatus.

FIG. 1 shows a schematic 400 of an illustrative apparatus 410 for biologically synthesizing peptides in which embodiments may be implemented. The apparatus 410 is optionally operable for extra-cellular and/or cell-free peptide synthesis. In some embodiments, the peptide synthesis is in vitro. The apparatus may optionally be, or include, one or more units including, but not limited to, one or more peptide synthesizer units 420, one or more sourcing units 432, one or more monitoring units 440, one or more controller units 422, one or more computing units 426, one or more tRNA charging units 428, and/or one or more nucleic acid synthesizer units 430. In some embodiments, one or more of the units may be internal or external to the apparatus.

In some embodiments, one or more apparatus 410 further includes one or more fluid flows. In some embodiments, the one or more fluid flows connect and/or allow the transfer of one or more peptide synthesis components among one or more of the optional one or more units of the apparatus 410. In some embodiments, the one or more fluid flows are operable to provide, co-localize, remove and/or separate, optionally sequentially, one or more peptide synthesis components. In some embodiments, the one or more fluid flows are operable to provide, co-localize, remove and/or separate, optionally sequentially, one or more peptide synthesis components at one or more identifiable time intervals.

Figure 2:
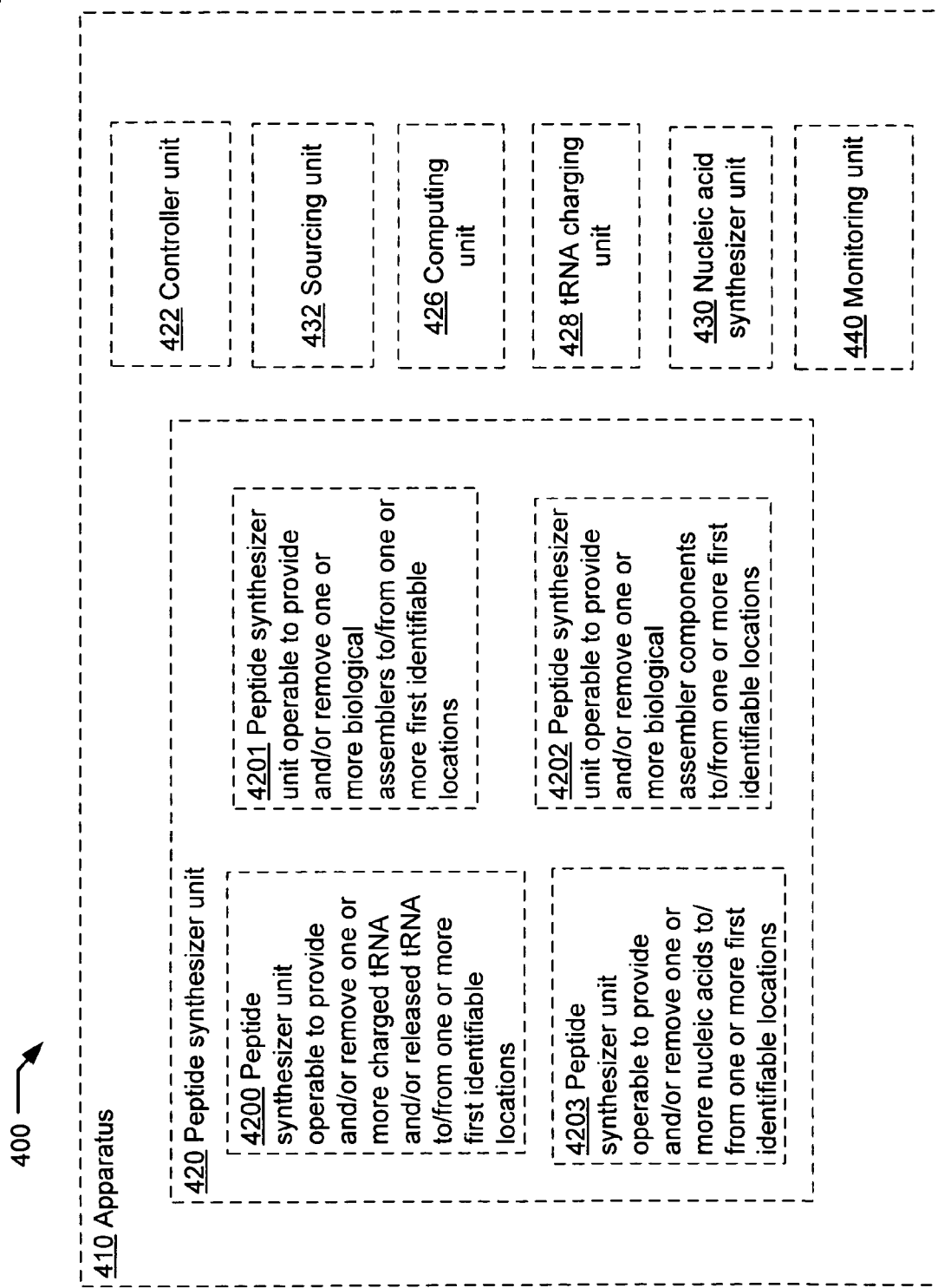
FIG. 2 shows schematics of illustrative embodiments of the apparatus of FIG. 1, with illustrative examples of a peptide synthesizer unit.

FIG. 2 shows a schematic 400 of illustrative embodiments of the optional apparatus 410 of FIG. 1, with specific illustrative embodiments of one or more peptide synthesizer units 420, including unit 4200, unit 4201, unit 4202, and unit 4203. In some embodiments, one or more peptide synthesizer units are operable to provide, optionally sequentially, one or more peptide synthesis components to one or more identifiable locations. In some embodiments, one or more peptide synthesizer units are operable to co-localize, optionally sequentially, one or more peptide synthesis components. In some embodiments, one or more peptide synthesizer units are operable to remove, optionally sequentially, one or more peptide synthesis components from one or more identifiable locations. In some embodiments, one or more peptide synthesizer units are operable to separate, optionally sequentially, one or more peptide synthesis components.

In some embodiments, the one or more peptide synthesizer units are operable to provide, co-localize, remove, and/or separate, optionally sequentially, one or more peptide synthesis components at one or more first identifiable locations, wherein the one or more identifiable locations include one more temporal-spatial locations. In some embodiments, one or more temporal-spatial locations are moving along predictable time or other sequential path. In some embodiments, the one or more identifiable locations are one location. In some embodiments, the one or more identifiable locations are external to the apparatus. In some embodiments, the one or more identifiable locations are internal to the apparatus, and/or one or more of the optional units within the apparatus. In some embodiments, each operable element may have a different identifiable location or one or more operable elements may have similar and/or identical identifiable locations.

In some embodiments, the one or more peptide synthesizer units are operable to provide, co-localize, remove, and/or separate, optionally sequentially, one or more peptide synthesis components at one or more identifiable time intervals. In some embodiments, the one or more first identifiable time intervals are at least partially based on a predicted rate of incorporation of two or more amino acids into one or more peptides, a predicted rate of activity of one or more biological assemblers, a predicted rate of translocation of one or more nucleic acids, and/or a predicted rate of release of tRNA. In some embodiments, the one or more first identifiable time intervals are from approximately 0.001 seconds to approximately 0.01 seconds, or are approximately 0.01 seconds, and/or other appropriate time intervals as described elsewhere. In some embodiments, each operable element may have a different identifiable time interval or one or more operable elements may have a similar and/or identical identifiable time interval.

In some embodiments, the one or more peptide synthesizer units include one or more fluid flows. The one or more fluid flows may be used to provide and/or co-localize components for peptide synthesis in one or more identifiable locations. The one or more fluid flows may be used to remove and/or separate components for peptide synthesis from the one or more identifiable locations. The one or more fluid flows may be used to transfer one or more charged tRNA, one or more biological assemblers, one or more biological assembler components, and/or one or more nucleic acids to and/or from one or more identifiable locations. In some embodiments, the one or more fluid flows are operable to transfer one or more peptide synthesis components to one or more identifiable locations at one or more identifiable time intervals.

In some embodiments, the one or more peptide synthesizer units are operable to optionally affix one or more peptide synthesis components, including but not limited to, one or more biological assemblers, one or more charged tRNA, one or more nucleic acids, and/or one or more biological assembler components. In some embodiments, one or more peptide synthesis components are affixed at one or more identifiable locations.

In some embodiments, one or more peptide synthesizer units are optionally operable to isolate one or more target peptides following partial complete synthesis.

In one aspect, the disclosure is drawn to one or more apparatus comprising one or more peptide synthesizer units that are operable to co-localize two or more charged tRNA with one or more biological assemblers at one or more first identifiable locations. Unit 4200 is optionally one or more peptide synthesizer units operable to provide and/or to remove one or more charged tRNA and/or released tRNA to and/or from one or more first identifiable locations. In some embodiments, one or more peptide synthesizer units are operable to sequentially provide two or more charged tRNA to one or more first identifiable locations. In some embodiments, one or more peptide synthesizer units are further operable to remove and/or separate, optionally sequentially, two or more charged tRNA and/or tRNA and/or other components from one or more first identifiable locations. In some embodiments, one or more peptide synthesizer units are operable to provide, optionally sequentially, two or more charged tRNA to one or more first identifiable locations, and to remove and/or separate, optionally sequentially, two or more charged tRNA and/or one or more tRNA from one or more first identifiable locations.

In some embodiments, the one or more peptide synthesizer units are operable to optionally sequentially provide two or more charged tRNA to one or more identifiable locations at one or more first identifiable time intervals. In some embodiments, the one or more peptide synthesizer units are further operable to optionally sequentially separate two or more charged tRNA from one or more identifiable locations at one or more second identifiable time intervals.

Unit 4201 is optionally one or more peptide synthesizer units operable to provide and/or to remove one or more biological assemblers to and/or from one or more identifiable locations. In some embodiments, one or more apparatus include one or more peptide synthesizer units that are operable to provide, optionally sequentially, one or more biological assemblers to one or more first identifiable locations. In some embodiments, one or more units are further operable to remove, optionally sequentially, one or more biological assemblers from one or more first identifiable locations.

In some embodiments, the one or more peptide synthesizer units are further operable to affix one or more biological assemblers at one or more first identifiable locations. In some embodiments, the one or more biological assemblers are affixed at one or more first identifiable locations.

In some embodiments, the one or more peptide synthesizer units are operable to co-localize, optionally sequentially, one or more biological assemblers with two or more charged tRNA, wherein at least two of the two or more charged tRNA are at one or more different locations. In some embodiments, one or more units are further operable to separate, optionally sequentially, the one or more biological assemblers from the two or more charged tRNA. In some embodiments, one or more apparatus include one or more peptide synthesizer units that are operable to co-localize, optionally sequentially, one or more biological assemblers and two or more charged tRNA, at one or more identifiable locations. In some embodiments, one or more units are further operable to separate, optionally sequentially, the one or more biological assemblers and the two or more charged tRNA.

In some embodiments, the one or more biological assemblers may be one or more peptide assemblers, one or more ribosome-based biological assemblers, and/or one or more non-ribosome-based biological assemblers. The one or more ribosome-based biological assemblers may be eukaryotic, mitochondrial and/or prokaryotic, among others.

Unit 4202 is optionally one or more peptide synthesizer units operable to provide and/or to remove one or more biological assembler components to and/or from one or more identifiable locations. In some embodiments, one or more apparatus include one or more peptide synthesizer units that are operable to provide, optionally sequentially, one or more biological assemblers components to one or more second identifiable locations. In some embodiments, one or more peptide synthesizer units are operable to remove, optionally sequentially, one or more biological assembler components from one or more second identifiable locations. The one or more second identifiable locations are optionally the same as, or optionally different from the first one or more identifiable locations.

The one or more biological assembler components, may be one or more peptide assembler components, one or more ribosome-based biological assembler components, and/or one or more non-ribosome-based biological assembler components. The one or more ribosome-based biological assembler components may be eukaryotic, mitochondrial and/or prokaryotic, among others.

Unit 4203 is optionally one or more peptide synthesizer units operable to provide and/or to remove one or more nucleic acids to and/or from one or more identifiable locations. In some embodiments, one or more apparatus include one or more peptide synthesizer units that are operable to provide, optionally sequentially, one or more nucleic acids to one or more first identifiable locations. In some embodiments, one or more apparatus includes one or more peptide synthesizer units that are operable to remove, optionally sequentially, one or more nucleic acids from one or more first identifiable locations. In some embodiments, one or more nucleic acids are one or more DNA, one of more cDNA, one or more RNA and/or one or more mRNA.

Figure 3:
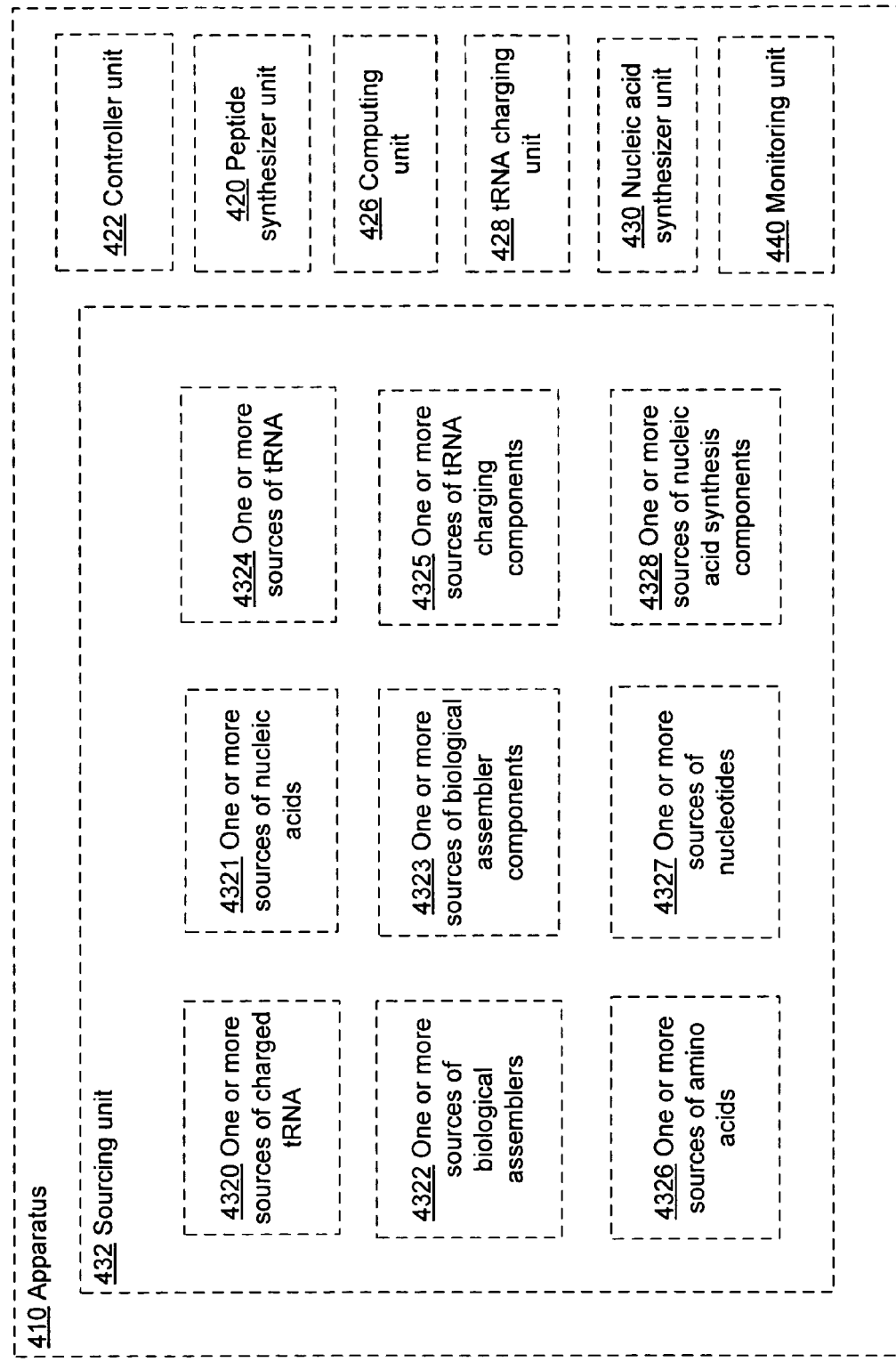
FIG. 3 shows schematics of illustrative embodiments of the apparatus of FIG. 1, with specific examples of a sourcing unit.

FIG. 3 shows a schematic 400 of illustrative embodiments of the apparatus 410 of FIG. 1, with specific illustrative embodiments of one or more sourcing units 432, including unit 4320, unit 4322, unit 4321, unit 4323, unit 4324, unit 4325, unit 4326, unit 4327, and/or unit 4328. In some embodiments, one or more sourcing units 432 optionally contain one or more peptide synthesis components. In some embodiments, one or more apparatus includes, but is not limited to, one or more peptide synthesizer units 420 and one or more sourcing units 432. In some embodiments, one or more of the one or more peptide synthesizer units 420 and one or more of the one or more sourcing units 432 are the same unit. In some embodiments, one or more sourcing units 432 include one or more fluid flows. In some embodiments, one or more sourcing units 432 are operable to provide/co-localize/remove/separate one or more peptide synthesis components from one or more identifiable locations.

In some embodiments, one or more sourcing units 432 are operable to provide/co-localize/remove/separate one or more peptide synthesis components from one or more identifiable locations at one or more identifiable time intervals. In some embodiments, the one or more identifiable time intervals are at least partially based on a predicted rate of incorporation of two or more amino acids into one or more peptides, a predicted rate of activity of one or more biological assemblers, a predicted rate of translocation of one or more nucleic acids, and/or a predicted rate of release of tRNA. In some embodiments, the one or more identifiable time intervals are from approximately 0.001 seconds to approximately 0.1 seconds and/or approximately 0.01 seconds, or other appropriate time interval.

In some embodiments, one or more sourcing units include one or more sources of charged tRNA 4320, one or more sources of biological assemblers 4322, one or more sources of biological assembler components 4323, one or more sources the nucleic acids 4321, one or more sources of DNA, one or more sources of cDNA, one or more sources of mRNA, one or more sources of RNA, one or more sources of tRNA 4324, one or more sources of amino acids 4326 one or more sources of nucleotides 4327, one or more sources of tRNA charging components 4325, and/or one or more sources of nucleic acid synthesis components 4328. In some embodiments, one or more sourcing units 432 include one or more of one or more sources of tRNA 4324 (including, but not limited to, natural, unnatural, and arbitrary tRNA), one or more sources of amino acids 4326 (including, but not limited to, natural, unnatural, and arbitrary amino acids), and/or one or more sources of tRNA charging components 4325 (including, but not limited to, natural, unnatural, and arbitrary).

Unit 4320 is optionally one or more sourcing units containing one or more sources of charged tRNA, and is optionally operable to provide and/or to remove one or more charged tRNA and/or released tRNA to and/or from one or more identifiable locations. In some embodiments, one or more apparatus includes one or more or two or more sources of charged tRNA 4320 optionally operable to provide two or more charged tRNA to one or more identifiable locations at one or more first identifiable time intervals, and/or to remove one or more charged tRNA and/or released tRNA from one or more identifiable locations at one or more second identifiable time intervals.

In some embodiments, one or more apparatus includes two or more sources of charged tRNA 4320, wherein one or more first source of the two or more sources of charged tRNA includes a supply of one or more first type of charged tRNA, and one or more second source of the two or more sources of charged tRNA includes one or more second type of charged tRNA. In some embodiments, the one or more first type of charged tRNA is different from, or the same as, the one or more second type of charged tRNA. In some embodiments, one or more apparatus further includes one or more third source of the two or more sources of charged tRNA that includes a supply of one or more third type of charged tRNA. In some embodiments, the one or more third type of charged tRNA is different from, or the same as, the one or more first type of charged tRNA and/or the one or more second type of charged tRNA. In some embodiments, the first type of charged tRNA includes one or more natural charged tRNA, one or more unnatural charged tRNA, and/or one or more arbitrary charged tRNA and the second type of charged tRNA includes one or more natural charged tRNA, one or more unnatural charged tRNA, and/or one or more arbitrary charged tRNA. In some embodiments, the two or more sources of charged tRNA include one or more fluid flows.

Unit 4322 is optionally one or more sourcing units containing one or more sources of biological assemblers, and is optionally operable to provide and/or to remove one or more biological assemblers to and/or from one or more identifiable locations. In some embodiments, one or more apparatus includes one or more sources of biological assemblers 4322 optionally operable to provide and/or to remove one or more biological assemblers to and/or from one or more identifiable locations at one or more third identifiable time intervals. In some embodiments, one or more apparatus includes one or more sources of biological assemblers 4322, wherein one or more first source of the one or more biological assemblers includes a supply of one or more first type of biological assemblers, and one or more second source of the one or more sources of biological assemblers includes one or more second type of biological assemblers. In some embodiments, the one or more first type of biological assemblers is different from, or the same as, the one or more second type of biological assemblers. In some embodiments, one or more apparatus further includes one or more third source of the one or more sources of biological assemblers that includes a supply of one or more third type of biological assemblers. In some embodiments, the one or more third type of biological assemblers is different from, or the same as, the one or more first type of biological assemblers and/or the one or more second type of biological assemblers. In some embodiments, the first type of biological assemblers is prokaryotic, and the second type of biological assemblers in eukaryotic. In some embodiments, the one or more sources of biological assemblers include one or more fluid flows.

Unit 4321 is optionally one or more sourcing units containing one or more sources of nucleic acids, and is optionally operable to provide and/or to remove one or more nucleic acids to and/or from one or more identifiable locations. In some embodiments, one or more apparatus includes one or more sources of nucleic acids 4321 optionally operable to provide and/or to remove one or more nucleic acids to and/or from one or more identifiable locations at one or more fourth identifiable time intervals. In some embodiments, one or more apparatus includes one or more sources of nucleic acids 4321, wherein one or more first source of the one or more nucleic acids includes a supply of one or more first type of nucleic acids, and one or more second source of the one or more sources of nucleic acids includes one or more second type of nucleic acids. In some embodiments, the one or more first type of nucleic acids is different from, or the same as, the one or more second type of nucleic acids. In some embodiments, one or more apparatus further includes one or more third source of the one or more sources of nucleic acids that includes a supply of one or more third type of nucleic acids. In some embodiments, the one or more third type of nucleic acids is different from, or the same as, the one or more first type of nucleic acids and/or the one or more second type of nucleic acids. In some embodiments, the first type of nucleic acids is DNA and the second type of nucleic acids is RNA. In some embodiments, the one or more sources of nucleic acids are one or more sources of RNA, one or more sources of mRNA, one or more sources of DNA, and/or one or more sources of cDNA. In some embodiments, the one or more sources of nucleic acids include one or more fluid flows. In some embodiments, the one or more third locations are included in the two or more first locations and/or are optionally the same as one or more second locations.

Unit 4323 is optionally one or more sourcing units containing one or more sources of biological assembler components, and is optionally operable to provide and/or to remove one or more biological assembler components to and/or from one or more identifiable locations. In some embodiments, one or more apparatus includes one or more sources of biological assembler components 4323, each source positioned to provide one or more biological assembler components to one or more fourth locations. In some embodiments, one or more of the one or more sources of biological assembler components includes one or more fluid flows. In some embodiments, the one or more fourth locations are one or more temporal-spatial locations and/or are moving along a predictable time or other sequential path. In some embodiments, the one or more fourth locations are optionally the same as the one or more sources of one or more biological assemblers and/or the one or more first locations. In some embodiments, the one or more sources of biological assembler components are positioned to provide the biological assembler components to one or more sources of one or more biological assemblers and/or the one or more first locations.

In some embodiments, one or more apparatus includes one or more sources of biological assembler components 4323, wherein one or more first source of the one or more biological assembler components includes a supply of one or more first type of biological assembler components, and one or more second source of the one or more sources of biological assembler components includes one or more second type of biological assembler components. In some embodiments, the one or more first type of biological assembler components is different from, or the same as, the one or more second type of biological assembler components. In some embodiments, one or more apparatus further includes one or more third source of the one or more sources of biological assembler components that includes a supply of one or more third type of biological assembler components. In some embodiments, the one or more third type of biological assembler components is different from, or the same as, the one or more first type of biological assembler components and/or the one or more second type of biological assembler components. In some embodiments, the one or more sources of biological assembler components include one or more fluid flows.

In some embodiments, one or more apparatus includes one or more sources of tRNA 4324, each source positioned to provide one or more tRNA to one or more second locations; one or more sources of amino acids 4326, each source positioned to provide one or more amino acids to the one or more second locations; and one or more sources of tRNA charging components 4325, each source positioned to provide one or more tRNA charging components to the one or more second locations. In some embodiments, one or more of the one or more sources of tRNA, the one or more sources of amino acids, and/or the one or more sources of tRNA charging components include one or more fluid flows. In some embodiments, the one or more second locations are one or more temporal-spatial locations and/or the one or more temporal-spatial locations are moving along a predictable time or other sequential path. In some embodiments, the one or more second locations are positioned to provide charged tRNA to the two or more sources of charged tRNA. In some embodiments, the one or more second locations are one or more sources of charged tRNA.

Unit 4324 is optionally one or more sourcing units containing one or more sources of tRNA, and is optionally operable to provide and/or to remove one or more tRNA to and/or from one or more identifiable locations. In some embodiments, one or more first source of the one or more sources of tRNA includes a supply of one or more first type of tRNA and one or more second source of the one or more sources of tRNA includes a supply of one or more second type of tRNA. In some embodiments, the one or more first type of tRNA is different from, or the same as, the one or more second type of tRNA. In some embodiments, the one or more first type of tRNA includes one or more natural tRNA, and the one or more second type of tRNA includes one or more unnatural tRNA.

Unit 4326 is optionally one or more sourcing units containing one or more sources of amino acids, and is optionally operable to provide and/or to remove one or more amino acids to and/or from one or more identifiable locations. In some embodiments, one or more first source of the one or more sources of amino acids includes a supply of one or more first type of amino acids and one or more second source of the one or more sources of amino acids includes a supply of one or more second type of amino acids. In some embodiments, the one or more first type of amino acids is different from, or the same as, the one or more second type of amino acids. In some embodiments, the one or more first type of amino acids includes one or more natural amino acids, and the one or more second type of amino acids includes one or more unnatural amino acids.

Unit 4325 is optionally one or more sourcing units containing one or more sources of tRNA charging components, and is optionally operable to provide and/or to remove one or more tRNA charging components to and/or from one or more identifiable locations. In some embodiments, one or more first source of the one or more sources of tRNA charging components includes a supply of one or more first type of tRNA charging components, and one or more second source of the one or more sources of tRNA charging components includes a supply of one or more second type of tRNA charging components. In some embodiments, the one or more first type of tRNA charging components is different from, or the same as, the one or more second type of tRNA charging components. In some embodiments, the one or more first type of tRNA charging components include one or more tRNA synthetases, and the one or more second type of tRNA charging components includes one or more non-natural tRNA charging components. In some embodiments, the first type of tRNA charging components include one or more prokaryotic tRNA synthetases, and the second type of tRNA charging components include one or more eukaryotic tRNA synthetases.

Unit 4327 is optionally one or more sourcing units containing one or more sources of nucleotides, and is optionally operable to provide and/or to remove one or more nucleotides to and/or from one or more identifiable locations. Unit 4328 is optionally one or more sourcing units containing one or more sources of nucleic acid synthesis components, and is optionally operable to provide and/or to remove one or more nucleic acid synthesis components to and/or from one or more identifiable locations. In some embodiments, one or more apparatus includes one or more sources of nucleotides 4327, each source positioned to provide one or more nucleotides to one or more third locations, and one or more sources of nucleic acid synthesis components 4328, each source positioned to provide one or more nucleic acid synthesis components to the one or more third locations. In some embodiments, one or more of the one or more sources of nucleotides, each source positioned to provide one or more nucleotides to one or more third locations, and one or more sources of nucleic acid synthesis components, each source positioned to provide one or more nucleic acid synthesis components to the one or more third locations include fluid flows. In some embodiments, the one or more third locations is one or more temporal-spatial locations and/or the one or more temporal-spatial locations are moving along a predictable time or other sequential path. In some embodiments, the one or more third locations are positioned to provide nucleic acids to one or more sources of nucleic acids. In some embodiments, the one or more third locations are one or more sources of nucleic acids 4321.

In one aspect, the disclosure is drawn to one or more apparatus comprising two or more sources of charged tRNA, each source positioned to sequentially provide one or more charged tRNA to one or more first locations. In some embodiments, one or more apparatus includes two or more sources of charged tRNA 4320, each source positioned to sequentially provide one or more charged tRNA to one or more first locations, and optionally to remove one or more charged tRNA and/or one or more tRNA from one or more first locations. In some embodiments, one or more apparatus includes two or more sources of charged tRNA 4320, each source positioned to sequentially provide one or more charged tRNA to one or more first locations containing one or more biological assemblers, and optionally to remove one or more charged tRNA and/or one or more tRNA from one or more first locations containing one or more biological assemblers.

In some embodiments, one or more apparatus includes two or more sources of charged tRNA 4320, each source positioned to sequentially provide one or more charged tRNA to one or more first locations and optionally to remove one or more charged tRNA and/or one or more tRNA from one or more first locations; and one or more sources of biological assemblers 4322. In some embodiments, one or more apparatus includes two or more sources of charged tRNA 4320, each source positioned to sequentially provide one or more charged tRNA to one or more first locations and optionally to remove one or more charged tRNA and/or one or more tRNA from one or more first locations; and one or more sources of biological assemblers 4322, each source positioned to provide, and optionally to remove, one or more biological assemblers to/from the one or more first locations. In some embodiments, the one or more biological assemblers are affixed.

In some embodiments, one or more apparatus includes two or more sources of charged tRNA 4320, each source positioned to sequentially provide one or more charged tRNA to one or more first locations at one or more first identifiable time intervals, and optionally to remove one or more charged tRNA and/or one or more tRNA from one or more first locations at one or more second identifiable time intervals. In some embodiments, one or more apparatus includes two or more sources of charged tRNA 4320, each source positioned to sequentially co-localize one or more charged tRNA with one or more first locations containing one or more biological assemblers at one or more first identifiable time intervals, and optionally to remove and/or separate one or more charged tRNA and/or one or more tRNA from one or more first locations containing one or more biological assemblers at one or more second identifiable time intervals.

In some embodiments, one or more apparatus includes two or more sources of charged tRNA 4320, each source positioned to sequentially provide one or more charged tRNA to one or more first locations at one or more first identifiable time intervals, and optionally to remove one or more charged tRNA and/or one or more tRNA from one or more first locations at one or more second identifiable time intervals; and one or more sources of biological assemblers 4322. In some embodiments, one or more apparatus includes two or more sources of charged tRNA 4320, each source positioned to sequentially provide one or more charged tRNA to one or more first locations at one or more first identifiable time intervals, and optionally to remove one or more charged tRNA and/or one or more tRNA from one or more first locations at one or more second identifiable time intervals; and one or more sources of biological assemblers 4322, each source positioned to provide, and optionally to remove, one or more biological assemblers to/from the one or more first locations at one or more third identifiable time intervals. In some embodiments, the one or more biological assemblers are affixed.

In some embodiments, one or more apparatus includes two or more sources of charged tRNA, each source further positioned to provide, optionally sequentially, two or more charged tRNA to one or more first locations, and further includes one or more fluid flows. In some embodiments, the one or more fluid flows provide, optionally sequentially, the two or more charged tRNA to the one or more locations, and optionally remove, optionally sequentially, one or more charged tRNA and/or one or more tRNA from the one or more first locations. In some embodiments, the one or more fluid flows provide, optionally sequentially, the one or more biological assemblers to the one or more locations, and optionally remove, optionally sequentially, the one or more biological assemblers from the one or more first locations.

In one aspect, the disclosure is drawn to one or more apparatus comprising two or more sources of charged tRNA; and one or more sources of biological assemblers, each source positioned to sequentially provide one or more biological assemblers to two or more first locations, and to optionally remove, optionally sequentially, the one or more biological assemblers from the two or more first locations. In some embodiments, one or more apparatus includes two or more sources of charged tRNA 4320, each source positioned to provide, optionally sequentially, one or more charged tRNA to one or more second locations, and optionally to remove, optionally sequentially, one or more charged tRNA and/or one or more tRNA from one or more second locations; and one or more sources of biological assemblers 4322, each source positioned to sequentially provide one or more biological assemblers to two or more first locations and optionally to remove, optionally sequentially, the one or more biological assemblers from the two or more first locations. In some embodiments, one or more apparatus includes two or more sources of charged tRNA 4320, each source positioned to affix, optionally sequentially, one or more charged tRNA at one or more second locations. In some embodiments, one or more of the two or more charged tRNA are affixed optionally at the one or more second locations.

In some embodiments, one or more apparatus includes one or more sources of biological assemblers 4322 and/or two or more sources of charged tRNA 4320 each including one or more fluid flows. In some embodiments, one or more apparatus further includes one or more fluid flows, wherein one or more of the one or more fluid flows optionally sequentially provides the one or more biological assemblers to each of the two or more first locations and optionally sequentially removes the one or more biological assemblers from each of the two or more first locations. In some embodiments, one or more apparatus further includes one or more fluid flows, wherein one or more of the one or more fluid flows optionally sequentially provides the one or more charged tRNA to each of the two or more second locations and optionally sequentially removes the one or more charged tRNA and/or tRNA from each of the two or more second locations.

In some embodiments, one or more apparatus includes two or more sources of charged tRNA; and one or more sources of biological assemblers, each source positioned to sequentially provide one or more biological assemblers to two or more first locations at one or more first identifiable time intervals, and to optionally remove, optionally sequentially, the one or more biological assemblers from the two or more first locations at one or more second identifiable time intervals. In some embodiments, one or more apparatus further include two or more sources of charged tRNA 4320, each source positioned to provide one or more charged tRNA to one or more second locations at one or more third identifiable time intervals, and optionally to remove one or more charged tRNA from one or more second locations at one or more fourth identifiable time intervals.

In some embodiments, the first locations and/or second locations are one or more temporal-spatial locations and/or are moving along a predictable time or other sequential path. In some embodiments, the two or more first locations are the two or more sources of charged tRNA. In some embodiments, one or more of the one or more second locations are one or more of the one or more first locations.

Figure 4:
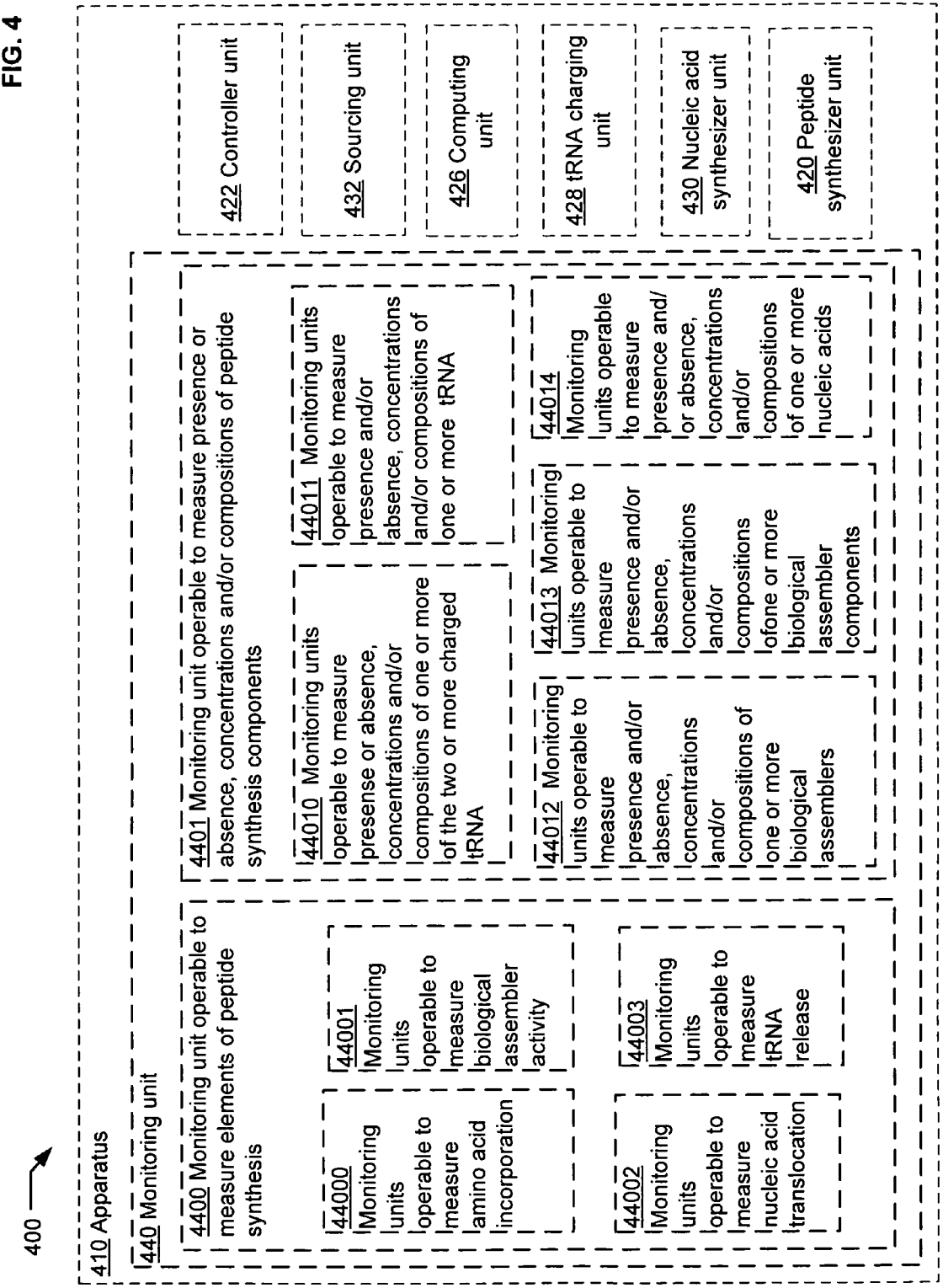
FIG. 4 shows schematics of illustrative embodiments of the apparatus of FIG. 1, with illustrative examples of a monitoring unit.

FIG. 4 shows a schematic 400 of illustrative embodiments of the apparatus 410 of FIG. 1, with specific illustrative embodiments of one or more monitoring units 440, including unit 4400 and unit 4401. In some embodiments, one or more apparatus includes, but is not limited to, one or more peptide synthesizer units 420 and one or more monitoring units 440. In some embodiments, the one or more peptide synthesizer units 420 and the one or more monitoring units 440 are the same one or more units. In some embodiments, one or more apparatus includes, but is not limited to one or more peptide synthesizer units 420, one or more sourcing units 432, and one or more monitoring units 440. In some embodiments, the one or more peptide synthesizer units 420, one or more sourcing units 432, and the one or more monitoring units 440 are the same unit.

Unit 4400 is optionally one or more monitoring units operable to measure one or more elements of peptide synthesis. Specific illustrative embodiments of unit 4400, include but are not limited to, one or more monitoring units operable to measure amino acid incorporation 44000, one or more monitoring units operable to measure biological assembler activity 44001, one or more monitoring units operable to measure nucleic acid translocation 44002, and/or one or more monitoring units operable to measure tRNA release 44003.

Unit 4401 is optionally one or more monitoring units, operable to measure presence and/or absence, concentration, and/or composition of one or more peptide synthesis components. Specific illustrative embodiments of unit 4401 include, but are not limited to, unit 44010, unit 44011, unit 44012, unit 44013, and/or 44014. Unit 44010 is optionally one or more monitoring units operable to measure presence and/or absence, concentration, and/or composition of one or more of the two or more charged tRNA. Unit 44011 is optionally one or more monitoring units operable to measure presence and/or absence, concentration, and/or composition of one or more tRNA. Unit 44012 is optionally one or more monitoring units operable to measure presence and/or absence, concentration, and/or composition of one or more biological assemblers. Unit 44013 is optionally one or more monitoring units operable to measure presence and/or absence, concentration, and/or composition of one or more biological assembler components. Unit 44014 is optionally one or more monitoring units operable to measure presence and/or absence, concentration, and/or composition of one or more nucleic acids.

Figure 5:
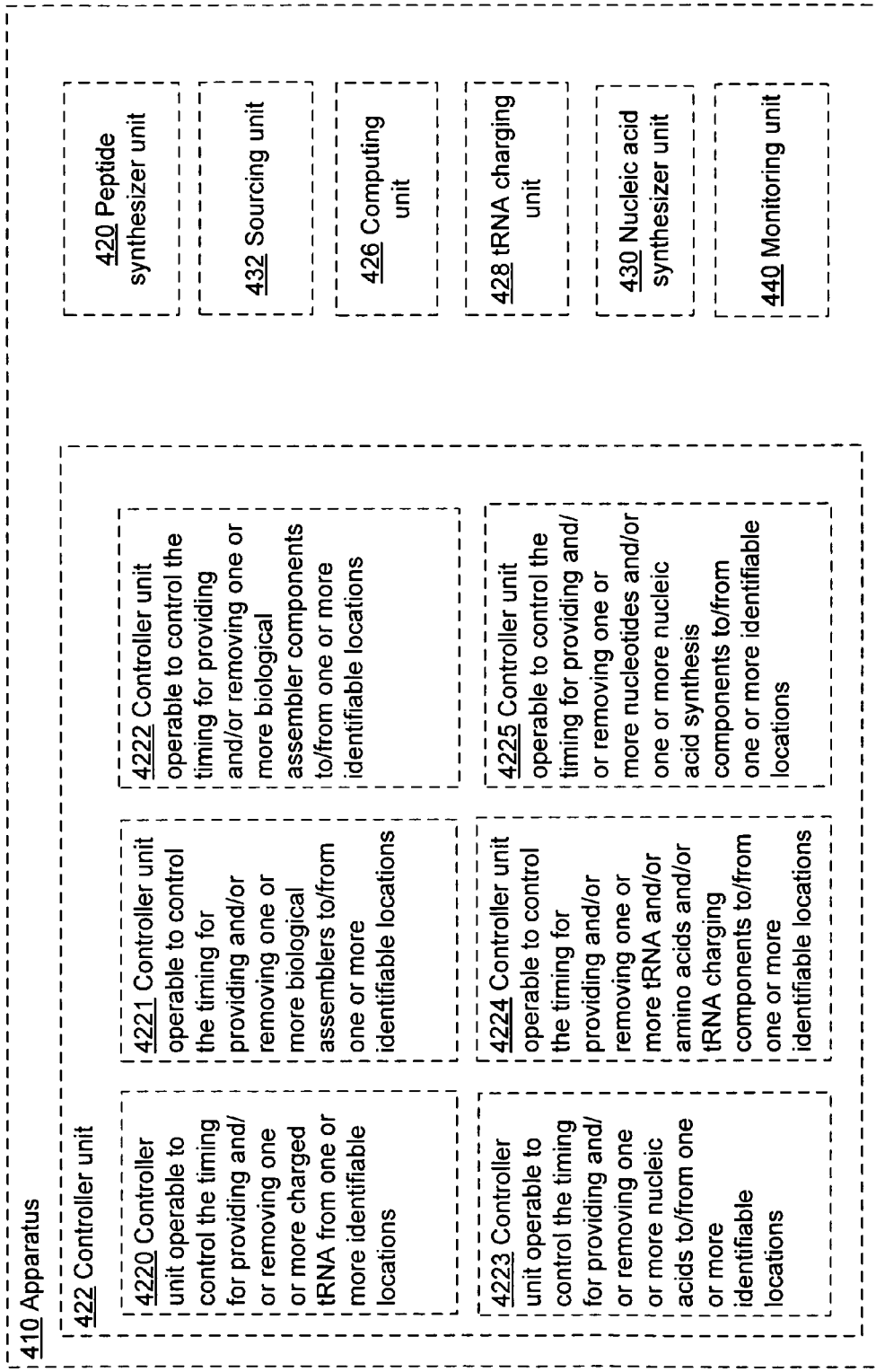
FIG. 5 shows schematics of illustrative embodiments of the apparatus of FIG. 1, with illustrative examples of a controller unit.

FIG. 5 shows a schematic 400 of illustrative embodiments of the apparatus 410 of FIG. 1, with specific illustrative embodiments of one or more controller units 422, including unit 4220, unit 4221, unit 4222, unit 4223, unit 4224, and unit 4225, wherein one or more of these units are optionally the same unit. In some embodiments, one or more apparatus includes, but is not limited to, one or more peptide synthesizer units 420 and one or more controller units 422. In some embodiments, the one or more peptide synthesizer units 420 and the one or more controller units 422 are the same one or more units. In some embodiments, one or more apparatus includes, but is not limited to one or more peptide synthesizer units 420, one or more sourcing units 432, one or more controller units 422 and one or more monitoring units 440. In some embodiments, the one or more peptide synthesizer units 420, one or more sourcing units 432, the one or more controller units 422 and the one or more monitoring units 440 are the same unit. In some embodiments, the one or more controller units 422 control the activity of the one or more units of one or more apparatus 410.

In some embodiments, one or more controller units 422 are operable to control the timing and/or the order for providing and/or co-localizing one or more peptide synthesis components at one or more identifiable locations, and optionally further operable to control the timing and/or the order for removing and/or separating one or more peptide synthesis components from one or more identifiable locations. The one or more peptide synthesis components include, but are not limited to, one or more charged tRNA, one or more tRNA, one or more biological assemblers, one or more biological assembler components, one or more nucleic acids and/or one or more nucleic acid synthesizing components.

In some embodiments, one or more controller units 422 are further operable to control an order and/or timing for providing and/or co-localizing one or more charged tRNA assembly components at one or more identifiable locations, and optionally further operable to control the timing and/or the order for removing and/or separating one or more charged tRNA assembly components from one or more identifiable locations. The one or more charged tRNA assembly components include, but are not limited to, one or more tRNA, one or more amino acids, and/or one or more tRNA charging components.

In some embodiments, one or more controller units 422 are further operable to control an order and/or timing for providing and/or co-localizing one or more nucleic acid assembly components at one or more identifiable locations, and optionally further operable to control the timing and/or the order for removing and/or separating one or more nucleic acid assembly components from one or more identifiable locations. The one or more nucleic acid assembly components include, but are not limited to, one or more nucleotides, and/or one or more nucleic acid synthesis components.

In some embodiments, the timing is at least partially based on the mechanism of peptide synthesis performed by the apparatus. Mechanisms of peptide synthesis include, but are not limited to, charged tRNA being provided sequentially to one or more locations, charged tRNA being provided sequentially to affixed biological assemblers; biological assemblers being provided sequentially to affixed charged tRNA; and/or biological assemblers and charged tRNA being co-localized at one or more locations. Depending on the mechanism of peptide synthesis, the timing related to providing/removing charged tRNA and/or the timing related to providing/removing biological assemblers, for example, optionally changes. Timing for each element may be different, and may change depending on the mechanism of synthesis and/or the biological synthesis components.

In some embodiments, the timing includes, but is not limited to, sequential timing, fixed timing, variable timing, predicted timing, and data-driven timing. In some embodiments, the timing is one or more identifiable time intervals. In some embodiments, the one or more identifiable time intervals are from approximately 0.001 seconds to 0.1 seconds and/or approximately 0.01 seconds, or other appropriate time intervals described elsewhere.

In some embodiments, the order and/or the timing for providing, co-localizing, removing and/or separating one or more peptide synthesis components is at least partially based on a target peptide sequence and/or a nucleic acid protein coding sequence. In some embodiments, the order and/or the timing for providing, co-localizing, removing and/or separating one or more peptide synthesis components is at least partially based on a predicted rate of incorporation of two or more amino acids into one or more peptides, a predicted rate of activity of one or more biological assemblers, a predicted rate of translocation of one or more nucleic acids, and/or a predicted rate of release of tRNA.

In some embodiments, one or more controller units is operable to control the order and/or the timing for providing, co-localizing, removing and/or separating one or more peptide synthesis components at least partially based on monitoring of amino acid incorporation into one or more peptides, biological assembler activity, nucleic acid translocation, and/or tRNA release. In some embodiments, one or more monitoring units 440 are operable to perform the monitoring of amino acid incorporation into one or more peptides, biological assembler activity, nucleic acid translocation, and/or tRNA release. In some embodiments, one or more of the one or more monitoring units 440 and one or more of the one or more controller units 422 are the same units.

In some embodiments, one or more controller units 422 is operable to control the order and/or the timing for providing, co-localizing, removing and/or separating one or more peptide synthesis components at least partially based on measurements including, but not limited to, availability of one or more nucleic acid codons, concentrations of one or more of the two or more charged tRNA or the one or more tRNA, presence or absence of one or more of the two or more charged tRNA or the one or more tRNA, or presence or absence of one or more anti-codons on one or more of the two or more charged tRNA or the one or more tRNA. In some embodiments, one or more of these measurements is at least partially determined extrinsically. In some embodiments, one or more of these measurements are determined based at least partially on measurements by one or more monitoring units 440. In some embodiments, one or more of these measurements are provided in real time.

In illustrative embodiments, one or more controller units are operable to provide (and optionally to remove) two or more charged tRNA in a sequence at one or more identifiable time intervals to one or more biological assemblers at one or more identifiable locations, and are further operable to co-localize (and optionally to remove) at one or more identifiable time intervals the one or more biological assemblers at the one or more identifiable locations. The one or more identifiable time intervals are optionally different for the co-localization of the two or more charged tRNA, the co-localization of one or more biological assemblers, the removal of one or more charged tRNA and/or one or more tRNA, and/or the removal of one or more biological assemblers.

In illustrative embodiments, one or more controller units are operable to co-localize (and optionally to separate) one or more biological receptors with two or more charged tRNA in a sequence at one or more identifiable time intervals, wherein at least two of the two or more charged tRNA are at one or more different locations. The one or more identifiable time intervals are optionally different for the co-localization of the one or more biological assemblers with the two or more charged tRNA, the separation of the one or more biological assemblers from the two or more charged tRNA, the co-localization of the two or more charged tRNA at the one or more different locations and/or the removal of the two or more charged tRNA from the one or more different locations.

In illustrative embodiments, one or more controller units are operable to co-localize (and optionally to separate) two or more charged tRNA and one or more biological assemblers in a sequence at one or more identifiable locations and at one or more identifiable time intervals. The one or more identifiable time intervals are optionally different for the co-localization of two or more charged tRNA, the co-localization of one or more biological assemblers, the removal of one or more charged tRNA and/or one or more tRNA, and/or the removal of one or more biological assemblers.

Unit 4220 is optionally one or more controller units, operable to control the timing and/or order for providing and/or removing one or more or two or more charged tRNA and/or released tRNA to and/or from one or more identifiable locations. In some embodiments, one or more apparatus include, but are not limited to, one or more peptide synthesizer units and one or more controller units that are operable to control the timing for providing and optionally for removing one or more charged tRNA and/or one or more tRNA. In some embodiments, one or more of the one or more peptide synthesizer units and one or more of the one or more charged tRNA controller units are the same unit.

In some embodiments, one or more controller units are operable to control the timing and/or the order for providing, optionally sequentially, two or more charged tRNA to one or more first identifiable locations, and optionally further operable to control the timing and/or the order for removing, optionally sequentially, two or more charged tRNA and/or one or more tRNA from one or more first identifiable locations. In some embodiments, one or more controller units are operable to control the timing and/or order for sequentially co-localizing two or more charged tRNA with one or more biological assemblers, and optionally sequentially removing two or more charged tRNA and/or one or more tRNA from the one or more biological assemblers. In some embodiments, one or more controller units are operable to control the timing and/or order for sequentially co-localizing two or more charged tRNA and one or more biological assemblers, and optionally sequentially separating the two or more charged tRNA and/or one or more tRNA and the one or more biological assemblers.

Unit 4221 is optionally one or more controller units, operable to control the timing and/or order for providing and/or removing, optionally sequentially, one or more biological assemblers to and/or from one or more identifiable locations. In some embodiments, one or more apparatus include, but are not limited to, one or more peptide synthesizer units and one or more controller units that are operable to control the timing for providing and optionally for removing one or more biological assemblers. In some embodiments, one or more of the one or more peptide synthesizer units and one or more of the one or more biological assembler controller units are the same unit.

In some embodiments, one or more controller units are operable to control the timing and/or order for, optionally sequentially, co-localizing one or more biological assemblers, and optionally further operable to control the timing and/or order for, optionally sequentially, removing the one or more biological assemblers following peptide synthesis. In some embodiments, one or more controller units are operable to control the timing and/or order for, optionally sequentially, co-localizing one or more biological assemblers with two or more charged tRNA, wherein at least two of the two or more charged tRNA are at one or more different locations, and optionally further operable to control the timing and/or order for, optionally sequentially, separating the one or more biological assemblers from the two or more charged tRNA and/or one or more tRNA. In some embodiments, one or more controller units are operable to control the timing and/or order for, optionally sequentially, co-localizing one or more biological assemblers and two or more charged tRNA, and optionally further operable to control the timing and/or order for, optionally sequentially, separating the one or more biological assemblers and the two or more charged tRNA and/or one or more tRNA.

Unit 4222 is optionally one or more controller units, operable to control the timing for providing and/or removing one or more biological assembler components to and/or from one or more identifiable locations. In some embodiments, one or more apparatus includes one or more controller units to control an order and/or timing in which each source provides one or more biological assembler components to one or more fourth locations. In some embodiments, one or more apparatus include, but are not limited to, one or more peptide synthesizer units and one or more controller units that are operable to control the timing for providing and optionally for removing one or more biological assembler components. In some embodiments, one or more of the one or more peptide synthesizer units and one or more of the one or more biological assembler components controller units are the same unit.

In some embodiments, one or more controller units are operable to control the timing and/or order for providing, optionally sequentially, one or more biological assembler components, and optionally further operable to control the timing and/or order for removing one or more biological assembler components. In some embodiments, one or more controller units are operable to control the timing and/or order for, optionally sequentially, co-localizing one or more biological assembler components with two or more charged tRNA, wherein at least two of the two or more charged tRNA are at one or more different locations, and optionally further operable to control the timing and/or order for, optionally sequentially, separating the one or more biological assembler components from the two or more charged tRNA and/or one or more tRNA. In some embodiments, one or more controller units are operable to control the timing and/or order for, optionally sequentially, co-localizing one or more biological assembler components and two or more charged tRNA, and optionally further operable to control the timing and/or order for, optionally sequentially, separating the one or more biological assembler components and the two or more charged tRNA and/or one or more tRNA.

Unit 4223 is optionally one or more controller units, operable to control the timing and/or the order for providing and/or removing one or more nucleic acids to and/or from one or more identifiable locations. In some embodiments, one or more apparatus include, but are not limited to, one or more peptide synthesizer units and one or more controller units that are operable to control the timing for providing and optionally for removing one or more nucleic acids. In some embodiments, one or more of the one or more peptide synthesizer units and one or more of the one or more biological assembler components controller units are the same unit.

In some embodiments, one or more controller units are operable to control the timing and/or the order for co-localizing, optionally sequentially, one or more nucleic acids, and optionally further operable to control the timing and/or the order for removing, optionally sequentially, one or more nucleic acids. In some embodiments, one or more apparatus includes one or more controller units operable to control an order and/or timing in which each source optionally provides, optionally sequentially, one or more nucleic acids to one or more third locations, and/or optionally removes, optionally sequentially, one or more nucleic acids from one or more third locations. In some embodiments, one or more controller units are operable to control the timing and/or the order for providing and optionally for removing one or more DNA, one or more cDNA, one or more RNA, and/or one or more mRNA. In some embodiments, the one or more nucleic acids are provided to one or more identifiable locations and/or to one or more biological assemblers, or one or more biological assembler components.

Unit 4224 is optionally one or more controller units, operable to control the timing for providing and/or removing one or more tRNA, one or more amino acids, and/or one or more tRNA charging components to and/or from one or more identifiable locations. In some embodiments, one or more apparatus include, but are not limited to, one or more peptide synthesizer units and one or more controller units that are operable to control the timing for providing and optionally for removing one or more tRNA, one or more amino acids, and/or one or more tRNA charging components. In some embodiments, the one or more peptide synthesizer units and the one or more tRNA charging in controller units are the same unit. In some embodiments, one or more controller units are operable to control timing and/or order for charging one or more tRNA. In some embodiments, one or more controller units 422 include one or more first controller units 4224 operable to control one or more of an order or timing in which each source provides one or more tRNA to one or more second locations; one or more second controller units operable to control one or more of the order or the timing in which each source provides one or more amino acids to the one or more second locations; and one or more third controller units operable to control one or more of the order or the timing in which each source provides one or more tRNA charging components to the one or more second locations; and wherein one or more of the one or more first controller units are optionally the same as one or more of the one or more second controller units, and optionally the same as one or more of the one or more third controller units.

Unit 4225 is optionally one or more controller units, operable to control the timing and/or the order for providing and/or removing one or more nucleotides and/or one or more nucleic acid synthesis components to and/or from one or more identifiable locations. In some embodiments, one or more apparatus include, but are not limited to, one or more peptide synthesizer units and one or more controller units that are operable to control the timing and or the order for providing and optionally for removing one or more nucleotides and/or one or more nucleic acid synthesis components. In some embodiments, the one or more peptide synthesizer units and the one or more nucleic acid synthesis controller units are the same unit. In some embodiments, one or more controller units are operable to control the timing and/or the order for synthesizing one or more DNA, one or more cDNA, one or more RNA, and/or one or more mRNA. In some embodiments, one or more apparatus include one or more first controller units to control one or more of an order or timing in which each source provides one or more nucleotides to the one or more third locations; and one or more second controller units to control one or more of the order or the timing in which each source provides one or more nucleic acid synthesis components to the one or more third locations; wherein the one or more first controller units are optionally the same as the one or more second controller units.

Figure 6:
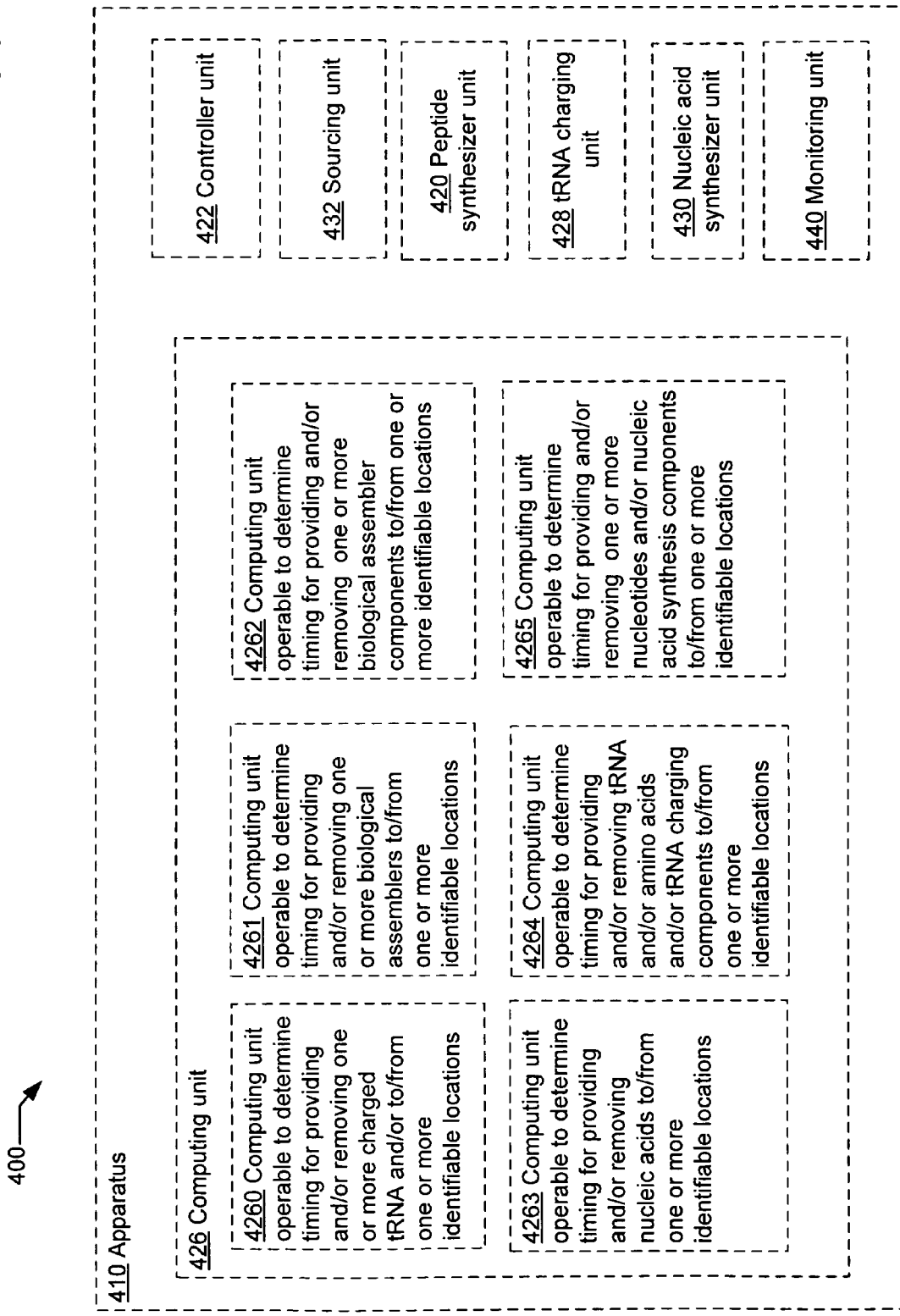
FIG. 6 shows schematics of illustrative embodiments of the apparatus of FIG. 1, with illustrative examples of a computing unit.

FIG. 6 shows a schematic 400 of illustrative embodiments of the apparatus 410 of FIG. 1, with specific illustrative embodiments of one or more computing units 426, including unit 4260, unit 4261, unit 4262, unit 4263, unit 4264, and unit 4265, wherein one or more of these units are optionally the same unit. In some embodiments, one or more apparatus include, but are not limited to, one or more peptide synthesizer units 420 and one or more computing units 426. In some embodiments, the one or more peptide synthesizer units 420 and the one or more computing units 426 are the same one or more units. In some embodiments, one or more apparatus optionally further includes, but is not limited to, one or more controller units 422, one or more sourcing units 432, and one or more monitoring units 440. In some embodiments, the one or more peptide synthesizer units 420, the one or more sourcing units 432, the one or more controller units 422, the one or more computing units 426, and the one or more monitoring units 440 are the same unit. In some embodiments one or more of the one or more controller units are optionally the same as one or more of the one or more computing units.

In some embodiments, one or more computing units 426 are operable to determine the timing and/or the order for providing and/or co-localizing one or more peptide synthesis components at one or more identifiable locations, and optionally further operable to determine the timing and/or the order for removing and/or separating one or more peptide synthesis components from one or more identifiable locations. The one or more peptide synthesis components include, but are not limited to, one or more charged tRNA, one or more tRNA, one or more biological assemblers, one or more biological assembler components, one or more nucleic acids, and/or nucleic acid synthesizing components.

In some embodiments, the timing is at least partially based on the mechanism of peptide synthesis performed by the apparatus. Mechanisms of peptide synthesis include, but are not limited to, charged tRNA being provided sequentially to one or more locations, charged tRNA being provided sequentially to affixed biological assemblers; biological assemblers being provided sequentially to affixed charged tRNA; and/or biological assemblers and charged tRNA being co-localized at one or more locations. Depending on the mechanism of peptide synthesis, the timing related to providing/removing charged tRNA and/or the timing related to providing/removing biological assemblers, for example, optionally changes. Timing for each element may be different, and may change depending on the mechanism of synthesis.

In some embodiments, the timing includes, but is not limited to, sequential timing, fixed timing, variable timing, predicted timing, and data-driven timing. In some embodiments, the timing is one or more identifiable time intervals. In some embodiments, the one or more identifiable time intervals are from approximately 0.001 seconds to 0.1 seconds and/or approximately 0.01 seconds, or other appropriate time intervals described elsewhere.

In some embodiments, the order and/or the timing for providing, co-localizing, removing and/or separating one or more peptide synthesis components is at least partially based on a target peptide sequence and/or a nucleic acid protein coding sequence. In some embodiments, the order and/or the timing for providing, co-localizing, removing and/or separating one or more peptide synthesis components is at least partially based on a predicted rate of incorporation of two or more amino acids into one or more peptides, a predicted rate of activity of one or more biological assemblers, a predicted rate of translocation of one or more nucleic acids, and/or a predicted rate of release of tRNA.

In some embodiments, one or more computing units 426 are operable to determine the order and/or the timing for providing, co-localizing, removing and/or separating one or more peptide synthesis components at least partially based on monitoring of amino acid incorporation into one or more peptides, biological assembler activity, nucleic acid translocation, and/or tRNA release. In some embodiments, one or more monitoring units 440 are operable to perform the monitoring of amino acid incorporation into one or more peptides, biological assembler activity, nucleic acid translocation, and/or tRNA release. In some embodiments, one or more of the one or more monitoring units 440 and one or more of the one or more computing units 426 are the same units.

In some embodiments, one or more computing units 426 are operable to determine the order and/or the timing for providing, co-localizing, removing and/or separating one or more peptide synthesis components at least partially based on measurements including, but not limited to, availability of one or more nucleic acid codons, concentrations of one or more of the two or more charged tRNA or the one or more tRNA, presence or absence of one or more of the two or more charged tRNA or the one or more tRNA, or presence or absence of one or more anti-codons on one or more of the two or more charged tRNA or the one or more tRNA. In some embodiments, one or more of these measurements is at least partially determined extrinsically. In some embodiments, one or more of these measurements are determined based at least partially on measurements by one or more monitoring units 440. In some embodiments, one or more of these measurements are provided in real time.

Unit 4260 is optionally one or more computing units, operable for determining the timing for providing and/or removing one or more or two or more charged tRNA and/or released tRNA to and/or from one or more identifiable locations. In some embodiments, one or more apparatus include, but are not limited to, one or more peptide synthesizer units and one or more computing units that are operable to determine the timing and/or order for providing and optionally for removing one or more charged tRNA and/or one or more tRNA. In some embodiments, one or more of the one or more peptide synthesizer units and one or more of the one or more charged tRNA computing units are the same unit.

In some embodiments, one or more computing units are operable to determine the timing and/or the order for providing, optionally sequentially, two or more charged tRNA to one or more first identifiable locations, and optionally further operable to determine the timing and/or the order for removing, optionally sequentially, two or more charged tRNA and/or one or more tRNA from one or more first identifiable locations. In some embodiments, one or more computing units are operable to determine the timing and/or order for sequentially co-localizing two or more charged tRNA with one or more biological assemblers, and optionally sequentially removing two or more charged tRNA and/or one or more tRNA from the one or more biological assemblers. In some embodiments, one or more computing units are operable to determine the timing and/or order for sequentially co-localizing two or more charged tRNA and one or more biological assemblers, and optionally sequentially separating the two or more charged tRNA and/or one or more tRNA and the one or more biological assemblers.

Unit 4261 is optionally one or more computing units operable for determining the timing and/or order for providing and/or removing one or more biological assemblers to and/or from one or more identifiable locations. In some embodiments, one or more apparatus include, but are not limited to, one or more peptide synthesizer units and one or more computing units that are operable to determine the timing for providing and optionally for removing one or more biological assemblers. In some embodiments, one or more of the one or more peptide synthesizer units and one or more of the one or more biological assembler computing units are the same unit.

In some embodiments, one or more computing units operable for determining the timing and/or order for, optionally sequentially, co-localizing one or more biological assemblers, and optionally further operable to determine the timing and/or order for, optionally sequentially, removing the one or more biological assemblers following peptide synthesis. In some embodiments, one or more computing units operable for determining the timing and/or order for, optionally sequentially, co-localizing one or more biological assemblers with two or more charged tRNA, wherein at least two of the two or more charged tRNA are at one or more different locations, and optionally further operable to determine the timing and/or order for, optionally sequentially, separating the one or more biological assemblers from the two or more charged tRNA and/or one or more tRNA. In some embodiments, one or more computing units operable for determining the timing and/or order for, optionally sequentially, co-localizing one or more biological assemblers and two or more charged tRNA, and optionally further operable to determine the timing and/or order for, optionally sequentially, separating the one or more biological assemblers and the two or more charged tRNA and/or one or more tRNA.

Unit 4262 is optionally one or more computing units operable for determining the timing and/or order for providing and/or removing one or more biological assembler components to and/or from one or more identifiable locations. In some embodiments, one or more apparatus includes one or more computing units to determine an order and/or timing in which each source provides one or more biological assembler components to one or more fourth locations. In some embodiments, one or more apparatus include, but are not limited to, one or more peptide synthesizer units and one or more computing units that are operable to determine timing and/or order for providing one or more biological assembler components to one or more identifiable locations. In some embodiments, one or more of the one or more peptide synthesizer units and one or more of the one or more biological assembler components computing units are the same unit.

In some embodiments, one or more computing units operable for determining the timing and/or order for providing, optionally sequentially, one or more biological assembler components, and optionally further operable to determine the timing and/or order for removing one or more biological assembler components. In some embodiments, one or more computing units operable for determining the timing and/or order for, optionally sequentially, co-localizing one or more biological assembler components with two or more charged tRNA, wherein at least two of the two or more charged tRNA are at one or more different locations, and optionally further operable to determine the timing and/or order for, optionally sequentially, separating the one or more biological assembler components from the two or more charged tRNA and/or one or more tRNA. In some embodiments, one or more computing units operable for determining the timing and/or order for, optionally sequentially, co-localizing one or more biological assembler components and two or more charged tRNA, and optionally further operable to determine the timing and/or order for, optionally sequentially, separating the one or more biological assembler components and the two or more charged tRNA and/or one or more tRNA.

Unit 4263 is optionally one or more computing units, operable for determining the timing and/or order for providing and/or removing one or more nucleic acids to and/or from one or more identifiable locations. In some embodiments, one or more apparatus include, but are not limited to, one or more peptide synthesizer units and one or more computing units that are operable to determine timing and/or order for providing one or more nucleic acids to one or more first identifiable locations. In some embodiments, one or more of the one or more peptide synthesizer units and one or more of the one or more nucleic acid computing units are the same unit.

In some embodiments, one or more computing units are operable to determine the timing and/or the order for co-localizing, optionally sequentially, one or more nucleic acids, and optionally further operable to determine the timing and/or the order for removing, optionally sequentially, one or more nucleic acids. In some embodiments, one or more apparatus further includes one or more computing units operable to determine the order and/or the timing in which each source optionally provides one or more nucleic acids to one or more third locations, and optionally removes one or more nucleic acids from one or more third locations. In some embodiments, one or more computing units are operable to determine the timing and/or the order for providing and optionally for removing one or more DNA, one or more cDNA, one or more RNA, and/or one or more mRNA. In some embodiments, the one or more nucleic acids are provided to one or more identifiable locations and/or to one or more biological assemblers, or one or more biological assembler components.

Unit 4264 is optionally one or more computing units operable for determining the timing and/or order for providing and/or removing one or more tRNA, one or more amino acids, and/or one or more tRNA charging components to and/or from one or more identifiable locations. In some embodiments, one or more apparatus include, but are not limited to, one or more peptide synthesizer units and one or more computing units that are operable to determine timing and/or order for providing one or more tRNA, one or more amino acids, and/or one or more tRNA charging components to one or more first identifiable locations. In some embodiments, the one or more peptide synthesizer units and the one or more tRNA charging controller units are the same unit. In some embodiments, one or more computing units are operable to determine timing and/or order for charging one or more tRNA. In some embodiments, one or more apparatus include one or more first computing units to determine one or more of an order or timing in which each source provides one or more tRNA to the one or more second locations; one or more second computing units to determine one or more of the order or the timing in which each source provides one or more amino acids to the one or more second locations; and one or more third computing units to determine one or more of the order or the timing in which each source provides the one or more tRNA charging components to the one or more second locations; and wherein one or more of the one or more first computing units are optionally the same as the one or more second computing units, and optionally the same as the one or more third computing units.

Unit 4265 is optionally one or more computing units, operable for determining the timing and/or order for providing and/or removing one or more nucleotides and/or one or more nucleic acid synthesis components to and/or from one or more identifiable locations. In some embodiments, one or more apparatus 410 include, but are not limited to, one or more peptide synthesizer units 420 and one or more computing units that are operable to determine timing and/or order for providing one or more nucleotides and/or one or more nucleic acid synthesis components 4265 to one or more identifiable locations. In some embodiments, the one or more peptide synthesizer units 420 and the one or more nucleic acid synthesis computing units 4265 are the same unit. In some embodiments, one or more computing units 4265 are operable to determine timing and/or order for synthesizing one or more DNA, one or more cDNA, one or more RNA, and/or one or more mRNA. In some embodiments, one or more apparatus include one or more first computing units to determine one or more of an order or timing in which each source provides one or more nucleotides to the one or more third locations; and one or more second computing units to determine one more of the order or the timing in which each source provides one or more nucleic acid synthesis components to the one or more third locations; wherein the one or more first computing units are optionally the same as the one or more second computing units.

In some embodiments, one or more apparatus 410 include, but are not limited to, one or more tRNA charging units 428 operable to charge one or more tRNA with one or more amino acids. In some embodiments, one or more apparatus 410 include, but are not limited to, one or more peptide synthesizer units 420 and one or more tRNA charging units 428. In some embodiments, one or more of the one or more tRNA charging units 428 and one or more of the one or more peptide synthesizer units 420 are the same unit. In some embodiments, one or more tRNA charging units 428 are operable to co-localize one or more tRNA, one or more amino acids, and one or more tRNA charging components in one or more third identifiable locations. In some embodiments, the one or more tRNA charging units 428 are operable to provide one or more charged tRNA to one or more peptide synthesizer units and/or to one or more sources of charged tRNA 4320. In some embodiments, one or more of the one or more third identifiable locations are the same as one or more of the one or more first locations and/or the one or more second locations. In some embodiments, one or more of the one or more third identifiable locations are the same as one or more sources of charged tRNA 4320. In some embodiments, one or more third identifiable locations are located in one or more peptide synthesizer units 420. In some embodiments, the one or more tRNA charging units 428 include one or more fluid flows.

In some embodiments, one or more apparatus include, but are not limited in, one or more peptide synthesizer units 420 and one or more tRNA charging units 428 that are operable to charge one or more natural tRNA with one or more amino acids, one or more unnatural tRNA with one or more amino acids, one or more arbitrary tRNA with one or more amino acids, one or more tRNA with one or more natural amino acids, one or more tRNA with one or more unnatural amino acids, and/or one or more tRNA with one or more arbitrary amino acids. In some embodiments, the one or more apparatus 410 include, but are not limited to one or more sources of tRNA 4324, one or more sources of amino acids 4326, and/or one or more sources of tRNA charging components 4325.

In some embodiments, one or more apparatus include one or more nucleic acid synthesizer units 430 operable to synthesize nucleic acids. In some embodiments, one or more apparatus 410 include, but are not limited to, one or more peptide synthesizer units 420 and one or more nucleic acid synthesizer units 430. In some embodiments, one or more of the one or more peptide synthesizer units 420 and one or more of the one or more nucleic acid synthesizer units 430 are the same unit. In some embodiments, one or more nucleic acid synthesizer units 430 are operable to synthesize one or more RNA, one or more mRNA, one or more cDNA, and/or one or more DNA. In some embodiments, one or more nucleic acid synthesizer units 430 are operable to co-localize one or more nucleotides and/or one or more nucleic acid synthesis components in one or more fourth identifiable locations. In some embodiments, one or more nucleic acid synthesis components include, but are not limited to, one or more DNA synthesis components, one or more cDNA synthesis components, one or more RNA synthesis components, and one or more mRNA synthesis components.

In some embodiments, one or more of the apparatus 410 include, but are not limited to, one or more nucleic acid synthesizer units 430 operable to provide one or more nucleic acids to one or more peptide synthesizer units 420. In some embodiments, one or more of the one or more fourth identifiable locations are optionally the same as one or more of the one or more first identifiable locations, and/or one or more sources of nucleic acids 4321. In some embodiments one or more fourth identifiable locations are located in one or more peptide synthesizer units 420. In some embodiments, the one or more nucleic acid synthesizer units 430 include one or more fluid flows.

In one aspect, the disclosure is drawn to one or more methods comprising receiving a first input associated with a first possible dataset, the first possible dataset including data representative of one or more charged tRNA sequences; and determining temporal-spatial parameters for synthesizing one or more peptides based on a first possible data set. One or more of these methods may be used as part of one or more methods of target peptide synthesis and/or implemented on one or more apparatus 410 for target peptide synthesis.

Figure 7:
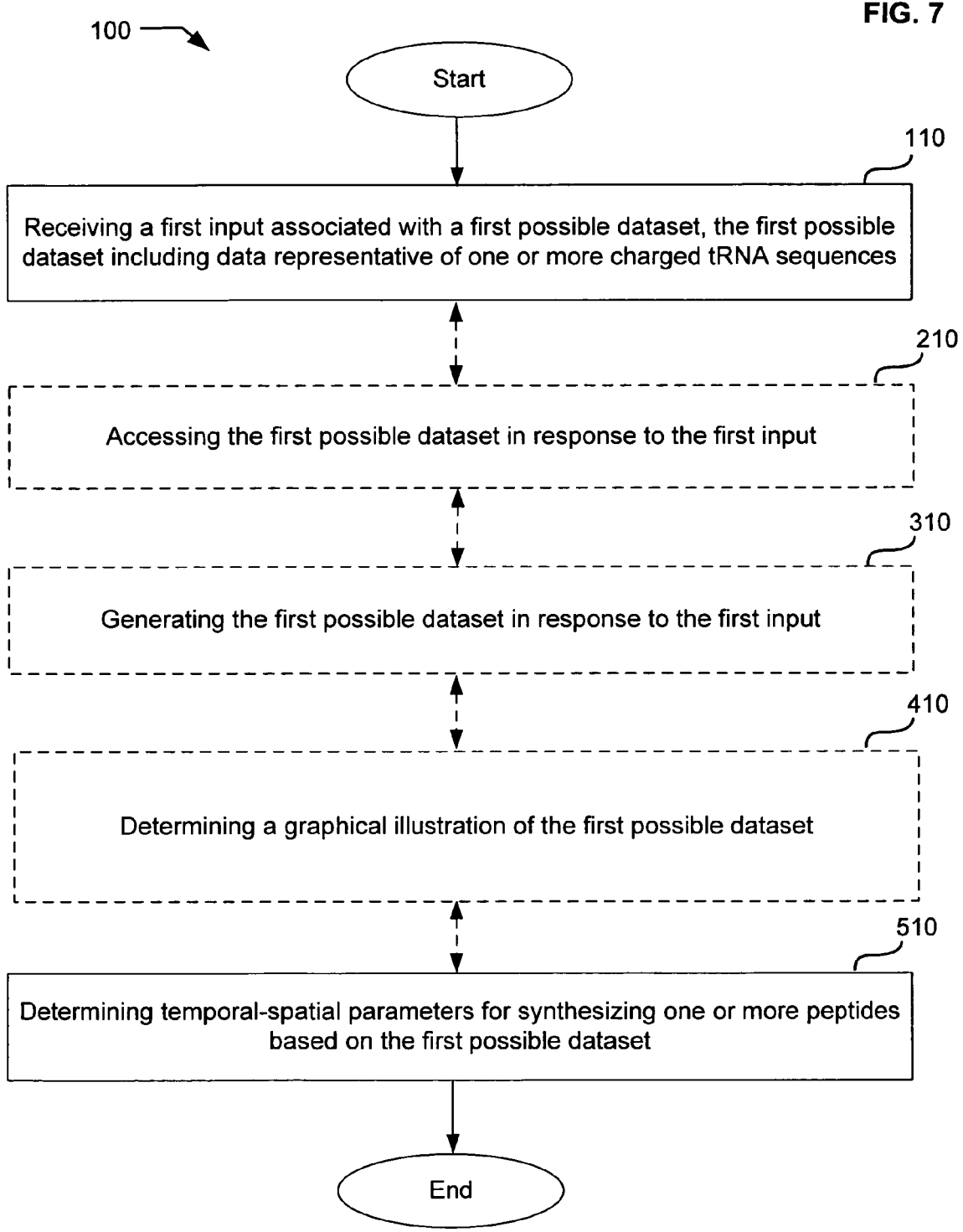
FIG. 7 shows an operational flow representing illustrative embodiments of operations related to determining temporal-spatial parameters for synthesizing one or more peptides based on a first possible dataset.

FIG. 7 shows an operational flow 100 representing illustrative embodiments of operations related to determining temporal-spatial parameters for synthesizing one or more peptides based on a first possible dataset. In FIG. 7, and in the following figures that include various illustrative embodiments of operational flows, discussion and explanation may be provided with respect to apparatus and methods described herein, and/or with respect to other examples and contexts. The operational flows may also be executed in a variety of other contexts and environments, and or in modified versions of those described herein. In addition, although some of the operational flows are presented in sequence, the various operations may be performed in various repetitions, concurrently, and/or in other orders than those that are illustrated.

After a start operation, the operational flow 100 moves to a receiving operation 110 where receiving a first input may be associated with a first possible dataset, the first possible dataset including data representative of one or more charged tRNA sequences. For example, a first input may include data representative of a target peptide sequence, a target nucleic acid sequence, a target biological assembler, and/or target biological assembler components. A first input may also include data representative of the identity and sequence of charged tRNA.

An optional accessing operation 210 accesses the first possible dataset in response to the first input. For example, data representative of a target peptide sequence, a target nucleic acid sequence, a target biological assembler, and/or target biological assembler components may be accessed. Data representative of the identity and sequence of charged tRNA may also be accessed.

An optional generating operation 310 generates the first possible dataset in response to the first input. For example, data representative of a target peptide sequence, a target nucleic acid sequence, a target biological assembler, and/or target biological assembler components may be generated. Data representative of the identity and sequence of charged tRNA may also be generated.

An optional determining operation 410 determines a graphical illustration of the first possible dataset. For example, data representative of a target peptide sequence, a target nucleic acid sequence, a target biological assembler, and/or target biological assembler components may be graphically represented. Data representative of the identity and sequence of charged tRNA may also be graphically represented.

Then, a determining operation 510, determines temporal-spatial parameters for synthesizing one or more peptides based on the first possible dataset. For example, data representative of temporal-spatial parameters for synthesizing one or more peptides based on a target peptide sequence, a target nucleic acid sequence, a target biological assembler, and/or target biological assembler components may be determined. Data representative of temporal-spatial parameters for synthesizing one or more peptides based on the sequence of charged tRNA may also be determined.

Operations 110 to 510 may be performed with respect to a digital representation (e.g. digital data) of, for example, data representative of a target peptide sequence, a target nucleic acid sequence, a target biological assembler, and/or target biological assembler components. The logic may accept a digital or analog (for conversion into digital) representation of an input and/or provide a digitally-encoded representation of a graphical illustration, where the input may be implemented and/or accessed locally or remotely.

Operations 110 to 510 may be performed related to either a local or a remote storage of the digital data, or to another type of transmission of the digital data. In addition to inputting, accessing querying, recalling, calculating, determining or otherwise obtaining the digital data, operations may be performed related to storing, assigning, associating, displaying or otherwise archiving the digital data to a memory, including for example, sending and/or receiving a transmission of the digital data from a remote memory. Accordingly, any such operations may involve elements including at least an operator (e.g. human or computer) directing the operation, a transmitting computer, and/or receiving computer, and should be understood to occur in the United States as long as at least one of these elements resides in the United States.

Figure 8:
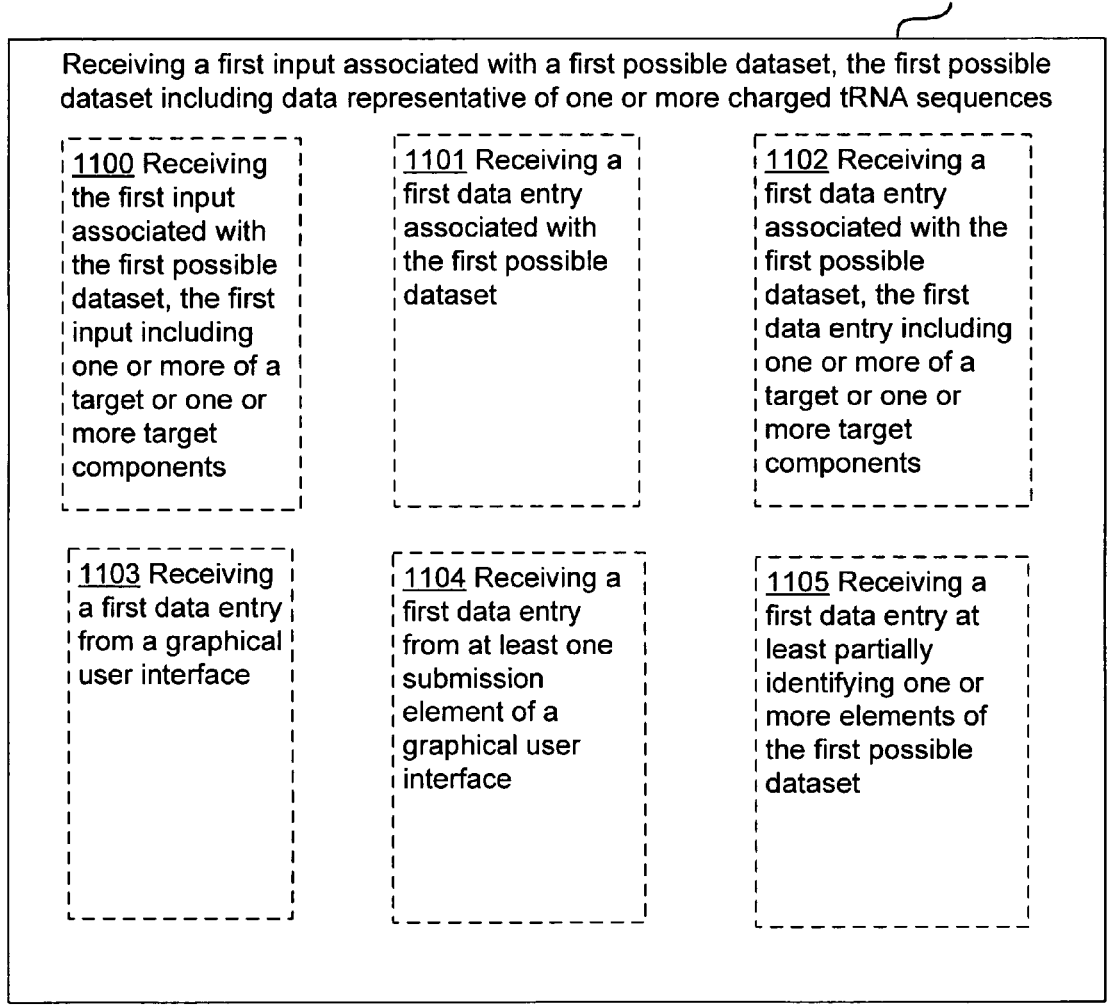
FIG. 8 shows optional embodiments of the operational flow of FIG. 7.

FIG. 8 illustrates optional embodiments of the operational flow 100 of FIG. 7. FIG. 8 shows illustrative embodiments of the receiving operation 110, receiving a first input associated with a first possible dataset, the first possible dataset including data representative of one or more charged tRNA sequences, including operations receiving types of inputs and data entry and may include at least one additional operation. Receiving operations may optionally include, but are not limited to, operation 1100, operation 1101, operation 1102, operation 1103, operation 1104, and/or operation 1105.

At the optional operation 1100, the first input may include one or more of a target or one or more target components. At the optional operation 1101, a first data entry associated with a first possible dataset may be received. At the optional operation 1105, a first data entry at least partially identifying one or more elements of the first possible dataset may be received.

At the optional operation 1102, a first data entry associated with a first possible dataset may be received that may include one or more of a target or one or more target components. A first data entry associated with a first possible dataset may be received that may include at least partially identifying one or more of a target structure, a peptide sequence, a nucleic acid sequence, a biological assembler, one or more biological assembler components, one or more amino acids, one or more charged tRNA, or one or more tRNA. A first data entry associated with a first possible dataset may be received that may include receiving a first data entry at least partially identifying one or more of one or more domains of a target structure, one or more shapes of the target structure, one or more charges of a target structure, one or more functions of a target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA.

At the optional operation 1103, a first data entry may be received from a graphical user interface, or at the optional operation 1104, from at least one submission element of a graphical user interface.

FIG. 9 illustrates optional embodiments of the operational flow 100 of FIG. 7. FIG. 9 shows illustrative embodiments of the optional accessing operation 210, accessing the first possible dataset in response to the first input, including operations accessing the first possible dataset and may include at least one additional operation. Accessing operations may optionally include, but are not limited to, operation 2100, operation 2101, operation 2102, operation 2103, operation 2104, operation 2105, operation 2106, operation 2107, operation 2108, operation 2109, operation 2110, operation 2111, and operation 2112.

At the optional operation 2100, a first possible dataset may be accessed in response to a first input, the first input including one or more of a target or one or more target components. At the optional operation 2101, a first possible dataset may be accessed from within a first database associated with a plurality of targets and target components. At the optional operation 2102, a first possible dataset may be accessed by associating one or more of a target and/or one or more target components with one or more elements of the first possible dataset. At the optional operation 2103, a first possible dataset may be accessed using a database management system engine that is configured to query a first database to retrieve a first possible dataset therefrom. At the optional operation 2104, a first possible dataset may be accessed by corresponding one or more of a target and one or more target components with one or more elements of a first possible dataset.

A first possible dataset may be accessed by associating one or more of a target, one or more of a target structure, a peptide sequence, a nucleic acid sequence, a biological assembler, one or more biological assembler components, one or more amino acids, one or more charged tRNA, or one or more tRNA with one or more elements of the first possible dataset. A first possible dataset may be accessed by associating one or more of one or more domains of a target structure, one or more shapes of a target structure, one or more charges of a target structure, one or more functions of a target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA with one or more elements of the first possible dataset. A first possible dataset may be accessed as being associated with one or more of a target or one or more target components, based on one or more characterizations stored in association with one or more elements of the first possible dataset and related to one or more of a peptide sequence, a nucleic acid sequence, biological assembler, one or more biological assembler components, one or more amino acids, one or more charged tRNA, or one or more tRNA.

At the optional operation 2105, a first request associated with a first possible dataset may be received. At the optional operation 2106, a first request associated with a first possible dataset may be received, the first request selecting one or more of a target or one or more target components. At the optional operation 2107, a first request from a graphical user interface may be received. At the optional operation 2108, a first request from at least one submission element of a graphical user interface may be received. At the optional operation 2109, a first request from at least one submission element of a graphical user interface may be received, one or more first requests at least partially identifying one or more elements of a first possible dataset. At the optional operation 2110, a first request from at least one submission element of a graphical user interface may be received, one or more first requests at least partially selecting one or more elements of a first possible dataset. At the optional operation 2111, a first request from at least one submission element of a graphical user interface may be received, one or more first requests providing instructions identifying one or more of a target or one or more target components.

A first request from at least one submission element of a graphical user interface may be received, one or more first requests providing instructions identifying a target structure, a peptide sequence, a nucleic acid sequence, a biological assembler, one or more biological assembler components, one or more amino acids, one or more charged tRNA, or one or more tRNA. A first request from at least one submission element of a graphical user interface may be received, one or more first requests providing instructions identifying one or more domains of a target structure, one or more shapes of the target structure, one or more charges of a target structure, one or more functions of a target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA.

At the optional operation 2112, a first possible dataset may be accessed in response to a first request, the first request specifying one or more of a target or one or more target components and at least one other instruction.

Figure 10:
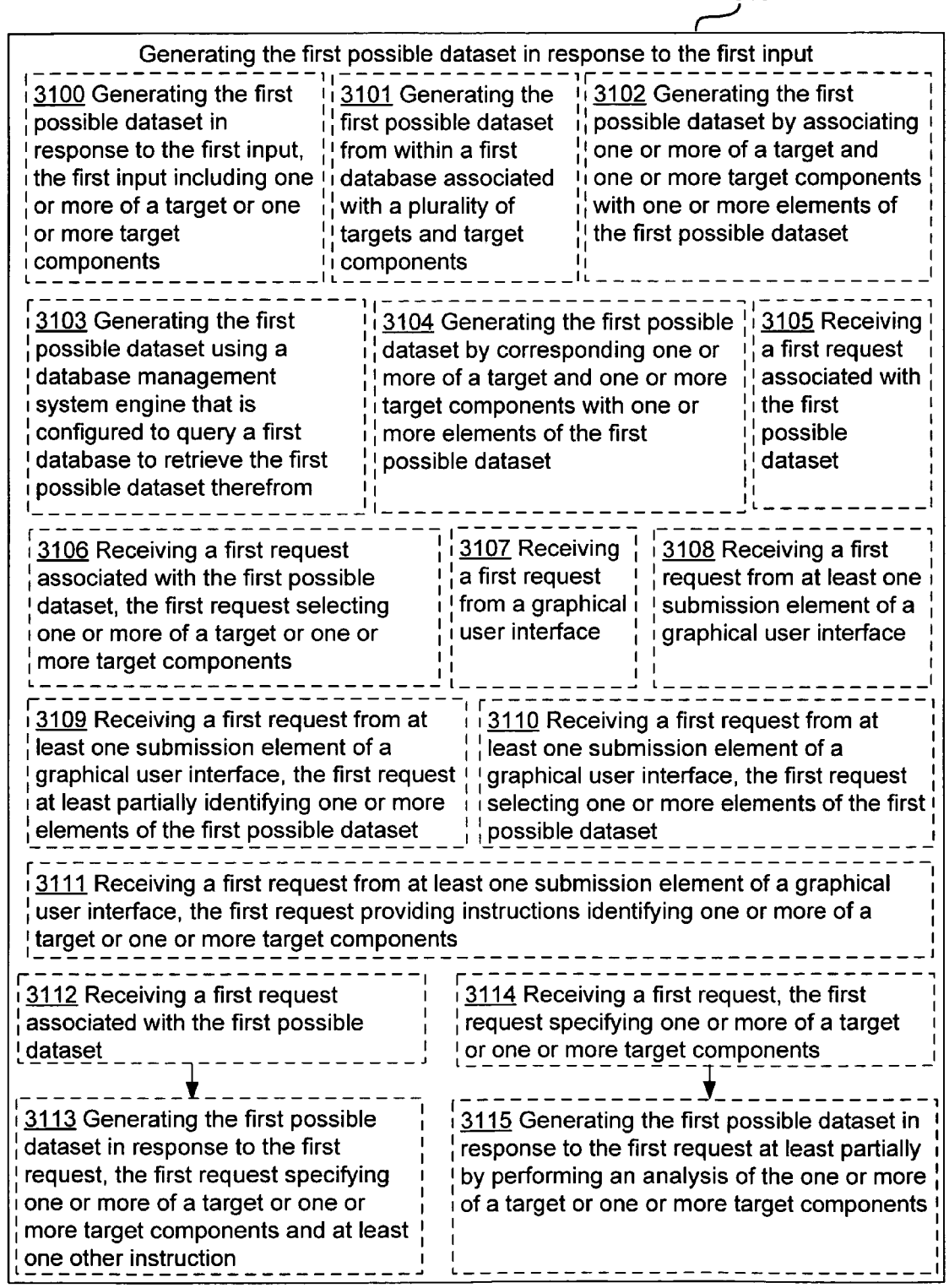
FIG. 10 shows optional embodiments of the operational flow of FIG. 7.

FIG. 10 illustrates optional embodiments of the operational flow 100 of FIG. 7. FIG. 10 shows illustrative embodiments of the optional generating operation 310, generating the first possible dataset in response to the first input, including operations generating the first possible dataset and may include at least one additional operation. Generating operations may optionally include, but are not limited to, operation 3100, operation 3101, operation 3102, operation 3103, operation 3104, operation 3105, operation 3106; operation 3107, operation 3108, operation 3109, operation 3110, operation 3111, operation 3112, operation 3113, operation 3114, operation 3115.

At the optional operation 3100, a first possible dataset may be generated in response to a first input, the first input including one or more of a target or one or more target components. At the optional operation 3101, a first possible dataset may be generated from within the first database associated with a plurality of targets and target components. At the optional operation 3102, a first possible dataset may be generated by associating one or more of a target and one or more target component with one or more elements of the first possible dataset. At the optional operation 3103, a first possible dataset may be generated using a database management system engine that is configured to query a first database to retrieve a first possible dataset therefrom. At the optional operation 3104, a first possible dataset may be generated by corresponding one or more of a target and one or more target components with one or more elements of the first possible dataset.

A first possible dataset may be generated by associating one or more of the target structure, at peptide sequence, a nucleic acid sequence, a biological assembler, one or more biological assembler components, one or more amino acids, one or more charged tRNA, or one or more tRNA, with one or more elements of the first possible dataset. A first possible dataset may be generated by associating one or more of one or more domains of the target structure, one or more shapes of the target structure, one or more charges of the target structure, one or more functions of the target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA, with one or more elements of the first possible dataset.

At the optional operation 3105, a first request associated with a first possible dataset may be received. At the optional operation 3106, a first request associated with the first possible dataset may be received, the first request selecting one or more of a target or one or more target components. At the optional operation 3107, a first request from a graphical user interface may be received. At the optional operation 3108, a first request may be received from at least one submission element of a graphical user interface. At the optional operation 3109, a first request may be received from at least one submission element of a graphical user interface, the first request at least partially identifying one or more elements of the first possible dataset. At the optional operation 3110, a first request may be received from at least one submission element of a graphical user interface, the first request selecting one or more elements of the first possible dataset. At the optional operation 3111, a first request may be received from at least one submission element of the graphical user interface, the first request providing instructions identifying one or more of a target or one or more target components.

A first request may be received from at least one submission element of the graphical user interface, the first request providing instructions identifying the target structure, a peptide sequence, a nucleic acid sequence, a biological assembler, one or more biological assembler components, one or more amino acids, one or more charged tRNA, or one or more tRNA. A first request may be received from at least one submission element of the graphical user interface, the first request providing instructions identifying one or more domains of the target structure, one or more shapes of the target structure, one or more charges of the structure, one or more functions of a target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA.

At the optional operation 3112, a first request associated with the first possible dataset may be received, and at the optional operation 3113, the first possible dataset may be generated in response to the first request, the first request specifying one or more of a target or one or more target components and at least one other instruction. At the optional operation 3114, a first request may be received, the first request specifying one or more of a target or one or more target components, and at the optional operation 3115, the first possible dataset may be generated in response to the first request at least partially by performing an analysis of the one or more of a target or one or more target components.

Figure 11:
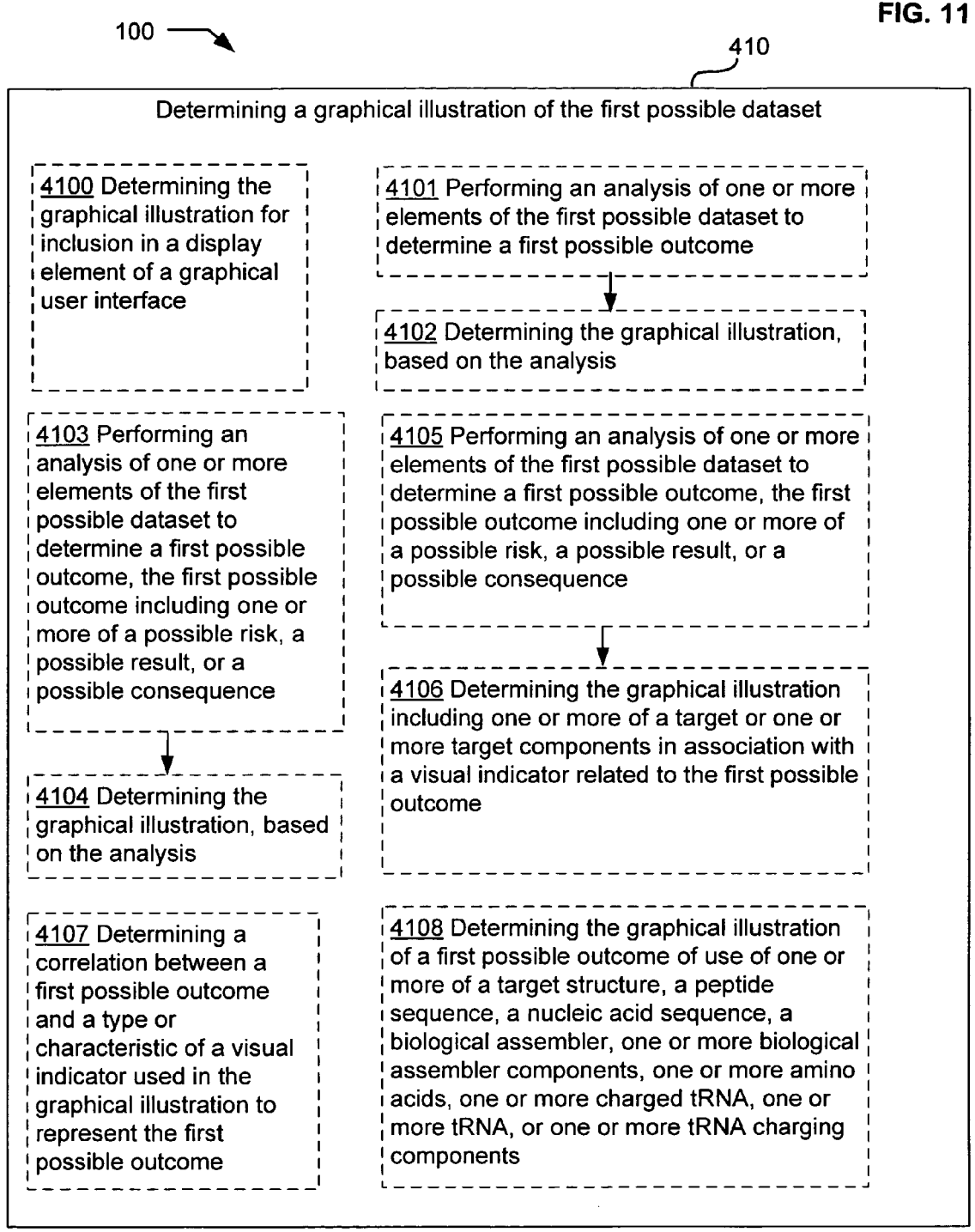
FIG. 11 shows optional embodiments of the operational flow of FIG. 7.

FIG. 11 illustrates optional embodiments of the operational flow 100 of FIG. 7. FIG. 11 shows illustrative embodiments of the optional determining operation 410, determining a graphical illustration of the first possible dataset, including operations determining a graphical illustration of the first possible dataset and may include at least one additional operation. Determining operations may optionally include, but are not limited to, operation 4100, operation 4101, operation 4102, operation 4103, operation 4104, operation 4105, operation 4106, operation 4107, and operation 4108.

At the optional operation 4100, a graphical illustration for inclusion in a display element of a graphical user interface may be determined. At the optional operation 4101, an analysis of one or more elements of the first possible dataset may be performed to determine a first possible outcome, and at the optional operation 4102 the graphical illustration may be determined based on the analysis. At the optional operation 4103, analysis of one or more elements of the first possible dataset may be performed to determine a first possible outcome, the first possible outcome including one or more of a possible risk, a possible result, or a possible consequence; and at the optional operation 4104 the graphical illustration may be determined based on the analysis. At the optional operation 4105, an analysis of one or more elements of the first possible dataset may be performed to determine the first possible outcome, the first possible outcome including one or more of a possible risk, a possible result, or a possible consequence, and at the optional operation 4106, the graphical illustration may be determined including one or more of a target or one or more target components in association with a visual indicator related to the first possible outcome. At the optional operation 4107, correlation between the first possible outcome and a type or characteristic of a visual indicator used in the graphical illustration to represent the first possible outcome may be determined. At the optional operation 4108, the graphical illustration of the first possible outcome of use of one or more of the target structure, a peptide sequence, a nucleic acid sequence, a biological assembler, one or more biological assembler components, one or more amino acids, one or more charged tRNA, one or more tRNA, or one or more tRNA charging components may be determined. The graphical illustration of a first possible outcome of use of one or more of one or more domains of the target structure, one or more shapes of the target structure, one or more charges of the structure, one or more functions of a target structure, an mRNA sequence, a RNA sequence, a cDNA sequence, a DNA sequence, one or more natural amino acids, one or more unnatural amino acids, one or more tRNA charged with natural amino acids, one or more tRNA charged with unnatural amino acids, one or more tRNA charged with arbitrary amino acids, one or more natural tRNA, one or more unnatural tRNA, one or more anti-stop codon tRNA, one or more anti-singlet codon tRNA, one or more anti-doublet codon tRNA, one or more anti-triplet codon tRNA, one or more anti-quadruplet codon tRNA, one or more anti-quintuplet codon tRNA, or one or more anti-sextuplet codon tRNA may be determined.

Figure 12:
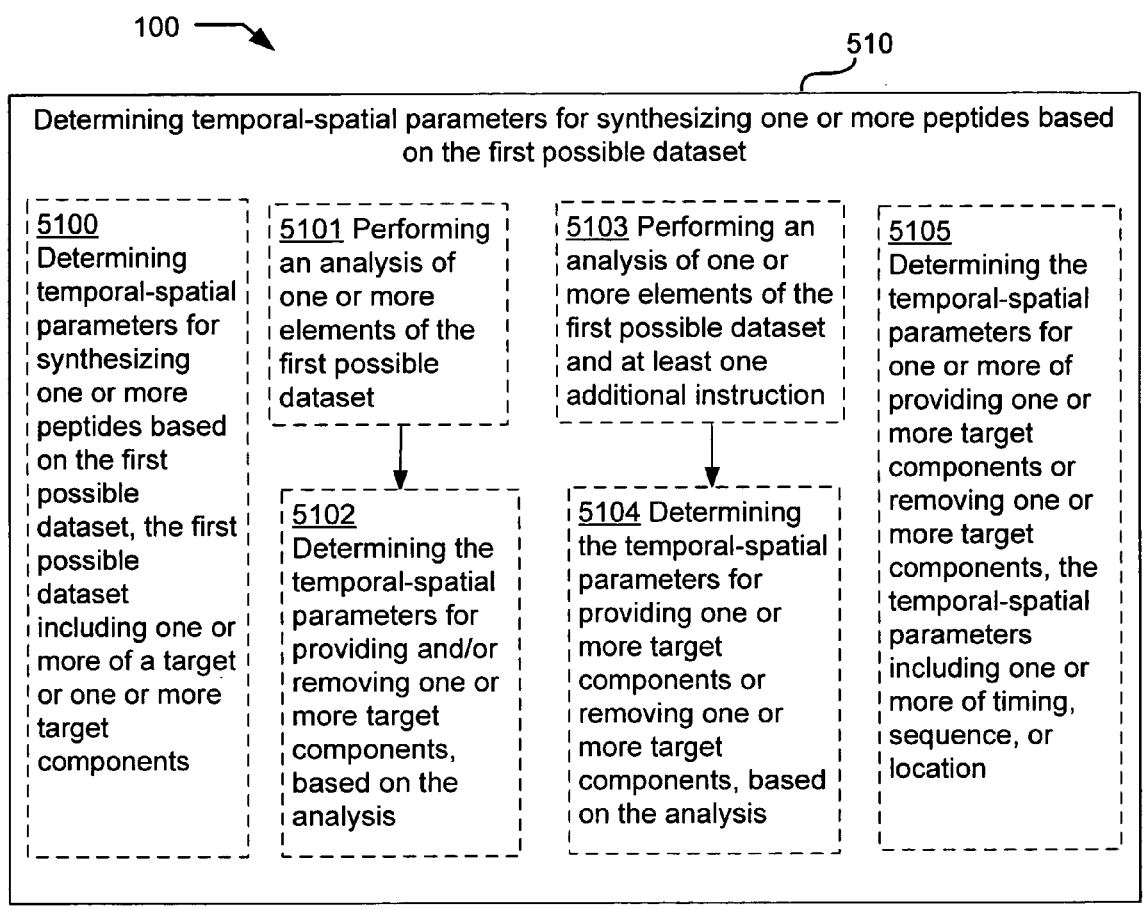
FIG. 12 shows optional embodiments of the operational flow of FIG. 7.

FIG. 12 illustrates optional embodiments of the operational flow 100 of FIG. 7. FIG. 12 shows illustrative embodiments of the determining operation 510, determining temporal-spatial parameters for synthesizing one or more target peptides based on the first possible dataset, including operations determining temporal-spatial parameters for implementing the first possible dataset and may include at least one additional operation. Determining operations may optionally include, but are not limited to, operation 5100, operation 5101, operation 5102, operation 5103, operation 5104, and operation 5105.

At the optional operation 5100, temporal-spatial parameters for synthesizing one or more peptides based on the first possible dataset may be determined, the first possible dataset including one or more of a target or one or more target components. At the optional operation 5101, an analysis of one or more elements of the first possible dataset may be performed, and at the optional operation 5102, the temporal spatial parameters for providing one or more target components may be determined, based on the analysis. At the optional operation 5103, an analysis of one or more elements of the first possible dataset and at least one additional instruction may be performed, and at the optional operation 5104, the temporal-spatial parameters for providing one or more target components and/or removing one or more target components may be determined, based on the analysis. At the optional operation 5105, the temporal-spatial parameters for providing one or more target components and/or removing one or more target components may be determined, the temporal-spatial parameters including one or more of timing, sequence, or location.

Figure 13:
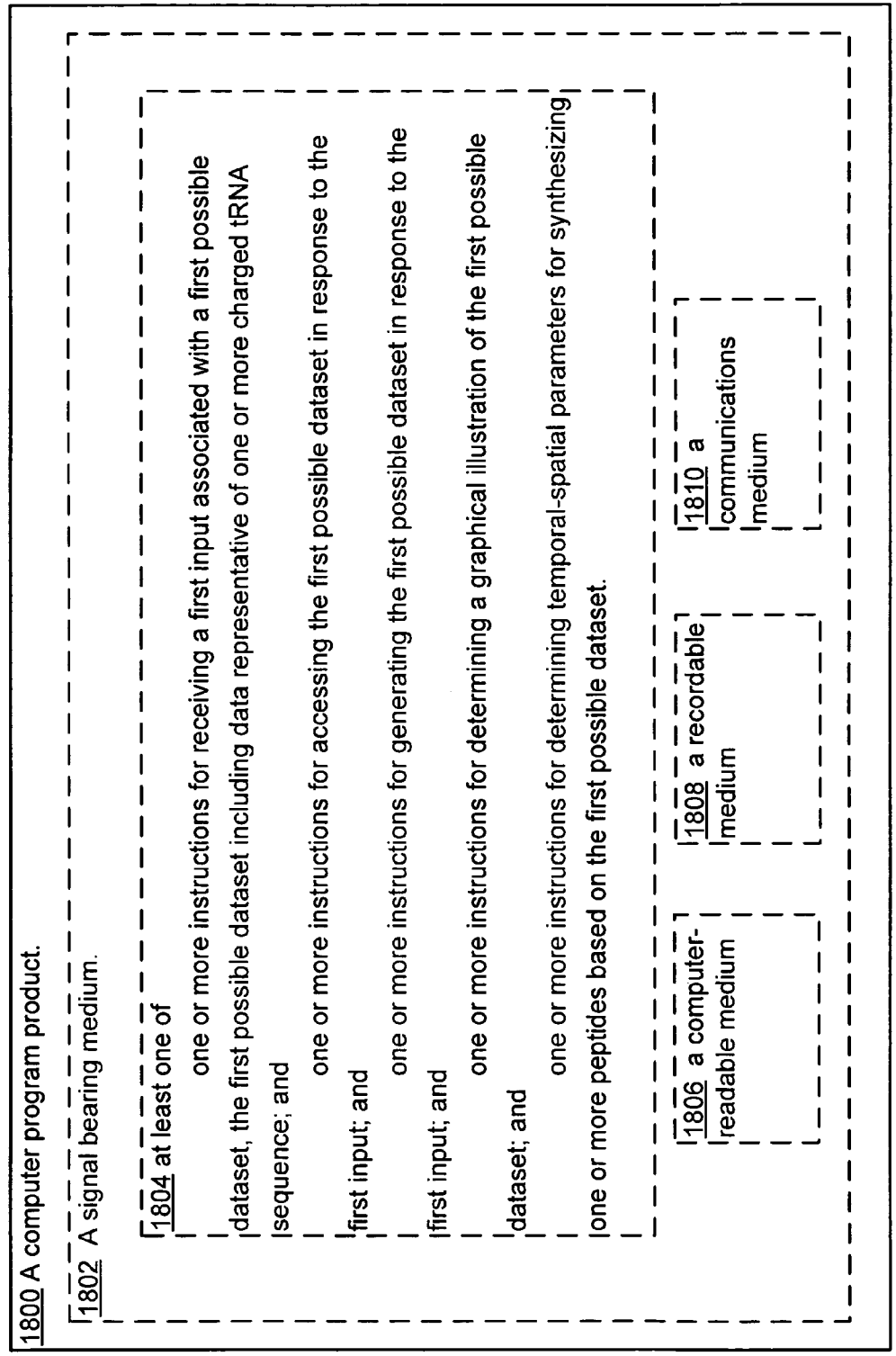
FIG. 13 shows a partial view of an illustrative embodiment of a computer program product that includes a computer program for executing a computer process on a computing device.

FIG. 13 shows a schematic of a partial view of an illustrative computer program product 1800 that includes a computer program for executing a computer process on a computing device. An illustrative embodiment of the example computer program product is provided using a signal bearing medium 1802, and may include at least one instruction of 1804: one or more instructions for receiving a first input associated with a first possible dataset, the first possible dataset including data representative of one or more charged tRNA sequence; one or more instructions for accessing the first possible dataset in response to the first input; one or more instructions for generating the first possible dataset in response to the first input; one or more instructions for determining a graphical illustration of the first possible dataset; or one or more instructions for determining temporal-spatial parameters for synthesizing one or more peptides based on the first possible dataset. The one or more instructions may be, for example, computer executable and/or logic implemented instructions. In some embodiments, the signal bearing medium 1802 of the one or more computer program 1800 products include a computer readable medium 1806, a recordable medium 1808, and/or a communications medium 1810.

Figure 14:
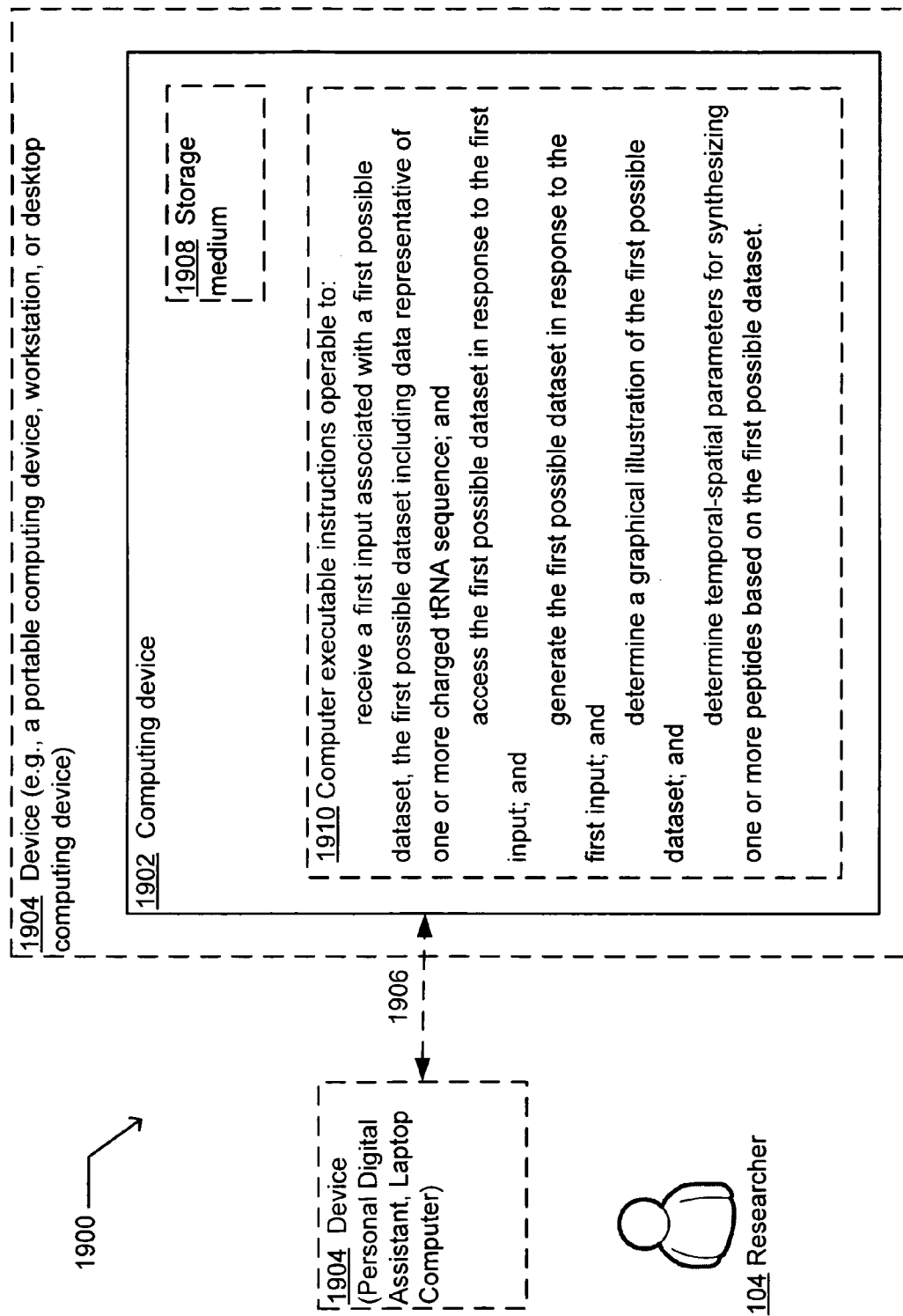
FIG. 14 shows an illustrative embodiment of a system in which embodiments may be implemented.

FIG. 14 shows a schematic of an illustrative system 1900 in which embodiments may be implemented. The system 1900 may include a computing system environment. The system 1900 also illustrates a researcher/scientist/investigator/operator 104 using a device 1904, that is optionally shown as being in communication with a computing device 1902 by way of an optional coupling 1906. The optional coupling may represent a local, wide area, or peer-to-peer network, or may represent a bus that is internal to a computing device (e.g. in illustrative embodiments the computing device 1902 is contained in whole or in part within the device 1904 or within one or more apparatus 410, or one or more computing units 426, or one or more controller units 422, or one or more monitoring units 440). An optional storage medium 1908 may be any computer storage medium.

The computing device 1902 includes one or more computer executable instructions 1910 that when executed on the computing device 1902 cause the computing device 1902 to receive the first input associated with the first possible dataset, the first possible dataset including data representative of one or more charged tRNA sequences; optionally access the first possible dataset in response to the first input; optionally generate the first possible dataset in response the first input; optionally determine a graphical illustration of the first possible dataset; and determine temporal-spatial parameters for synthesizing one or more peptides at least partially based on a first possible dataset. In some illustrative embodiments, the computing device 1902 may optionally be contained in whole or in part within an apparatus 410 and/or one or more peptide synthesizer units 420 of FIG. 1 (e.g. one or more computing units 426, and/or one or more controller units 422, and/or one or more monitoring units 440), or may optionally be contained in whole or in part within the researcher device 1904.

The system 1900 includes at least one computing device (e.g. 1904 and/or 1902 and/or one or more computing units 426 of FIG. 1) on which the computer-executable instructions 1910 may be executed. For example, one or more of the computing devices (e.g. 1902, 1904, 426) may execute the one or more computer executable instructions 1910 and output a result and/or receive information from the researcher (optionally from one or more monitoring unit 440) on the same or a different computing device (e.g. 1902, 1904, 426) and/or output a result and/or receive information from one or more peptide synthesizer units 420 and/or one or more monitoring units 440 and/or one or more computing units 426 and/or one or more controller units 422 in order to perform and/or implement one or more of the techniques, processes, or methods described herein, or other techniques.

The computing device (e.g. 1902 and/or 1904 and/or 426) may include one or more of a desktop computer, a workstation computer, a computing system comprised a cluster of processors, a networked computer, a tablet personal computer, a laptop computer, or a personal digital assistant, or any other suitable computing unit or may be part of any one of the apparatus 410 described herein. In some embodiments, an apparatus 410, one or more peptide synthesizer units 420 and/or one or more monitoring units 440 and/or one or more controller units 422 may be operable to communicate with any one of the one or more computing devices (e.g. 1902 and/or 1904 and/or 426) that may be operable to communicate with a database to access the first possible dataset and/or subsequent datasets. In some embodiments, the computing device (e.g. 1902 and/or 1904 and/or 426) is operable to communicate with the peptide biological synthesis apparatus 410.

In one aspect, the disclosure is drawn to one or more methods comprising receiving a first input associated with a first possible dataset, the first possible dataset including data representative of one or more aspects of target peptide synthesis; and determining temporal-spatial parameters for sequentially co-localizing one or more target components based on the first possible dataset and/or for separating one or more target components based on the first possible dataset. One or more of these methods may be used as part of one or more methods of target peptide synthesis and/or implemented on one or more apparatus 410 for target peptide synthesis.

Figure 15:
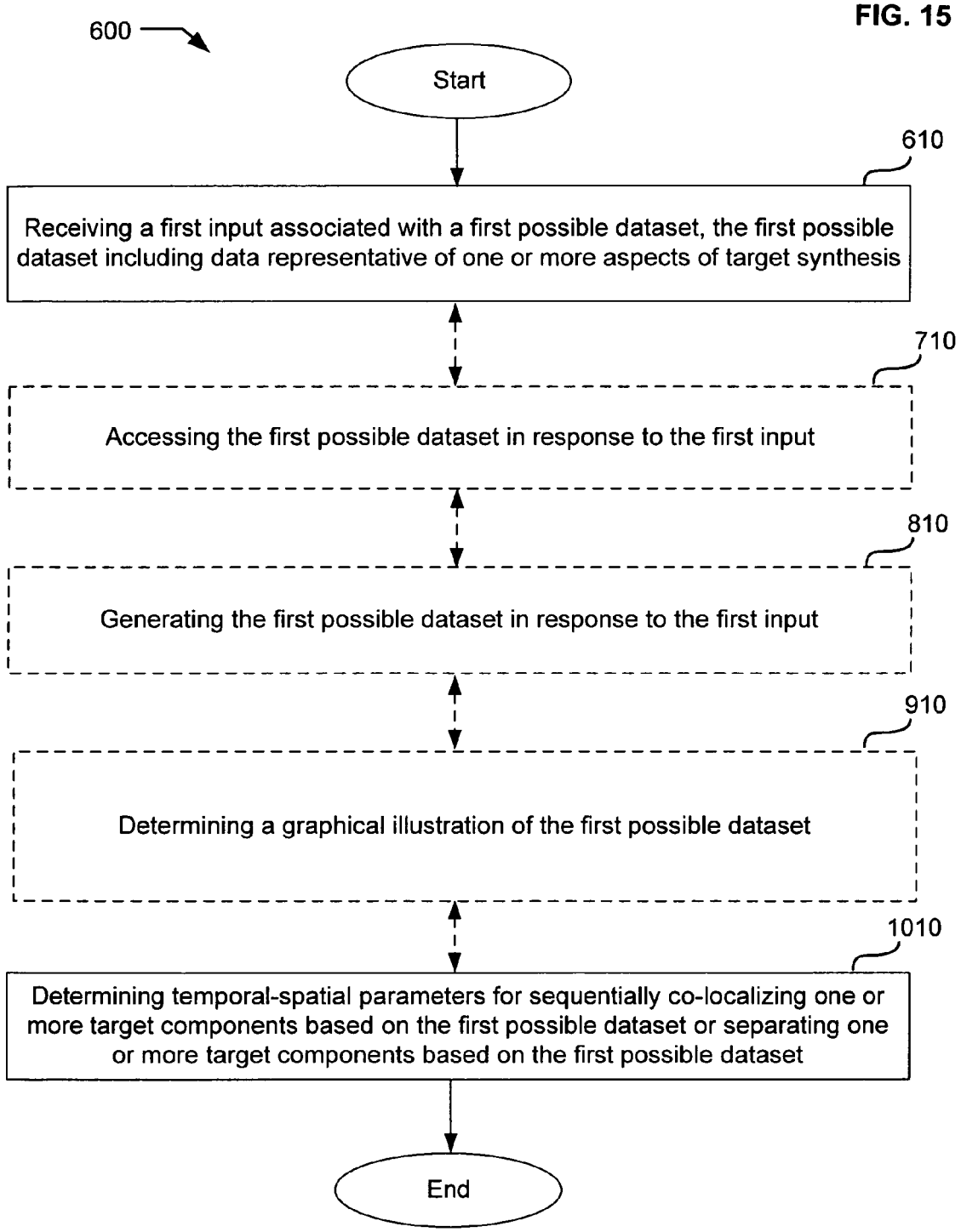
FIG. 15 shows an operational flow representing illustrative embodiments of operations related to determining temporal-spatial parameters for co-localizing and/or separating one or more target components based on a first possible dataset.

FIG. 15 shows an operational flow 600 representing illustrative embodiments of operations related to determining temporal-spatial parameters for sequentially co-localizing one or more target components based on the first possible dataset and/or for separating one or more target components based on the first possible dataset. In FIG. 15, and in the following figures that includes various illustrative embodiments of operational flows, discussion and explanation may be provided with respect to apparatus and methods described herein, and/or with respect to other examples and contexts. The operational flows may also be executed in a variety of other contexts and environments, and or in modified versions of those described herein. In addition, although some of the operational flows are presented in sequence, the various operations may be performed in various repetitions, concurrently, and/or in other orders than those that are illustrated. The operational flows may be performed in real time during target peptide synthesis.

After a start operation, the operational flow 600 moves to a receiving operation 610 where a first input may be associated with a first possible dataset, the first possible dataset including data representative of one or more aspects of target synthesis. For example, a first input may include data representative of the progress of target peptide synthesis. Data representative of the progress of target peptide synthesis may be manually or automatically gathered, or derived from monitoring the progress of target peptide synthesis. Monitoring may be optionally performed by one or more monitoring units 440.

An optional accessing operation 710 accesses the first possible dataset in response to the first input. For example, data representative of the progress of target peptide synthesis may be accessed. Such data may be manually or automatically generated, or derived from one or more monitoring units 440.

An optional generating operation 810 generates the first possible dataset in response to the first input. For example, data representative of the progress of target peptide synthesis may be generated. Such data may be manually or automatically generated, or derived from one or more monitoring units 440.

An optional determining operation 910 determines a graphical illustration of the first possible dataset. For example, data representative of the progress of target peptide synthesis may be graphically represented. Such data may be manually or automatically generated, or derived from one or more monitoring units 440.

Then, a determining operation 1010, determines temporal-spatial parameters for optionally sequentially co-localizing one or more target components based on the first possible dataset and/or for separating one or more target components based on the first possible dataset. For example, temporal-spatial parameters for sequentially co-localizing one or more target components based on the first possible dataset and/or for separating one or more target components based on the first possible dataset may be determined at least partially based on data representative of the progress of target peptide synthesis. Such data may be manually or automatically generated, or derived from one or more monitoring units 440.

Operations 610 to 1010 may be performed with respect to a digital representation (e.g. digital data) of, for example, data representative of progress of a target peptide synthesis. The logic may accept a digital or analog (for conversion into digital) representation of an input and/or provide a digitally-encoded representation of a graphical illustration, where the input may be implemented and/or accessed locally or remotely.

Operations 610 to 1010 may be performed related to either a local or a remote storage of the digital data, or to another type of transmission of the digital data. In addition to inputting, accessing querying, recalling, calculating, determining or otherwise obtaining the digital data, operations may be performed related to storing, assigning, associating, displaying or otherwise archiving the digital data to a memory, including for example, sending and/or receiving a transmission of the digital data from a remote memory. Accordingly, any such operations may involve elements including at least an operator (e.g. human or computer) directing the operation, a transmitting computer, and/or receiving computer, and should be understood to occur in the United States as long as at least one of these elements resides in the United States.

FIG. 16 illustrates optional embodiments of the operational flow 600 of FIG. 15. FIG. 16 shows illustrative embodiments of the receiving operation 610, including operations receiving a first input, optionally data entry, associated with a first possible dataset, the first input including data representative of one or more aspects of target synthesis, and optionally one or more additional operations. Receiving operations may optionally include, but are not limited to, operation 6100, operation 6101, operation 6102, operation 6103, operation 6104, operation 6105, operation 6106, operation 6107, operation 6108, operation 6109, operation 6110, and/or operation 6111.

At the optional operation 6100, the first input may include data representative of amino acid incorporation into one or more peptides, biological assembler activity, nucleic acid translocation, and/or tRNA release. At the optional operation 6101, the first input may include data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA.

At the optional operation 6110, the first input may be associated with monitoring amino acid incorporation, biological assembly activity, nucleic acid translocation, and/or tRNA release. At the optional operation 6111, the first input may be associated with monitoring availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA. Monitoring may be performed by one or more monitoring units 440.

At the optional operation 6102, a first data entry associated with the first possible dataset may be received. At the optional operation 6109, a first data entry at least partially identifying one or more elements of the first possible dataset may be received.

At the optional operation 6103, a first data entry associated with the first possible dataset may be received that may include receiving the first input associated with amino acid incorporation, biological assembly activity, nucleic acid translocation, and/or tRNA release. At the optional operation 6104, a first data entry associated with the first possible dataset may be received that may include data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA.

At the optional operation 6105, a first data entry from one or more peptide synthesizer units 420 may be received. At the optional operation 6106, a first data entry from one or more monitoring units 440, one or more computing units 426 and/or one or more controller units 422 may be received.

At the optional operation 6107, a first data entry may be received from a graphical user interface, or at the optional operation 6108 from at least one submission element of a graphical user interface.

FIG. 17 illustrates optional embodiments of the operational flow 600 of FIG. 15. FIG. 17 shows illustrative embodiments of the optional accessing operation 710, including operations accessing the first possible dataset in response to the first input, and may include at least one additional operation. Accessing operations may optionally include, but are not limited to, operation 7100, operation 7101, operation 7102, operation 7103, operation 7104, operation 7105, operation 7106, operation 7107, operation 7108, operation 7109, operation 7110, and/or operation 7111.

At the optional operation 7100, a first possible dataset may be accessed in response to a first input, the first input including data representative of amino acid incorporation into one or more peptides, biological assembler activity, nucleic acid translocation, and/or tRNA release. At the optional operation 7101, a first possible dataset may be accessed in response to a first input, the first input including data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA.

At the optional operation 7102, a first possible dataset may be accessed by associating data representative of amino acid incorporation into one or more peptides, biological assembler activity, nucleic acid translocation, and/or tRNA release with one or more elements of the first possible dataset. At the optional operation 7103, a first possible dataset may be accessed by associating data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA with one or more elements of the first possible dataset.

At the optional operation 7104, a first possible dataset may be accessed by corresponding data representative of amino acid incorporation into one or more peptides, biological assembler activity, nucleic acid translocation, and/or tRNA release with one or more elements of the first possible dataset. At the optional operation 7105, a first possible dataset may be accessed by corresponding data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA with one or more elements of the first possible dataset.

At the optional operation 7106, a first possible dataset may be accessed in response to the first input at least partially based on receiving a first request associated with the first possible dataset. At the optional operation 7107, a first possible dataset may be accessed in response to the first input at least partially based on receiving a first request associated with the first possible dataset, the first request selecting one or more target components. At the optional operation 7108, a first possible dataset may be accessed in response to the first input at least partially based on receiving a first request from a graphical user interface, or the optional operation 7109, receiving a first request from at least one submission element of a graphical user interface. At the optional operation 7110, a first possible dataset may be accessed in response to the first input at least partially based on receiving a first request from at least one submission element of a graphical user interface, the first request providing instructions identifying one or more target components. At the optional operation 7111, a first possible dataset may be accessed in response to the first input at least partially based on receiving a first request from at least one submission element of a graphical user interface, the first request specifying one or more target components and at least one other instruction.

Figure 19:
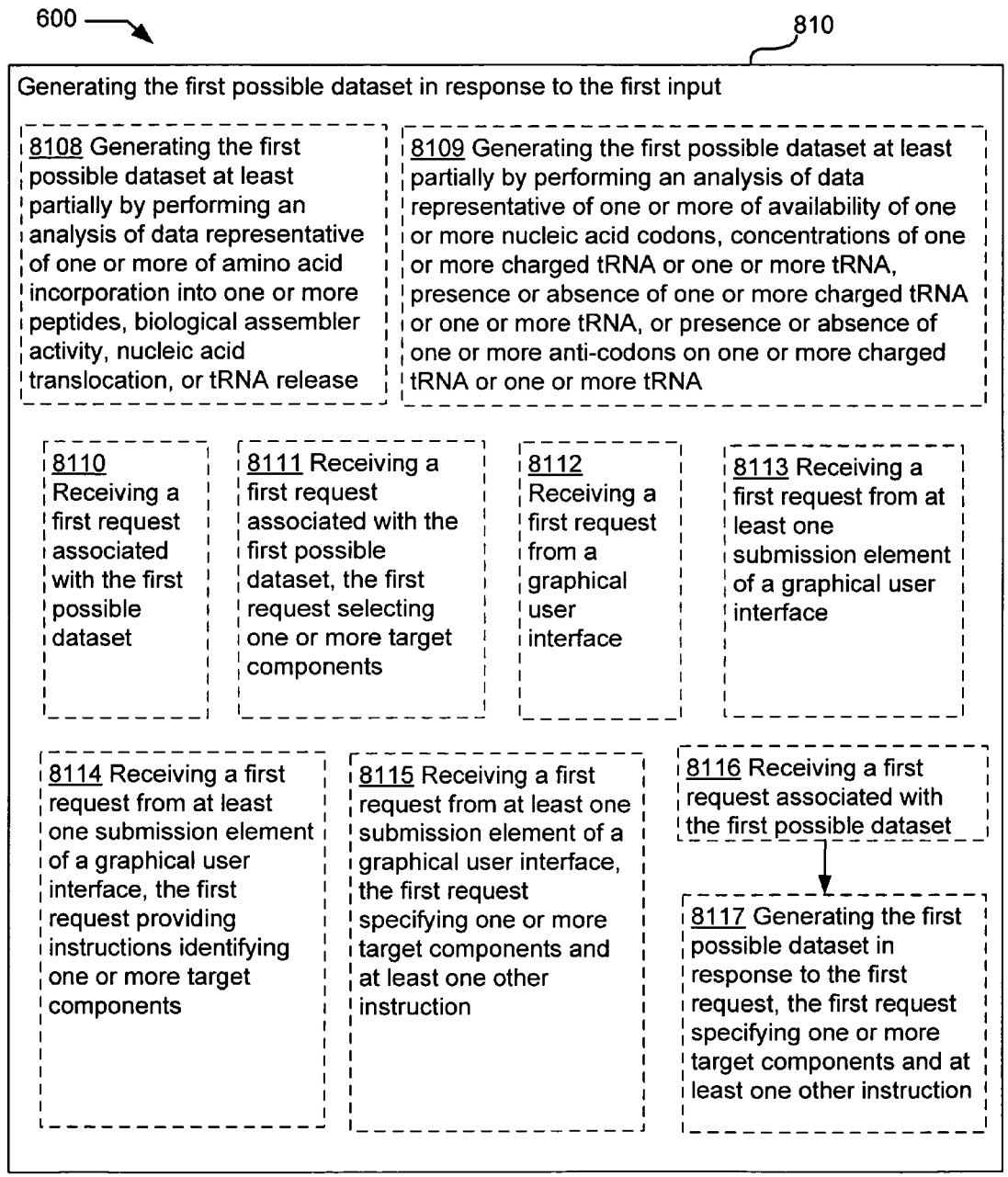
FIG. 19 shows optional embodiments of the operational flow of FIG. 15.

FIG. 18 and FIG. 19 illustrate optional embodiments of the operational flow 600 of FIG. 15. FIG. 18 and FIG. 19 show illustrative embodiments of the optional generating operation 810, including operations generating the first possible dataset in response to the first input, and may include at least one additional operation. Generating operations may optionally include, but are not limited to, operation 8100, operation 8101, operation 8102, operation 8103, operation 8104, operation 8105, operation 8108, operation 8109, operation 8110, operation 8111, operation 8112, operation 8113, operation 8114, operation 8115, operation 8116 and/or operation 8117.

At the optional operation 8100, the first possible dataset is generated in response to the first input, the first input including data representative of amino acid incorporation into one or more peptides, biological assembler activity, nucleic acid translocation, and/or tRNA release. At the optional operation 8101, the first possible dataset is generated in response to the first input, the first input including data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA.

At the optional operation 8102, the first possible dataset is generated in response to the first input by associating data representative of amino acid incorporation into one or more peptides, biological assembler activity, nucleic acid translocation, and/or tRNA release with one or more elements of the first possible dataset. At the optional operation 8103, the first possible dataset is generated in response to the first input by associating data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA with one or more elements of the first possible dataset.

At the optional operation 8104, the first possible dataset is generated in response to the first input by corresponding data representative of amino acid incorporation into one or more peptides, biological assembler activity, nucleic acid translocation, and/or tRNA release with one or more elements of the first possible dataset. At the optional operation 8105, the first possible dataset is generated by corresponding data representative of one or more of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA with one or more elements of the first possible dataset.

At the optional operation 8108, the first possible dataset is generated in response to the first input at least partially by performing an analysis of data representative of amino acid incorporation into one or more peptides, biological assembler activity, nucleic acid translocation, and/or tRNA release. At the optional operation 8109, the first possible dataset is generated in response to the first input at least partially by performing an analysis of data representative of one or more of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA.

In some embodiments, the first possible dataset is generated in response to the first input, wherein receiving a first input associated with a first possible dataset comprises receiving a first request associated with the first possible dataset 8110. In some embodiments, the first possible dataset is generated in response to the first input, wherein receiving a first input associated with a first possible dataset comprises receiving a first request associated with the first possible dataset, the first request selecting one or more target components 8111. In some embodiments, the first possible dataset is generated in response to the first input, wherein receiving a first input associated with a first possible dataset comprises receiving a first request from a graphical user interface 8112. In some embodiments, the first possible dataset is generated in response to the first input, wherein receiving a first input associated with a first possible dataset comprises receiving a first request from at least one submission element of a graphical user interface 8113. In some embodiments, the first possible dataset is generated in response to the first input, wherein receiving a first input associated with a first possible dataset comprises receiving a first request from at least one submission element of a graphical user interface, the first request providing instructions identifying one or more target components 8114. In some embodiments, the first possible dataset is generated in response to the first input, wherein receiving a first input associated with a first possible dataset comprises receiving a first request from at least one submission element of a graphical user interface, the first request specifying one or more target components and at least one other instruction 8115. In some embodiments, the first possible dataset is generated in response to the first input, wherein receiving a first input associated with a first possible dataset comprises receiving a first request associated with the first possible dataset 8116; and generating the first possible dataset in response to the first request, the first request specifying one or more target components and at least one other instruction 8117.

Figure 20:
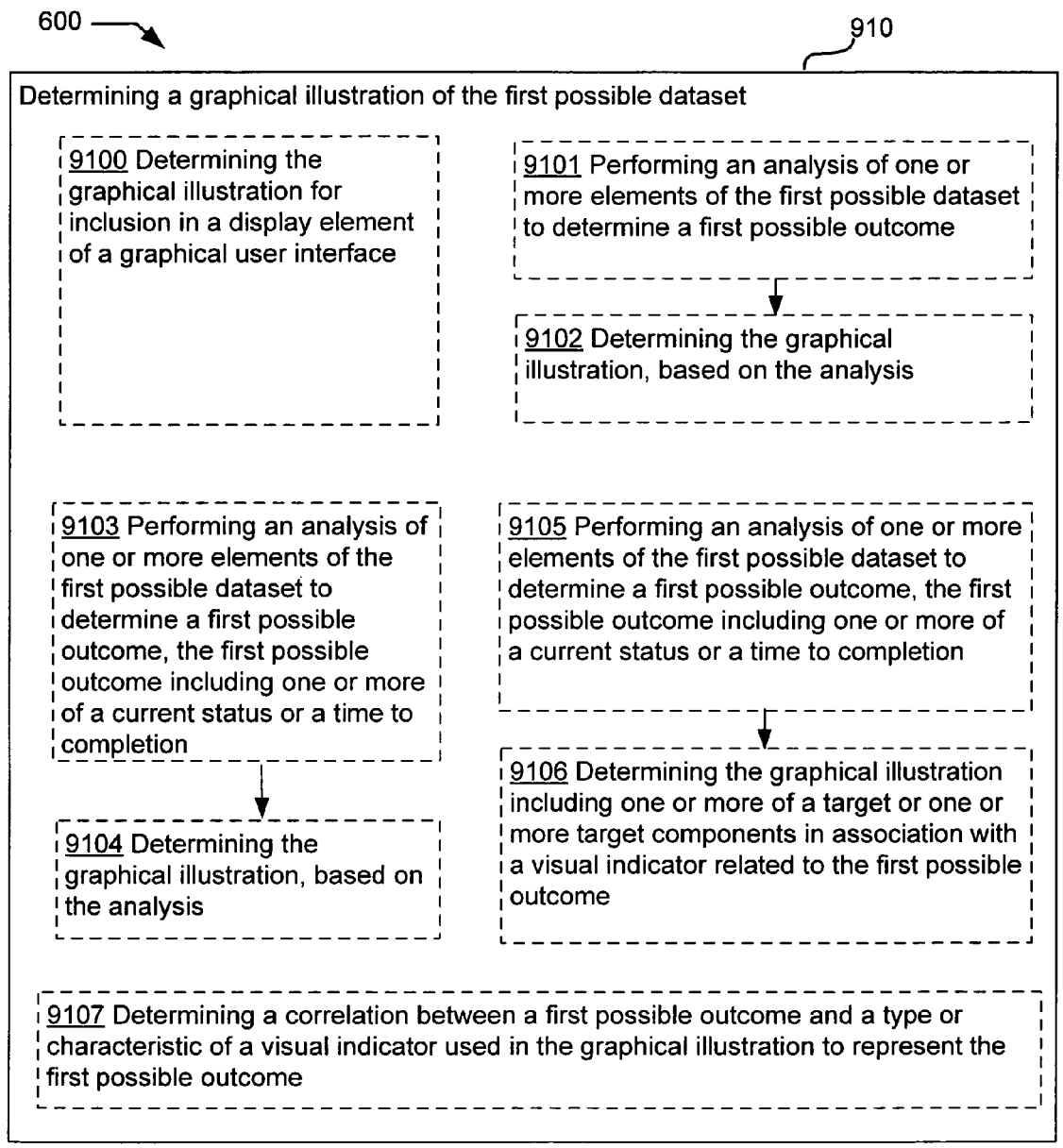
FIG. 20 shows optional embodiments of the operational flow of FIG. 15.

FIG. 20 illustrates optional embodiments of the operational flow 600 of FIG. 15. FIG. 20 shows illustrative embodiments of the optional determining operation 910, including operations determining a graphical illustration of the first possible dataset, and may include at least one additional operation. Determining operations may optionally include, but are not limited to, operation 9100, operation 9101, operation 9102, operation 9103, operation 9104, operation 9105, operation 9106, and/or operation 9107.

At the optional operation 9100, a graphical illustration of the first possible dataset is determined for inclusion in a display element of a graphical user interface. At the optional operation 9107, a graphical illustration of the first possible dataset is determined by determining a correlation between a first possible outcome and a type or characteristic of a visual indicator used in the graphical illustration to represent the first possible outcome.

In some embodiments, a graphical illustration of the first possible dataset is determined by performing an analysis of one or more elements of the first possible dataset to determine a first possible outcome 9101; and determining the graphical illustration, based on the analysis 9102. In some embodiments, a graphical illustration of the first possible dataset is determined by performing an analysis of one or more elements of the first possible dataset to determine a first possible outcome, the first possible outcome including one or more of a current status or a time to completion 9103; and determining the graphical illustration, based on the analysis 9104. In some embodiments, a graphical illustration of the first possible dataset is determined by performing an analysis of one or more elements of the first possible dataset to determine a first possible outcome, the first possible outcome including one or more of a current status or a time to completion 9105; and determining the graphical illustration including one or more of a target or one or more target components in association with a visual indicator related to the first possible outcome 9106.

Figure 21:
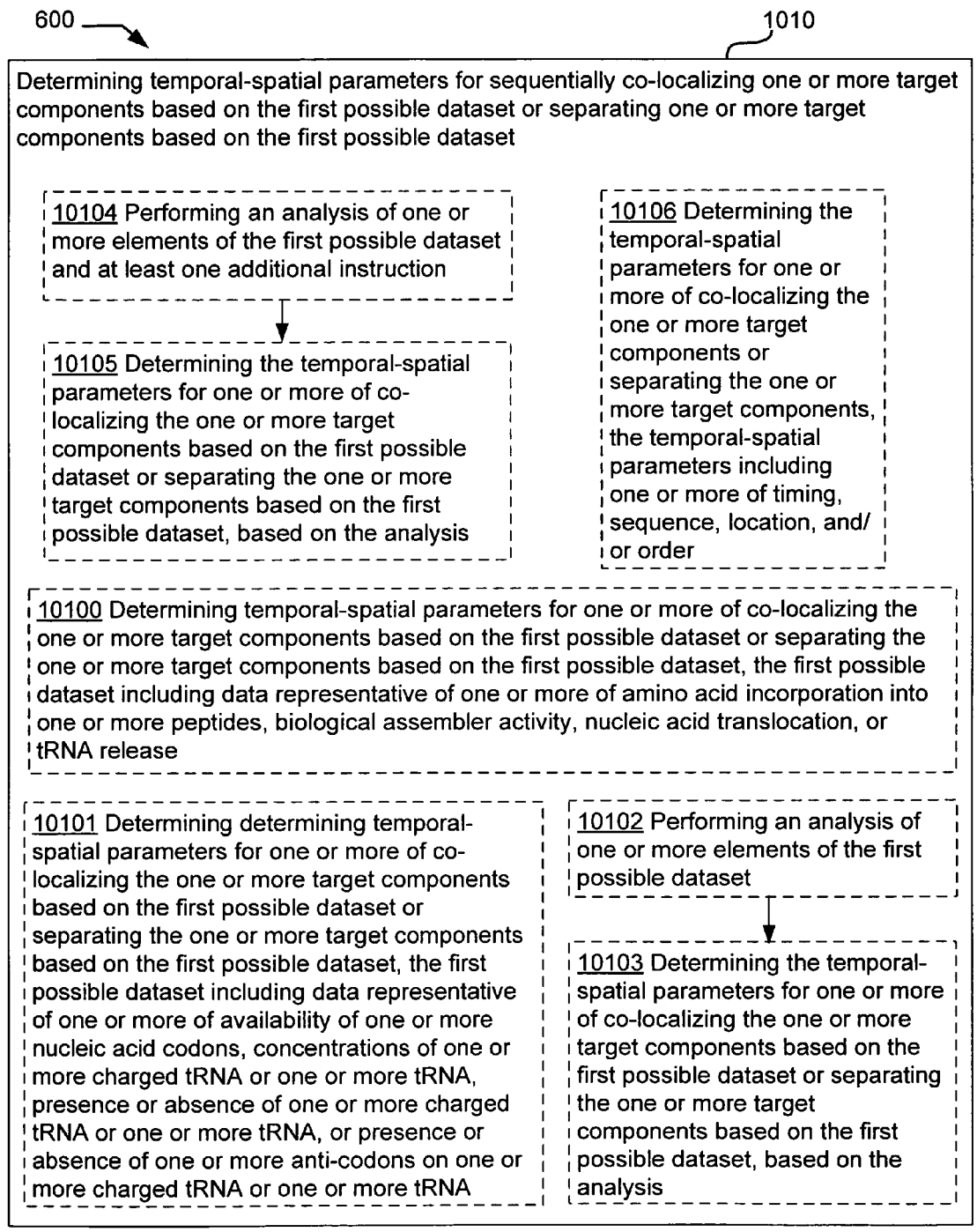
FIG. 21 shows optional embodiments of the operational flow of FIG. 15.

FIG. 21 illustrates optional embodiments of the operational flow 600 of FIG. 15. FIG. 21 shows illustrative embodiments of the determining operation 1010, including operations determining temporal-spatial parameters for optionally sequentially co-localizing one or more target components based on the first possible dataset or optionally sequentially separating one or more target components based on the first possible dataset, and may include at least one additional operation. Determining operations may optionally include, but are not limited to, operation 10100, operation 10101, operation 10102, operation 10103, operation 10104, operation 10105, and/or operation 10106.

At the optional operation 10100, temporal-spatial parameters are determined for optionally sequentially co-localizing the one or more target components based on the first possible dataset, and/or optionally sequentially separating the one or more target components based on the first possible dataset, the first possible dataset including data representative of one or more of amino acid incorporation into one or more peptides, biological assembler activity, nucleic acid translocation, or tRNA release. At the optional operation 10101, temporal-spatial parameters are determined for optionally sequentially co-localizing the one or more target components based on the first possible dataset, and/or optionally sequentially separating the one or more target components based on the first possible dataset, the first possible dataset including data representative of availability of one or more nucleic acid codons, concentrations of one or more charged tRNA and/or one or more tRNA, presence or absence of one or more charged tRNA and/or one or more tRNA, and/or presence or absence of one or more anti-codons on one or more charged tRNA and/or one or more tRNA. At the optional operation 10106, temporal-spatial parameters are determined for optionally sequentially co-localizing the one or more target components based on the first possible dataset, and/or optionally sequentially separating the one or more target components based on the first possible dataset, the temporal-spatial parameters including timing, sequence, location, and/or order.

In some embodiments, temporal-spatial parameters are determined for optionally sequentially co-localizing one or more target components based on the first possible dataset, and/or optionally sequentially separating one or more target components based on the first possible dataset by performing an analysis of one or more elements of the first possible dataset 10102; and determining the temporal-spatial parameters for optionally sequentially co-localizing the one or more target components based on the first possible dataset, and/or optionally sequentially separating the one or more target components based on the first possible dataset, based on the analysis 10103. In some embodiments, temporal-spatial parameters are determined for optionally sequentially co-localizing one or more target components based on the first possible dataset, and/or optionally sequentially separating one or more target components based on the first possible dataset by performing an analysis of one or more elements of the first possible dataset and at least one additional instruction 10104; and determining the temporal-spatial parameters for optionally sequentially co-localizing the one or more target components based on the first possible dataset, and/or optionally sequentially separating the one or more target components based on the first possible dataset, based on the analysis 10105.

Figure 22:
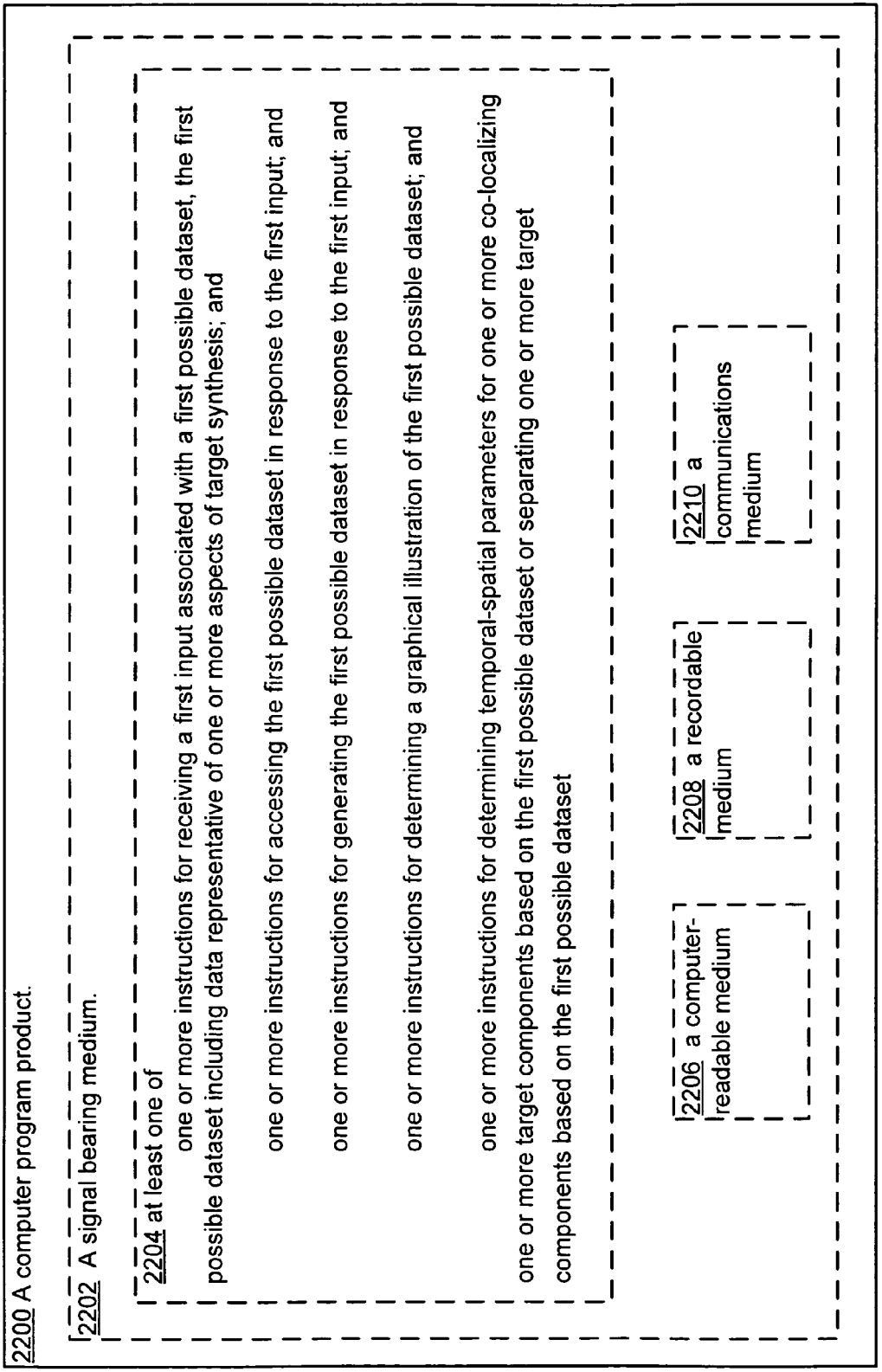
FIG. 22 shows a partial view of an illustrative embodiment of a computer program product that includes a computer program for executing a computer process on a computing device.

FIG. 22 shows a schematic of a partial view of an illustrative computer program product 2200 that includes a computer program for executing a computer process on a computing device. An illustrative embodiment of the example computer program product is provided using a signal bearing medium 2202, and may include at least one instruction of 2204: one or more instructions for receiving a first input associated with a first possible dataset, the first possible dataset including data representative of one or more aspects of target peptide synthesis; one or more instructions for accessing the first possible dataset in response to the first input; one or more instructions for generating the first possible dataset in response to the first input; one or more instructions for determining a graphical illustration of the first possible dataset; and/or one or more instructions for determining temporal-spatial parameters for one or more of sequentially co-localizing one or more target components based on the first possible dataset or optionally sequentially separating one or more target components based on the first possible dataset. The one or more instructions may be, for example, computer executable and/or logic implemented instructions. In some embodiments, the signal bearing medium 2202 of the one or more computer program products 2200 include a computer readable medium 2206, a recordable medium 2208, and/or a communications medium 2210.

Figure 23:
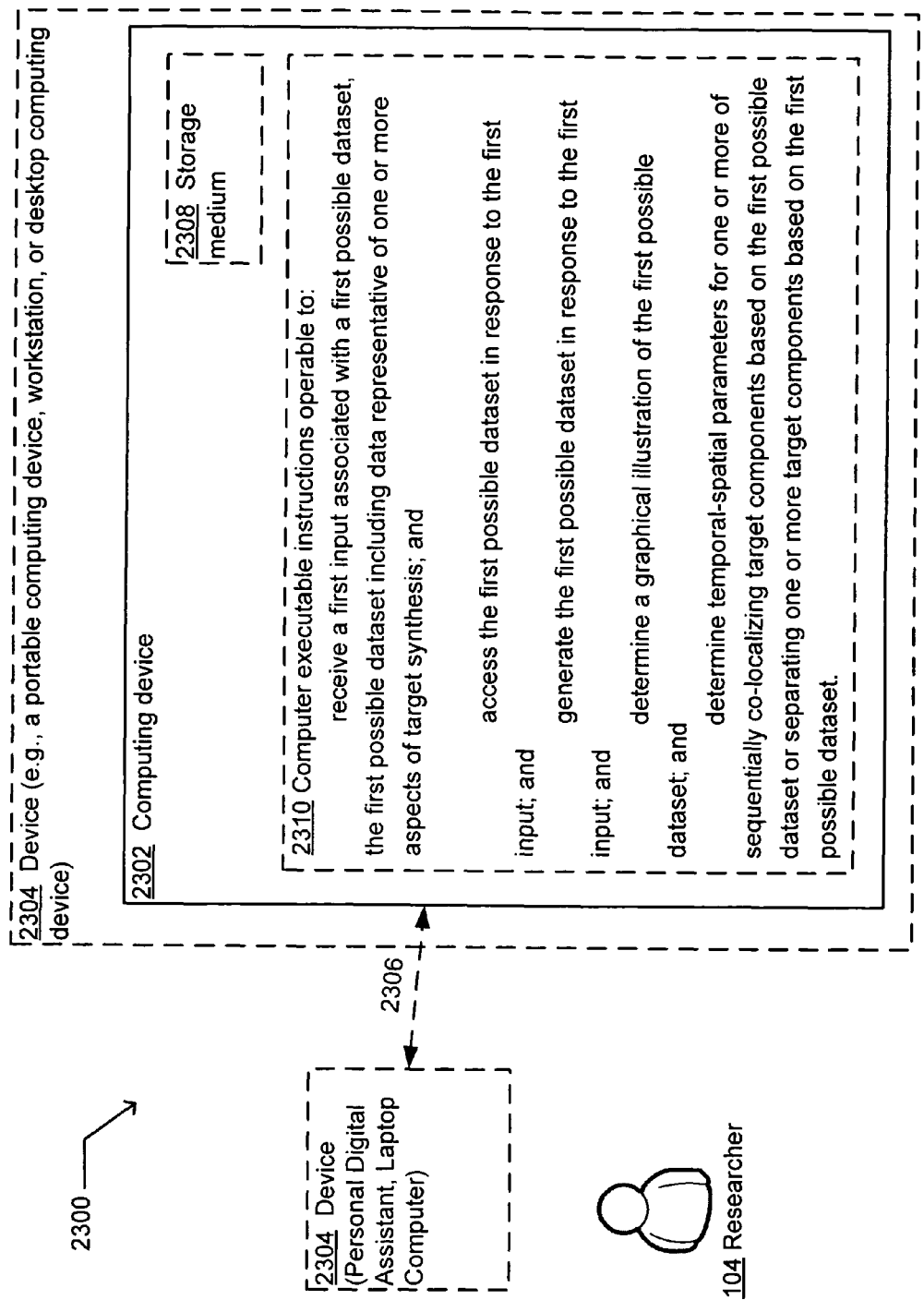
FIG. 23 shows an illustrative embodiment of a system in which embodiments may be implemented.

FIG. 23 shows a schematic of an illustrative system 2300 in which embodiments may be implemented. The system 2300 may include a computing system environment. The system 2300 also illustrates a researcher/scientist/investigator/operator 104 using a device 2304, that is optionally shown as being in communication with a computing device 2302 by way of an optional coupling 2306. The optional coupling may represent a local, wide area, or peer-to-peer network, or may represent a bus that is internal to a computing device (e.g. in illustrative embodiments the computing device 2302 is contained in whole or in part within the device 2304 or within one or more apparatus 410, or one or more computing units 426, or one or more controller units 422, or one or more monitoring units 440). An optional storage medium 2308 may be any computer storage medium.

The computing device 2302 includes one or more computer executable instructions 2310 that when executed on the computing device 2302 cause the computing device 2302 to receive a first input associated with a first possible dataset, the first possible dataset including data representative of one or more aspects of target peptide synthesis; optionally access the first possible dataset in response to the first input; optionally generate the first possible dataset in response to the first input; optionally determine a graphical illustration of the first possible dataset; and determine temporal-spatial parameters for one or more of optionally sequentially co-localizing one or more target components based on the first possible dataset or optionally sequentially separating one or more target components based on the first possible dataset. In some illustrative embodiments, the computing device 2302 may optionally be contained in whole or in part within one or more units of an apparatus 410 of FIG. 1 (e.g. one or more computing units 426 and/or one or more controller units 422 and/or one or more monitoring units 440), or may optionally be contained in whole or in part within the researcher device 2304.

The system 2300 includes at least one computing device (e.g. 2304 and/or 2302 and/or one or more computing units 426 of FIG. 1) on which the computer-executable instructions 2310 may be executed. For example, one or more of the computing devices (e.g. 2302, 2304, 426) may execute the one or more computer executable instructions 2310 and output a result and/or receive information from the researcher (optionally from one or more monitoring unit 440) on the same or a different computing device (e.g. 2302, 2304, 426) and/or output a result and/or receive information from an apparatus 410, one or more peptide synthesizer units 420, one or more controller units 422, and/or one or more monitoring units 440 in order to perform and/or implement one or more of the techniques, processes, or methods described herein, or other techniques.

The computing device (e.g. 2302 and/or 2304 and/or 426) may include one or more of a desktop computer, a workstation computer, a computing system comprised a cluster of processors, a networked computer, a tablet personal computer, a laptop computer, or a personal digital assistant, or any other suitable computing unit. In some embodiments, one or more peptide synthesis units 420 and/or one or more monitoring units 440 may be operable to communicate with any one of the computing devices (e.g. 2302 and/or 2304 and/or 426) that may be operable to communicate with a database to access the first possible dataset and/or subsequent datasets. In some embodiments, the computing device (e.g. 2302 and/or 2304 and/or 426) is operable to communicate with the peptide biological synthesizer apparatus 410.

There is little distinction left between hardware and software implementations of aspects of systems; the use of hardware or software is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references, including but not limited to patents, patent applications, and non-patent literature are hereby incorporated by reference herein in their entirety.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method comprising:
   determining, with one or more computing units, an order that two or more types of charged tRNAs are to be sequentially provided on or in a fluidic device; and
   controlling the operation of the fluidic device with the one or more computing units to assemble a target peptide by co-localizing individually sequentially according to the determined order one or more ribosome-based assemblers, and the two or more types charged tRNA on or in the fluidic device.

2. The method of claim 1, wherein two or more of the two or more types of charged tRNA have the same anti-codon and are charged with different amino acids.

3. The method of claim 1, wherein two or more of the two or more types of charged tRNA have one or more of different anti-codons or different tRNA and are charged with the same amino acid.

4. The method of claim 1, wherein controlling the operation of the fluidic device with the one or more computing units to assemble a target peptide by co-localizing individually sequentially according to the determined order one or more ribosome-based assemblers, and the two or more types charged tRNA on or in the fluidic device comprises:
   assembling the target peptide by co-localizing sequentially the one or more ribosome-based assemblers and the two or more types of charged tRNA at one or more first identifiable time intervals, wherein the one or more first identifiable time intervals are at least partially based on one or more of a predicted rate of incorporation of two or more amino acids into one or more peptides, a predicted rate of activity of the one or more ribosome-based assemblers, a predicted rate of translocation of one or more nucleic acids, or a predicted rate of release of tRNA.

5. The method of claim 1, further comprising:
monitoring one or more of amino acid incorporation into one or more peptides, ribosome-based assembler activity, nucleic acid translocation, or tRNA release.

6. The method of claim 5, wherein controlling the operation of the fluidic device with the one or more computing units to assemble a target peptide by co-localizing individually sequentially according to the determined order one or more ribosome-based assemblers, and the two or more types charged tRNA on or in the fluidic device comprises:
assembling the target peptide by co-localizing sequentially the one or more ribosome-based assemblers and the two or more types of charged tRNA at one or more first identifiable time intervals, and
wherein the one or more first identifiable time intervals are at least partially based on one or more of the amino acid incorporation into the one or more peptides, the ribosome-based assembler activity, the nucleic acid translocation, or the tRNA release.

7. The method of claim 5, wherein controlling the operation of the fluidic device with the one or more computing units to assemble a target peptide by co-localizing individually sequentially according to the determined order one or more ribosome-based assemblers, and the two or more types charged tRNA on or in the fluidic device comprises:
assembling the target peptide by co-localizing sequentially the one or more ribosome-based assemblers and the two or more types of charged tRNA at one or more first identifiable time intervals, and
wherein the one or more first identifiable time intervals are at least partially based on availability of one or more nucleic acid codons.

8. The method of claim 1, further comprising:
monitoring one or more of presence or absence, concentration, or composition of one or more of the two or more types of charged tRNA or one or more tRNA.

9. The method of claim 8, wherein controlling the operation of the fluidic device with the one or more computing units to assemble a target peptide by co-localizing individually sequentially according to the determined order one or more ribosome-based assemblers, and the two or more types charged tRNA on or in the fluidic device comprises:
assembling the target peptide by co-localizing sequentially the one or more ribosome-based assemblers and the two or more types of charged tRNA at one or more first identifiable time intervals, and
wherein the one or more first identifiable time intervals are at least partially based on the concentrations of one or more of the two or more types of charged tRNA or the one or more tRNA.

10. The method of claim 8, wherein controlling the operation of the fluidic device with the one or more computing units to assemble a target peptide by co-localizing individually sequentially according to the determined order one or more ribosome-based assemblers, and the two or more types charged tRNA on or in the fluidic device comprises:
assembling the target peptide by co-localizing sequentially the one or more ribosome-based assemblers and the two or more types of charged tRNA at one or more first identifiable time intervals, and
wherein the one or more first identifiable time intervals are at least partially based on one or more of presence or absence of one or more of the two or more types of charged tRNA or the one or more tRNA.

11. The method of claim 8, wherein controlling the operation of the fluidic device with the one or more computing units to assemble a target peptide by co-localizing individually sequentially according to the determined order one or more ribosome-based assemblers, and the two or more types charged tRNA on or in the fluidic device comprises:
assembling the target peptide by co-localizing sequentially the one or more ribosome-based assemblers and the two or more types of charged tRNA at one or more first identifiable time intervals, and
wherein the one or more first identifiable time intervals are at least partially based on one or more of presence or absence of one or more anti-codons on one or more of the two or more types of charged tRNA or the one or more tRNA.

12. The method of claim 1, wherein controlling the operation of the fluidic device with the one or more computing units to assemble a target peptide by co-localizing individually sequentially according to the determined order one or more ribosome-based assemblers, and the two or more types charged tRNA on or in the fluidic device comprises:
co-localizing the one or more ribosome-based assemblers and one or more first charged tRNA;
co-localizing the one or more ribosome-based assemblers and one or more second charged tRNA; and
optionally repeating.

13. The method of claim 12, further comprising:
co-localizing the one or more ribosome-based assemblers and one or more third charged tRNA.

14. The method of claim 1, wherein controlling the operation of the fluidic device with the one or more computing units to assemble a target peptide by co-localizing individually sequentially according to the determined order one or more ribosome-based assemblers, and the two or more types charged tRNA on or in the fluidic device comprises:
co-localizing the one or more ribosome-based assemblers and one or more first charged tRNA, the one or more first charged tRNA charged with one or more first arbitrary amino acids;
separating the one or more ribosome-based assemblers from one or more of the one or more first charged tRNA or one or more first tRNA, the one or more first tRNA released during peptide synthesis;
co-localizing the one or more ribosome-based assemblers and one or more second charged tRNA, the one or more second charged tRNA charged with one or more second arbitrary amino acids;
separating the one or more ribosome-based assemblers from one or more of the one or more second charged tRNA or one or more second tRNA, the one or more second tRNA released during peptide synthesis and
optionally repeating.

15. The method of claim 1, further comprising:
consuming sequentially the two or more types of charged tRNA.

16. The method of claim 1, further comprising:
eliminating sequentially one or more of the two or more types of charged tRNA or one or more tRNA.

17. The method of claim 1, further comprising:
separating sequentially one or more of the two or more types of charged tRNA or one or more tRNA from the one or more ribosome-based assemblers.

18. The method of claim 17, wherein separating sequentially one or more of the two or more types of charged tRNA or one or more tRNA from the one or more ribosome-based assemblers comprises:
separating sequentially one or more of the two or more types of charged tRNA or the one or more tRNA from the one or more ribosome-based assemblers at one or more second identifiable time intervals.

19. The method of claim 1, wherein determining, with one or more computing units, an order that two or more types of charged tRNAs are to be sequentially provided on or in a fluidic device comprises:
   determining the order based at least partially on a target peptide sequence.

20. The method of claim 1, wherein determining, with one or more computing units, an order that two or more types of charged tRNAs are to be sequentially provided on or in a fluidic device comprises:
   determining the order based at least partially on a nucleic acid protein coding sequence.

21. The method of claim 20, wherein a protein coding region of the nucleic acid sequence includes two or more stop codons.

22. The method of claim 21, wherein the protein coding region includes at least three stop codons.

23. The method of claim 21, wherein the protein coding region includes two or more alternating stop codons.

24. The method of claim 21, wherein the protein coding region includes one or more of one or more singlet codons, one or more doublet codons, one or more triplet codons, one or more quadruplet codons or one or more quintuplet codons.

25. The method of claim 1, wherein the two or more types of charged tRNA are charged with one or more natural amino acids, one or more unnatural amino acids, or one or more arbitrary amino acids.

26. The method of claim 25, further comprising:
   charging two or more tRNA with the one or more natural amino acids, the one or more arbitrary amino acids, or the one or more unnatural amino acids.

27. The method of claim 1, wherein the two or more types of charged tRNA are one or more charged anti-stop codon tRNA.

28. The method of claim 1, further comprising:
   selecting the two or more types of charged tRNA based at least partially on one or more of a target peptide sequence or a nucleic acid sequence.

29. The method of claim 1, wherein controlling the operation of the fluidic device with the one or more computing units to assemble a target peptide by co-localizing individually sequentially according to the determined order one or more ribosome-based assemblers, and the two or more types charged tRNA on or in the fluidic device comprises:
   co-localizing sequentially one or more peptide assemblers and the two or more types of charged tRNA.

30. The method of claim 1, wherein controlling the operation of the fluidic device with the one or more computing units to assemble a target peptide by co-localizing individually sequentially according to the determined order one or more ribosome-based assemblers, and the two or more types charged tRNA on or in the fluidic device comprises:
   co-localizing sequentially one or more prokaryotic ribosome-based assemblers, one or more eukaryotic ribosome-based assemblers, or one or more mitochondrial ribosome-based assemblers and the two or more types of charged tRNA.

31. The method of claim 1, further comprising:
   selecting the one or more ribosome-based assemblers.

32. The method of claim 1, further comprising:
   assembling one or more components of the one or more ribosome-based assemblers.

33. The method of claim 32, wherein assembling one or more components of the one or more ribosome-based assemblers comprises:
   assembling the one or more components of the one or more ribosome-based assemblers at one or more third identifiable time intervals.

34. The method of claim 32, further comprising:
   selecting the one or more components of the one or more ribosome-based assemblers.

35. The method of claim 1, further comprising:
   synchronizing the co-localizing sequentially the one or more ribosome-based assemblers and the two or more types of charged tRNA, with a protein coding sequence of one or more nucleic acids co-localized with the one or more ribosome-based assemblers.

36. The method of claim 1, further comprising:
   co-localizing one or more nucleic acids with the one or more ribosome-based assemblers.

37. The method of claim 36, wherein co-localizing one or more nucleic acids with the one or more ribosome-based assemblers comprises:
   co-localizing the one or more nucleic acids with the one or more ribosome-based assemblers at one or more fourth identifiable time intervals.

38. The method of claim 36, wherein assembling the target peptide by co-localizing sequentially the one or more ribosome-based assemblers and the two or more types of charged tRNA occurs at least partially following co-localizing the one or more nucleic acids with the one or more ribosome-based assemblers.

39. The method of claim 36, further comprising:
   selecting the one or more nucleic acids.

40. A method of extra-cellular peptide synthesis comprising:
   determining, with one or more computing units, an order that two or more types of charged tRNAs are to be sequentially provided on or in a fluidic device; and
   controlling the operation of the fluidic device with the one or more computing units to assemble a target peptide by co-localizing individually sequentially according to the determined order one or more ribosome-based assemblers, and the two or more types charged tRNA on or in the fluidic device.

41. A method comprising:
   determining an assembly order with one or more computing units that is at least partially based on a target peptide; and
   controlling the operation of a fluidic device with the one or more computing units to assemble the target peptide by co-localizing individually sequentially according to the determined assembly order one or more ribosome-based assemblers, and two or more types of charged tRNA on or in the fluidic device.

42. The method of claim 1, wherein the fluidic device includes a microfluidic device or a nanofluidic device.

43. The method of claim 1, wherein the fluidic device includes a MEMS device.

44. The method of claim 1, further comprising:
   receiving data representative of at least one of the target peptide to be assembled or charged tRNA sequences; and
   wherein controlling the operation of the fluidic device with the one or more computing units to assemble a target peptide by co-localizing individually sequentially according to the determined order one or more ribosome-based assemblers, and the two or more types charged tRNA on or in the fluidic device is at least partially based on the data.

45. The method of claim 40, wherein the fluidic device includes a microfluidic device or a nanofluidic device.

46. The method of claim 40, wherein the fluidic device includes a MEMS device.

47. The method of claim 40, further comprising:
receiving data representative of at least one of the target peptide to be assembled or charged tRNA sequences; and
wherein controlling the operation of the fluidic device with the one or more computing units to assemble a target peptide by co-localizing individually sequentially according to the determined order one or more ribosome-based assemblers, and the two or more types charged tRNA on or in the fluidic device is at least partially based on the data.

48. The method of claim 41, wherein the fluidic device includes a microfluidic device or a nanofluidic device.

49. The method of claim 41, wherein the fluidic device includes a MEMS device.

50. A method comprising:
determining, with one or more computing units, a timing that two or more types of charged tRNAs are to be sequentially provided on or in a fluidic device; and
controlling the operation of the fluidic device with the one or more computing units to assemble a target peptide by co-localizing, individually sequentially according to the determined timing, one or more ribosome-based assemblers and the two or more types charged tRNA on or in the fluidic device.

* * * * *